United States Patent
Altman et al.

(10) Patent No.: US 11,311,528 B2
(45) Date of Patent: Apr. 26, 2022

(54) OXO-TETRAHYDRO-ISOQUINOLINE CARBOXYLIC ACIDS AS STING INHIBITORS

(71) Applicants: Merck Sharp & Dohme Corp., Rahway, NJ (US); Michael D. Altman, Needham, MA (US); Matthew L. Childers, Medfield, MA (US); James P. Jewell, Newton, MA (US); Charles A. Lesburg, Waban, MA (US); Tony Siu, Brookline, MA (US)

(72) Inventors: Michael D. Altman, Needham, MA (US); Matthew L. Childers, Medfield, MA (US); James P. Jewell, Newton, MA (US); Charles A. Lesburg, Waban, MA (US); Tony Siu, Brookline, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1 day.

(21) Appl. No.: 16/980,594

(22) PCT Filed: Mar. 15, 2019

(86) PCT No.: PCT/US2019/022440
§ 371 (c)(1),
(2) Date: Sep. 14, 2020

(87) PCT Pub. No.: WO2019/182886
PCT Pub. Date: Sep. 26, 2019

(65) Prior Publication Data
US 2021/0052573 A1 Feb. 25, 2021

Related U.S. Application Data

(60) Provisional application No. 62/645,309, filed on Mar. 20, 2018, provisional application No. 62/730,588, filed on Sep. 13, 2018.

(51) Int. Cl.
| | | |
|---|---|---|
| *C07D 405/10* | (2006.01) | |
| *C07D 405/14* | (2006.01) | |
| *C07D 409/04* | (2006.01) | |
| *C07D 411/04* | (2006.01) | |
| *C07D 413/04* | (2006.01) | |
| *C07D 413/14* | (2006.01) | |
| *C07D 417/14* | (2006.01) | |
| *A61K 31/4725* | (2006.01) | |
| *A61K 31/497* | (2006.01) | |
| *A61K 31/5377* | (2006.01) | |
| *A61K 31/538* | (2006.01) | |

(52) U.S. Cl.
CPC ........ *A61K 31/4725* (2013.01); *A61K 31/497* (2013.01); *A61K 31/538* (2013.01); *A61K 31/5377* (2013.01); *C07D 405/10* (2013.01); *C07D 405/14* (2013.01); *C07D 409/04* (2013.01); *C07D 411/04* (2013.01); *C07D 413/04* (2013.01); *C07D 413/14* (2013.01); *C07D 417/14* (2013.01)

(58) Field of Classification Search
CPC .. C07D 413/04; C07D 413/14; C07D 411/04; C07D 417/14; C07D 409/04; C07D 405/10; C07D 405/14
See application file for complete search history.

(56) References Cited

U.S. PATENT DOCUMENTS

| 5,684,041 A | 11/1997 | Scherz |
| 6,509,344 B1 * | 1/2003 | Cushman ............. C07D 221/18 546/61 |
| 2005/0124614 A1 | 6/2005 | Gangloff et al. |
| 2009/0068144 A1 | 3/2009 | Weber et al. |
| 2013/0053362 A1 | 2/2013 | Castro et al. |
| 2017/0137407 A1 | 5/2017 | Castro et al. |

FOREIGN PATENT DOCUMENTS

| EP | 2149561 A1 | 2/2010 |
| WO | 2017175147 A1 | 10/2017 |

OTHER PUBLICATIONS

Sali, et al., Characterization of a Novel Human-Specific STING Agonist that Elicits Antiviral Activity Against Emerging Alphaviruses, PLOS Pathogens, 2015, 1-30, 11 (12).

* cited by examiner

*Primary Examiner* — Rebecca L Anderson
(74) *Attorney, Agent, or Firm* — Patricia A. Shatynski; John C. Todaro

(57) ABSTRACT

The instant invention provides compounds of formula I which are STING inhibitors, and as such are useful for the treatment of STING-mediated diseases such as inflammation, asthma, COPD and cancer.

25 Claims, No Drawings
Specification includes a Sequence Listing.

SEQUENCE LISTING

<160> NUMBER OF SEQ ID NOS: 2

<210> SEQ ID NO 1
<211> LENGTH: 414
<212> TYPE: PRT
<213> ORGANISM: Artificial Sequence
<220> FEATURE:
<223> OTHER INFORMATION: Full-Length HAQ STING
[STING(1-379)R71H,G230A,H232R,R293Q-GG-AviTag-GS-HRV3C-HIS8]Amino
Acid Sequence

<400> SEQUENCE: 1

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
             20                  25                  30

Leu Trp Gly Leu Gly Glu Pro Pro Glu His Thr Leu Arg Tyr Leu Val
         35                  40                  45

Leu His Leu Ala Ser Leu Gln Leu Gly Leu Leu Leu Asn Gly Val Cys
 50                  55                  60

Ser Leu Ala Glu Glu Leu His His Ile His Ser Arg Tyr Arg Gly Ser
 65                  70                  75                  80

Tyr Trp Arg Thr Val Arg Ala Cys Leu Gly Cys Pro Leu Arg Arg Gly
                 85                  90                  95

Ala Leu Leu Leu Leu Ser Ile Tyr Phe Tyr Ser Leu Pro Asn Ala
                100                 105                 110

Val Gly Pro Pro Phe Thr Trp Met Leu Ala Leu Leu Gly Leu Ser Gln
            115                 120                 125

Ala Leu Asn Ile Leu Leu Gly Leu Lys Gly Leu Ala Pro Ala Glu Ile
        130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
210                 215                 220

Leu Pro Gln Gln Thr Ala Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Gln Thr Leu Glu Asp Ile Leu Ala Asp Ala Pro Glu
290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Gly Gly Gly Leu Asn
370                 375                 380

Asp Ile Phe Glu Ala Gln Lys Ile Glu Trp His Glu Gly Ser Leu Glu
385                 390                 395                 400

Val Leu Phe Gln Gly Pro His His His His His His
                405                 410

<210> SEQ ID NO 2
<211> LENGTH: 6482

```
<212> TYPE: DNA
<213> ORGANISM: Artificial Sequence
<220> FEATURE:
<223> OTHER INFORMATION: Full-length HAQ
      [STING(1-379)R71H,G230A,H232R,R293Q-GG-AviTag-GS-HRV3C-HIS8/pBAC1]
      Plasmid DNA Sequence

<400> SEQUENCE: 2
ggaacggctc cgcccactat taatgaaatt aaaaattcca attttaaaaa acgcagcaag     60
agaaacattt gtatgaaaga atgcgtagaa ggaaagaaaa atgtcgtcga catgctgaac    120
aacaagatta atatgcctcc gtgtataaaa aaatattga acgatttgaa agaaaacaat     180
gtaccgcgcg gcggtatgta caggaagagg tttatactaa actgttacat tgcaaacgtg    240
gtttcgtgtg ccaagtgtga aaaccgatgt ttaatcaagg ctctgacgca tttctacaac    300
cacgactcca agtgtgtggg tgaagtcatg catcttttaa tcaaatccca agatgtgtat    360
aaaccaccaa actgccaaaa aatgaaaact gtcgacaagc tctgtccgtt tgctggcaac    420
tgcaagggtc tcaatcctat ttgtaattat tgaataataa acaattata atgctaaat    480 ttgtttttta ttaacgatac aaaccaaacg caacaagaac atttgtagta ttatctataa    540
ttgaaaacgc gtagttataa tcgctgaggt aatatttaaa atcattttca atgattcac    600 agttaatttg cgacaatata attttatttt cacataaact agacgccttg tcgtcttctt    660
cttcgtattc cttctctttt tcatttttct cttcataaaa attaacatag ttattatcgt    720
atccatatat gtatctatcg tatagagtaa attttttgtt gtcataaata tatatgtctt    780
ttttaatggg gtgtatagta ccgctgcgca tagttttttct gtaatttaca acagtgctat    840
tttctggtag ttcttcggag tgtgttgctt taattattaa atttatataa tcaatgaatt    900
tgggatcgtc ggttttgtac aatatgttgc cggcatagta cgcagcttct tctagttcaa    960
ttacaccatt ttttagcagc accggattaa cataactttc caaaatgttg tacgaaccgt   1020
taaacaaaaa cagttcacct cccttttcta tactattgtc tgcgagcagt tgtttgttgt   1080
taaaaataac agccattgta atgagacgca caaactaata tcacaaactg gaaatgtcta   1140
tcaatatata gttgctgatc agatctgatc atggagataa ttaaaatgat aaccatctcg   1200
caaataaata agtattttac tgttttcgta acagttttgt aataaaaaaa cctataaata   1260
taggatccat gccccactcc agcctgcatc catccatccc gtgtcccagg ggtcacgggg   1320
cccagaaggc agccttggtt ctgctgagtg cctgcctggt gacccttggg gggctaggag   1380
agccaccaga gcacactctc cggtacctgg tgctccacct agcctccctg cagctgggac   1440
tgctgttaaa cggggtctgc agcctggctg aggagctgca ccacatccac tccaggtacc   1500
ggggcagcta ctggaggact gtgcgggcct gcctgggctg ccccctccgc cgtggggccc   1560
tgttgctgct gtccatctat ttctactact ccctcccaaa tgcggtcggc ccgcccttca   1620
cttggatgct tgccctcctg ggcctctcgc aggcactgaa catcctcctg ggcctcaagg   1680
gcctggcccc agctgagatc tctgcagtgt gtgaaaaagg gaatttcaac gtggcccatg   1740
ggctggcatg gtcatattac atcggatatc tgcggctgat cctgccagag ctccaggccc   1800
ggattcgaac ttacaatcag cattacaaca acctgctacg gggtgcagtg agccagcggc   1860
tgtatattct cctcccattg gactgtgggg tgcctgataa cctgagtatg gctgacccca   1920
acattcgctt cctggataaa ctgcccagc agaccgctga ccgtgctggc atcaaggatc   1980
gggtttacag caacagcatc tatgagcttc tggagaacgg gcagcgggcg ggcacctgtg   2040
tcctggagta cgccaccccc ttgcagactt tgtttgccat gtcacaatac agtcaagctg   2100
```

```
gctttagccg ggaggatagg cttgagcagg ccaaactctt ctgccagaca cttgaggaca    2160
tcctggcaga tgcccctgag tctcagaaca actgccgcct cattgcctac caggaacctg    2220
cagatgacag cagcttctcg ctgtcccagg aggttctccg gcacctgcgg caggaggaaa    2280
aggaagaggt tactgtgggc agcttgaaga cctcagcggt gcccagtacc tccacgatgt    2340
cccaagagcc tgagctcctc atcagtggaa tggaaaagcc cctccctctc cgcacggatt    2400
tctctggcgg tggcctgaac gacatcttcg aagcccagaa aatcgaatgg catgaaggca    2460
gcctggaagt gctgttccag ggcccacacc accatcatca ccatcaccat taatgagcgg    2520
ccgcactcga gcaccaccac caccaccact aacctaggta gctgagcgca tgcaagctga    2580
tccgggttat tagtacattt attaagcgct agattctgtg cgttgttgat ttacagacaa    2640
ttgttgtacg tattttaata attcattaaa tttataatct ttagggtggt atgttagagc    2700
gaaaatcaaa tgattttcag cgtctttata tctgaattta aatattaaat cctcaataga    2760
tttgtaaaat aggtttcgat tagtttcaaa caagggttgt ttttccgaac cgatggctgg    2820
actatctaat ggattttcgc tcaacgccac aaaacttgcc aaatcttgta gcagcaatct    2880
agctttgtcg atattcgttt gtgttttgtt ttgtaataaa ggttcgacgt cgttcaaaat    2940
attatgcgct tttgtatttc tttcatcact gtcgttagtg tacaattgac tcgacgtaaa    3000
cacgttaaat agagcttgga catatttaac atcgggcgtg ttagctttat taggccgatt    3060
atcgtcgtcg tcccaaccct cgtcgttaga agttgcttcc gaagacgatt ttgccatagc    3120
cacacgacgc ctattaattg tgtcggctaa cacgtccgcg atcaaatttg tagttgagct    3180
ttttggaatt atttctgatt gcgggcgttt ttgggcgggt ttcaatctaa ctgtgcccga    3240
ttttaattca gacaacacgt tagaaagcga tggtgcaggc ggtggtaaca tttcagacgg    3300
caaatctact aatggcggcg gtggtggagc tgatgataaa tctaccatcg gtggaggcgc    3360
aggcggggct ggcggcggag gcggaggcgg aggtggtggc ggtgatgcag acggcggttt    3420
aggctcaaat gtctctttag gcaacacagt cggcacctca actattgtac tggtttcggg    3480
cgccgttttt ggtttgaccg gtctgagacg agtgcgattt ttttcgtttc taatagcttc    3540
caacaattgt tgtctgtcgt ctaaaggtgc agcgggttga ggttccgtcg gcattggtgg    3600
agcgggcggc aattcagaca tcgatggtgg tggtggtggt ggaggcgctg gaatgttagg    3660
cacgggagaa ggtggtggcg gcggtgccgc cggtataatt tgttctggtt tagtttgttc    3720
gcgcacgatt gtgggcaccg gcgcaggcgc cgctggctgc acaacggaag gtcgtctgct    3780
tcgaggcagc gcttggggtg gtggcaattc aatattataa ttggaataca aatcgtaaaa    3840
atctgctata agcattgtaa tttcgctatc gtttaccgtg ccgatattta acaaccgctc    3900
aatgtaagca attgtattgt aaagagattg tctcaagctc ggatcgatcc cgcacgccga    3960
taacaagcct tttcattttt actacagcat tgtagtggcg agacacttcg ctgtcgtcga    4020
ggtttaaacg cttcctcgct cactgactcg ctgcgctcgg tcgttcggct gcggcgagcg    4080
gtatcagctc actcaaaggc ggtaatacgg ttatccacag aatcagggga taacgcagga    4140
aagaacatgt gagcaaaagg ccagcaaaag gccaggaacc gtaaaaaggc cgcgttgctg    4200
gcgttttcc ataggctccg ccccctgac gagcatcaca aaaatcgacg ctcaagtcag    4260
aggtggcgaa acccgacagg actataaaga taccaggcgt ttccccctgg aagctccctc    4320
gtgcgctctc ctgttccgac cctgccgctt accggatacc tgtccgcctt tctcccttcg    4380
ggaagcgtgg cgctttctca tagctcacgc tgtaggtatc tcagttcggt gtaggtcgtt    4440
cgctccaagc tgggctgtgt gcacgaaccc cccgttcagc ccgaccgctg cgccttatcc    4500
```

-continued

```
ggtaactatc gtcttgagtc caacccggta agacacgact tatcgccact ggcagcagcc      4560
actggtaaca ggattagcag agcgaggtat gtaggcggtg ctacagagtt cttgaagtgg      4620
tggcctaact acggctacac tagaaggaca gtatttggta tctgcgctct gctgaagcca      4680
gttaccttcg gaaaaagagt tggtagctct tgatccggca aacaaaccac cgctggtagc      4740
ggtggttttt ttgtttgcaa gcagcagatt acgcgcagaa aaaaggatc tcaagaagat      4800 cctttgatct tttctacggg gtctgacgct cagtggaacg aaaactcacg ttaagggatt      4860
ttggtcatga gattatcaaa aaggatcttc acctagatcc ttttaaatta aaaatgaagt      4920
tttaaatcaa tctaaagtat atatgagtaa acttggtctg acagttacca atgcttaatc      4980
agtgaggcac ctatctcagc gatctgtcta tttcgttcat ccatagttgc ctgactcccc      5040
gtcgtgtaga taactacgat acgggagggc ttaccatctg gccccagtgc tgcaatgata      5100
ccgcgagacc cacgctcacc ggctccagat ttatcagcaa taaaccagcc agccggaagg      5160
gccgagcgca gaagtggtcc tgcaacttta tccgcctcca tccagtctat taattgttgc      5220
cgggaagcta gagtaagtag ttcgccagtt aatagtttgc gcaacgttgt tgccattgct      5280
acaggcatcg tggtgtcacg ctcgtcgttt ggtatggctt cattcagctc cggttcccaa      5340
cgatcaaggc gagttacatg atcccccatg ttgtgcaaaa aagcggttag ctccttcggt      5400
cctccgatcg ttgtcagaag taagttggcc gcagtgttat cactcatggt tatggcagca      5460
ctgcataatt ctcttactgt catgccatcc gtaagatgct tttctgtgac tggtgagtac      5520
tcaaccaagt cattctgaga atagtgtatg cggcgaccga gttgctcttg cccggcgtca      5580
atacgggata ataccgcgcc acatagcaga actttaaaag tgctcatcat tggaaaacgt      5640 tcttcgggc gaaaactctc aaggatctta ccgctgttga tccagttc gatgtaaccc      5700 actcgtgcac ccaactgatc ttcagcatct tttactttca ccagcgtttc tgggtgagca      5760
aaaacaggaa ggcaaaatgc cgcaaaaaag ggaataaggg cgacacggaa atgttgaata      5820
ctcatactct tcctttttca atattattga agcatttatc agggttattg tctcatgagc      5880
ggatacatat ttgaatgtat ttagaaaaat aaacaaatag gggttccgcg cacatttccc      5940
cgaaaagtgc cacctgacgc gccctgtagc ggcgcattaa gcgcggcggg tgtggtggtt      6000
acgcgcagcg tgaccgctac acttgccagc gccctagcgc ccgctccttt cgctttcttc      6060
ccttcctttc tcgccacgtt cgccggcttt ccccgtcaag ctctaaatcg ggggctccct      6120
ttagggttcc gatttagtgc tttacggcac ctcgacccca aaaaacttga ttagggtgat      6180
ggttcacgta gtgggccatc gccctgatag acggtttttc gccctttgac gttggagtcc      6240
acgttcttta atagtggact cttgttccaa actggaacaa cactcaaccc tatctcggtc      6300
tattcttttg atttataagg gattttgccg atttcggcct attggttaaa aaatgagctg      6360
atttaacaaa aatttaacgc gaattttaac aaaatattaa cgtttacaat ttcccattcg      6420
ccattcaggc tgcgcaactg ttgggaaggg cgatcggtgc gggcctcttc gctattacgc      6480
ca                                                                     6482
```

OXO-TETRAHYDRO-ISOQUINOLINE CARBOXYLIC ACIDS AS STING INHIBITORS

CROSS REFERENCE TO RELATED APPLICATIONS

This application is a U.S. National Phase application under 35 U.S.C. § 371 of PCT Application No. PCT/US2019/022440, filed Mar. 15, 2019 which claims priority under 35 U.S.C. § 119(e) from U.S. Provisional Application Ser. No. 62/645,309, filed on Mar. 20, 2018 and U.S. Provisional Application Ser. No. 62/730,588, filed on Sep. 13, 2018.

BACKGROUND OF INVENTION

The principal role of the human immune system is to maintain the body's equilibrium in the face of external and internal threats. The durable response to foreign insults (e.g., bacterial or viral infection) comes from the adaptive immune system. This response lasts the life of the host, and is characterized by the generation of antigen-specific T cells that are capable of recognizing re-challenge by the same pathogen, and shortening the timeframe to which deep immune protection can occur. Since generation of these durable responses takes weeks to develop, additional aspects of immunity compensate for the time gap.

The immediate response to a foreign insult comes from the innate arm of the immune system. This response launches within moments to hours, and is spurred by the receptor-mediated recognition of common features of that pathogen—for example, components of bacterial cell walls or viral nucleic acid motifs—and not in a sequence-specific manner like the adaptive response. These motifs are pathogen-associated molecular patterns (PAMPs), and favor speed over specificity. The innate immune system also responds to other "danger signals" that come from the host itself—signs of tissue damage or wounding that signify potential danger despite the absence of a PAMP. These "damage associated molecular patterns" (DAMPs) can stimulate similar cellular responses as an infectious agent, thus providing broad protection against a range of threats to the host.

DNA in the cytoplasm is one such DAMP/PAMP. cGAS (cyclic GMP-AMP synthase) has been described as the crucial receptor that recognizes DNA in the cytoplasm. Cytoplasmic DNA can function as either a DAMP (e.g., mitochondrial disruption could allow DNA to access the cytoplasm) or a PAMP (e.g., a DNA virus infecting a cell). Upon recognition of cytosolic DNA, cGAS catalyzes the generation of the cyclic-dinucleotide 2'-3' cGAMP, an atypical second messenger that strongly binds to the ER-transmembrane adaptor protein STING (Stimulator of Interferon Genes). When 2'3' cGAM P binds to STING, the protein undergoes a conformnational change, and translocates within the cell to a perinuclear compartment. This translocation induces the activation of critical transcription factors IRF-3 and NF-κB. Transcription factor activation leads to induction of type I interferons (IFNs) and production of pro-inflammatory cytokines such as IL-6, TNF-α and IFN-γ.

The function of these cytokines on immune cells is well established. Specifically. T cell activation is stimulated, as these cytokines enhance the antigen presentation capacity of macrophages and dendritic cells. Type I IFNs are best characterized for their "anti-viral" activity—notably, they stimulate dozens of cellular processes that drive toward clearing a viral insult. These include inhibition of viral replication, affecting the cell cycle so that infected cells are less able to divide, inhibiting budding of viral particles, affecting expression of antigen presentation machinery, and more.

These anti-viral processes driven by STING activation can become dysregulated, and their dysregulation could cause or exacerbate inflammatory, autoimmune, or other disorders where DNA gains access to the cytoplasm of cells. These disorders are characterized by abnormal cytokine responses, and interfering with STING signaling in these disorders could reduce or prevent this cytokine production. Mouse models of DNA-driven inflammation have observed abrogation of symptoms when STING is genetically deleted. (See Lood, Christian, et al., Nature Medicine, Vol. 22, No. 2, 146-153 (February 2016); and Gehrke, Nadine, et al., Immunity 39, 482-495, Sep. 19, 2013). Additionally, in a deeper study involving human patients with Systemic lupus erythematous (SLE) it was observed that oxidized DNA is associated with SLE pathology. (Caielli, Simone, et al., J of Experimental Med., Vol. 213, No. 5, 697-713, (2016). SLE is a prototypical example of a disorder where cytokine response is abnormal. SLE is characterized by chronic, high levels of type I IFNs, as well as circulating immune complexes (formed of antibody-antigen aggregates that are not successfully cleared). Most patients with SLE have high levels of circulating DNA, and have generated inappropriately aggressive innate and adaptive responses to that DNA. This prominent role for both DNA and type I IFNs suggests that inhibitors of the cGAS/STING pathway could have therapeutic benefit in such a disorder.

SUMMARY OF THE INVENTION

The present invention provides novel compounds which are inhibitors of STING activity. The invention also provides a method for the treatment and prevention of STING-mediated diseases and disorders using the novel compounds, as well as pharmaceutical compositions containing the compounds.

The invention is also directed to methods of inhibiting STING activity, and methods of treating diseases, such as disorders of immunity and inflammation, in which suppression of STING plays a role as immunosuppressants. Methods of using STING inhibitory compounds to inhibit cancer cell growth or proliferation are also provided.

DETAILED DESCRIPTION OF THE INVENTION

Compounds are provided that inhibit type I interferon (type 1 IFN) production, specifically compounds that inhibit stimulator of interferon genes (STING) pathway. The invention provides methods of using STING antagonistic compounds to inhibit STING mediated processes in vitro and in vivo.

The present invention provides compounds of formula I or pharmaceutically acceptable salts thereof:

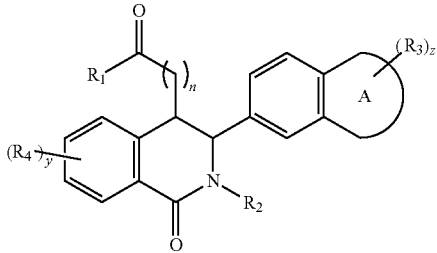

wherein: A is a 5- to 7-membered unsaturated non-aromatic ring having 1 or 2 heteroatoms independently selected from oxygen, nitrogen and sulfur;
$R_1$ is selected from —OH, amino, —NHOH, —N($C_{1-6}$ alkyl)$_2$, and —N($C_{1-6}$ alkyl);
n is 0, 1, 2, or 3;
z is 0, 1, 2, or 3;
y is 0, 1, 2, or 3;
each $R_3$ is independently selected from $C_{1-10}$ alkyl, $C_{1-10}$ haloalkyl, $C_{3-7}$cycloalkyl$C_{0-6}$alkyl, and $C_{3-7}$heterocycloalkyl$C_{0-6}$alkyl,
$R_2$ is phenyl or pyridyl, wherein $R_2$ is substituted by 0, 1, 2, or 3 $R_5$ substituents and wherein two $R_5$ may join together with the ring atoms to which they are attached to form a 3- to 6-membered ring;
each $R_4$ is independently selected from halogen, —($C_{1-6}$ alkyl)OH, hydroxy, $C_{1-10}$ haloalkyl, $C_{2-10}$ alkenyl, $C_{1-6}$ alkyl, and aryl($C_{0-10}$ alkyl)oxy($C_{0-10}$ alkyl;
each $R_5$ is independently selected from:
halogen,
$C_{1-10}$ alkyl(oxy)$_{0-1}$$C_{1-10}$ alkyl,
$C_{1-10}$ heteroalkyl(oxy)$_{0-1}$$C_{1-10}$ alkyl,
$C_{2-10}$ alkenyl(oxy)$_{0-1}$$C_{1-10}$ alkyl,
aryl $C_{1-10}$ alkyl(oxy)$_{0-1}$$C_{1-10}$ alkyl,
$C_{3-12}$ cycloalkyl $C_{0-10}$ alkyl(oxy)$_{0-1}$$C_{1-10}$ alkyl,
heteroaryl $C_{1-10}$ alkyl(oxy)$_{0-1}$$C_{1-10}$ alkyl,
($C_{3-12}$)heterocycloalkyl $C_{0-10}$ alkyl(oxy)$_{0-1}$$C_{1-10}$ alkyl,
amino,
$C_{1-10}$ alkylamino$C_{1-10}$ alkyl,
($C_{1-10}$)heteroalkyl(oxy)$_{0-1}$(carbonyl)$_{0-1}$amino$C_{0-10}$ alkyl,
$C_{3-12}$ cycloalkyl $C_{0-10}$ alkyl(oxy)$_{0-1}$(carbonyl)$_{0-1}$amino$C_{0-1}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
($C_{3-12}$)heterocycloalkyl $C_{0-10}$ alkyl(oxy)$_{0-1}$(carbonyl)$_{0-1}$amino$C_{0-10}$ alkyl,
$C_{0-10}$ alkylamino (carbonyl)$_{0-1}$$C_{0-10}$ alkyl,
($C_{1-10}$)heteroalkylamino (carbonyl)$_{0-1}$$C_{0-10}$ alkyl,
$C_{3-12}$ cycloalkylamino (carbonyl)$_{0-1}$$C_{0-10}$ alkyl,
aryl $C_{0-10}$ alkylamino (carbonyl)$C_{0-10}$ alkyl,
heteroaryl $C_{0-10}$ alkylamino(carbonyl)$_{0-1}$$C_{0-10}$ alkyl,
($C_{3-12}$)heterocycloalkylamino(carbonyl)$_{0-1}$$C_{0-10}$ alkyl,
$C_{1-10}$ alkylsulfonyl$C_{0-10}$ alkyl,
$C_{1-10}$ heteroalkylsulfonyl$C_{0-10}$ alkyl,
($C_{3-12}$)cycloalkyl$C_{0-10}$alkylsulfonyl$C_{0-10}$ alkyl,
($C_{3-12}$)cycloheteroalkyl$C_{0-10}$alkylsulfonyl$C_{0-10}$ alkyl,
heteroaryl$C_{0-10}$ alkylsulfonyl$C_{0-10}$ alkyl,
aryl$C_{0-10}$ alkylsulfonyl$C_{0-10}$ alkyl,
$C_{1-10}$ alkylsulfonylamino$C_{0-10}$ alkyl,
($C_{1-10}$ alkyl)$_{1-2}$ amino, —$SO_2NH_2$,
—$SO_2NH$($C_{1-10}$ alkyl),
—$SO_2N$($C_{1-10}$ alkyl)$_2$,
—$SO_2CF_3$,
—$SO_2CF_2H$,
—SH,
—S($C_{1-10}$ alkyl),
—NH=$CH_2$,
hydroxy,
—($C_{1-10}$ alkyl)OH,
—$C_{0-10}$ alkylalkoxy,
cyano,
—($C_{1-6}$alkyl)cyano, and
$C_{1-6}$haloalkyl(oxy); wherein each $R_5$ is substituted with 0, 1, 2 or 3 $R_6$ substituents each independently selected by halogen, cyano, oxo, $C_{1-10}$ alkylcarbonyl$C_{0-10}$ alkyl, $C_{1-10}$ alkyl, $C_{1-10}$ alkylcarbonylamino$C_{0-10}$ alkyl, and —($C_{1-10}$ alkyl)OH.

Representative compounds of the instant invention include, but are not limited to, the following compounds and their pharmaceutically acceptable salts thereof.

2-(4-(tert-butyl)-3-chlorophenyl)-3-(2,3-dihydrobenzo[b][1,4]dioxin-6-yl)-1-oxo-1,2,3,4-tetrahydroisoquinoline-4-carboxylic acid;

2-(4-(tert-butyl)-3-chlorophenyl)-3-(2,3-dihydrobenzo[b][1,4]dioxin-6-yl)-7-fluoro-1-oxo-1,2,3,4-tetrahydroisoquinoline-4-carboxylic acid;

3-(2,3-dihydro-1,4-benzodioxin-6-yl)-2-[4-(1-methylethyl)phenyl]-1-oxo-1,2,3,4-tetrahydroisoquinoline-4-carboxylic acid;

3-(2,3-dihydro-1,4-benzodioxin-6-yl)-2-(2,3-dihydro-1H-inden-5-yl)-1-oxo-1,2,3,4-tetrahydroisoquinoline-4-carboxylic acid;

3-(2,3-dihydro-1,4-benzodioxin-6-yl)-2-(4-morpholin-4-ylphenyl)-1-oxo-1,2,3,4-tetrahydroisoquinoline-4-carboxylic acid;

3-(2,3-dihydro-1,4-benzodioxin-6-yl)-2-[4-(methylsulfonyl)phenyl]-1-oxo-1,2,3,4-tetrahydroisoquinoline-4-carboxylic acid;

3-(2,3-dihydro-1,4-benzodioxin-6-yl)-2-[4-(dimethylsulfamoyl)phenyl]-1-oxo-1,2,3,4-tetrahydroisoquinoline-4-carboxylic acid;

(-2-[4-(1-cyano-1-methylethyl)phenyl]-3-(2,3-dihydro-1,4-benzodioxin-6-yl)-1-oxo-1,2,3,4-tetrahydroisoquinoline-4-carboxylic acid;

2-(2-chloropyridin-4-yl)-3-(2,3-dihydro-1,4-benzodioxin-6-yl)-1-oxo-1,2,3,4-tetrahydroisoquinoline-4-carboxylic acid;

2-(4-cyclopropylphenyl)-3-(2,3-dihydro-1,4-benzodioxin-6-yl)-1-oxo-1,2,3,4-tetrahydroisoquinoline-4-carboxylic acid;

2-[4-(4-acetylpiperazin-1-yl)phenyl]-3-(2,3-dihydro-1,4-benzodioxin-6-yl)-1-oxo-1,2,3,4-tetrahydroisoquinoline-4-carboxylic acid;

3-(2,3-dihydro-1,4-benzodioxin-6-yl)-2-{4-[1-(2-hydroxyethyl)-1H-pyrazol-4-yl]phenyl}-1-oxo-1,2,3,4-tetrahydroisoquinoline-4-carboxylic acid;

2-[4-(difluoromethoxy)phenyl]-3-(2,3-dihydro-1,4-benzodioxin-6-yl)-1-oxo-1,2,3,4-tetrahydroisoquinoline-4-carboxylic acid;

2-(1,3-benzothiazol-5-yl)-3-(2,3-dihydro-1,4-benzodioxin-6-yl)-1-oxo-1,2,3,4-tetrahydroisoquinoline-4-carboxylic acid;

3-(2,3-dihydro-1,4-benzodioxin-6-yl)-2-(3,3-dimethyl-2-oxo-2,3-dihydro-1H-indol-6-yl)-1-oxo-1,2,3,4-tetrahydroisoquinoline-4-carboxylic acid;

3-(2,3-dihydro-1,4-benzodioxin-6-yl)-1-oxo-2-[4-(1H-pyrazol-5-yl)phenyl]-1,2,3,4-tetrahydroisoquinoline-4-carboxylic acid;

2-(4-chloro-3-fluorophenyl)-3-(2,3-dihydro-1,4-benzodioxin-6-yl)-1-oxo-1,2,3,4-tetrahydroisoquinoline-4-carboxylic acid;

2-(4-chloro-3-cyclopropylphenyl)-3-(2,3-dihydro-1,4-benzodioxin-6-yl)-1-oxo-1,2,3,4-tetrahydroisoquinoline-4-carboxylic acid;

2-(3-cyano-4-morpholin-4-ylphenyl)-3-(2,3-dihydro-1,4-benzodioxin-6-yl)-1-oxo-1,2,3,4-tetrahydroisoquinoline-4-carboxylic acid;

2-[3-chloro-4-(difluoromethoxy)phenyl]-3-(2,3-dihydro-1,4-benzodioxin-6-yl)-1-oxo-1,2,3,4-tetrahydroisoquinoline-4-carboxylic acid;

3-(2,3-dihydro-1,4-benzodioxin-6-yl)-2-[4-(2-hydroxy-1,1-dimethylethyl)phenyl]-1-oxo-1,2,3,4-tetrahydroisoquinoline-4-carboxylic acid;

2-(3-chlorophenyl)-3-(2,3-dihydro-1,4-benzodioxin-6-yl)-1-oxo-1,2,3,4-tetrahydroisoquinoline-4-carboxylic acid;

2-(3-chloro-4-morpholin-4-ylphenyl)-3-(2,3-dihydro-1,4-benzodioxin-6-yl)-1-oxo-1,2,3,4-tetrahydroisoquinoline-4-carboxylic acid;

3-(2,3-dihydro-1,4-benzodioxin-6-yl)-2-(2-methylpyridin-4-yl)-1-oxo-1,2,3,4-tetrahydroisoquinoline-4-carboxylic acid;

3-(2,3-dihydro-1,4-benzodioxin-6-yl)-1-oxo-2-[4-(2,2,2-trifluoroethoxy)phenyl]-1,2,3,4-tetrahydroisoquinoline-4-carboxylic acid;

2-{4-[(4-chlorophenyl)carbamoyl]phenyl}-3-(2,3-dihydro-1,4-benzodioxin-6-yl)-1-oxo-1,2,3,4-tetrahydroisoquinoline-4-carboxylic acid;

2-(4-cyclohexylphenyl)-3-(2,3-dihydro-1,4-benzodioxin-6-yl)-1-oxo-1,2,3,4-tetrahydroisoquinoline-4-carboxylic acid;

2-[4-(1-cyanocyclohexyl)phenyl]-3-(2,3-dihydro-1,4-benzodioxin-6-yl)-1-oxo-1,2,3,4-tetrahydroisoquinoline-4-carboxylic acid;

3-(2,3-dihydro-1,4-benzodioxin-6-yl)-1-oxo-2-(5,6,7,8-tetrahydronaphthalen-2-yl)-1,2,3,4-tetrahydroisoquinoline-4-carboxylic acid;

3-(2,3-dihydro-1,4-benzodioxin-6-yl)-2-(2-fluoropyridin-4-yl)-1-oxo-1,2,3,4-tetrahydroisoquinoline-4-carboxylic acid;

3-(2,3-dihydro-1,4-benzodioxin-6-yl)-2-[6-(hydroxymethyl)-5,6,7,8-tetrahydronaphthalen-2-yl]-1-oxo-1,2,3,4-tetrahydroisoquinoline-4-carboxylic acid;

2-(2-chloro-6-methylpyridin-4-yl)-3-(2,3-dihydro-1,4-benzodioxin-6-yl)-1-oxo-1,2,3,4-tetrahydroisoquinoline-4-carboxylic acid;

2-(4-chloro-3-methylphenyl)-3-(2,3-dihydro-1,4-benzodioxin-6-yl)-1-oxo-1,2,3,4-tetrahydroisoquinoline-4-carboxylic acid;

3-(2,3-dihydro-1,4-benzodioxin-6-yl)-2-(4-{[(methylsulfonyl)amino]methyl}phenyl)-1-oxo-1,2,3,4-tetrahydroisoquinoline-4-carboxylic acid;

3-(2,3-dihydro-1,4-benzodioxin-6-yl)-2-(2,6-dimethylpyridin-4-yl)-1-oxo-1,2,3,4-tetrahydroisoquinoline-4-carboxylic acid;

2-[4-(I-cyanocyclohexyl)phenyl]-3-(2,3-dihydro-1,4-benzodioxin-6-yl)-1-oxo-1,2,3,4-tetrahydroisoquinoline-4-carboxylic acid;

3-(2,3-dihydro-1,4-benzodioxin-6-yl)-1-oxo-2-(5,6,7,8-tetrahydronaphthalen-2-yl)-1,2,3,4-tetrahydroisoquinoline-4-carboxylic acid;

2-[3-chloro-4-(morpholin-4-ylmethyl)phenyl]-3-(2,3-dihydro-1,4-benzodioxin-6-yl)-1-oxo-1,2,3,4-tetrahydroisoquinoline-4-carboxylic acid;

3-(2,3-dihydro-1,4-benzodioxin-6-yl)-2-(3,4-dimethylphenyl)-1-oxo-1,2,3,4-tetrahydroisoquinoline-4-carboxylic acid;

2-(3,4-dichlorophenyl)-3-(2,3-dihydro-1,4-benzodioxin-6-yl)-1-oxo-1,2,3,4-tetrahydroisoquinoline-4-carboxylic acid;

2-[4-(benzyloxy)-3-chlorophenyl]-3-(2,3-dihydro-1,4-benzodioxin-6-yl)-1-oxo-1,2,3,4-tetrahydroisoquinoline-4-carboxylic acid;

2-(3-bromophenyl)-3-(2,3-dihydro-1,4-benzodioxin-6-yl)-1-oxo-1,2,3,4-tetrahydroisoquinoline-4-carboxylic acid;

2-(4-cyclopropyl-3-fluorophenyl)-3-(2,3-dihydro-1,4-benzodioxin-6-yl)-1-oxo-1,2,3,4-tetrahydroisoquinoline-4-carboxylic acid;

2-[4-(1-cyanocyclohexyl)phenyl]-3-(3,4-dihydro-2H-1,5-benzodioxepin-7-yl)-1-oxo-1,2,3,4-tetrahydroisoquinoline-4-carboxylic acid;

2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

6-bromo-3-(2,3-dihydro-1,4-benzodioxin-6-yl)-2-(2,3-dihydro-1H-inden-5-yl)-1-oxo-1,2,3,4-tetrahydroisoquinoline-4-carboxylic acid;

3-(2,3-dihydro-1,4-benzodioxin-6-yl)-2-naphthalen-2-yl-1-oxo-1,2,3,4-tetrahydroisoquinoline-4-carboxylic acid;

3-(2,3-dihydro-1,4-benzodioxin-6-yl)-1-oxo-2-(3,4,5-trichlorophenyl)-1,2,3,4-tetrahydroisoquinoline-4-carboxylic acid;

2-[3-chloro-4-(1-cyano-1-methylethyl)phenyl]-3-(2,3-dihydro-1,4-benzodioxin-6-yl)-1-oxo-1,2,3,4-tetrahydroisoquinoline-4-carboxylic acid;

6-bromo-2-(3-chloro-4-methylphenyl)-3-(2,3-dihydro-1,4-benzodioxin-6-yl)-1-oxo-1,2,3,4-tetrahydroisoquinoline-4-carboxylic acid;

7-bromo-2-(3-chloro-4-methylphenyl)-3-(2,3-dihydro-1,4-benzodioxin-6-yl)-1-oxo-1,2,3,4-tetrahydroisoquinoline-4-carboxylic acid;

3-(2,3-dihydro-1,4-benzodioxin-6-yl)-2-(3,4-dihydro-1H-isochromen-7-yl)-1-oxo-1,2,3,4-tetrahydroisoquinoline-4-carboxylic acid;

2-(3-chloro-4-cyclohexylphenyl)-3-(2,3-dihydro-1,4-benzodioxin-6-yl)-1-oxo-1,2,3,4-tetrahydroisoquinoline-4-carboxylic acid;

2-(4-tert-butyl-3-chlorophenyl)-3-(3,4-dihydro-2H-chromen-6-yl)-1-oxo-1,2,3,4-tetrahydroisoquinoline-4-carboxylic acid;

7-bromo-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

2-(4-tert-butyl-3-chlorophenyl)-7-chloro-3-(2,3-dihydro-1,4-benzodioxin-6-yl)-1-oxo-1,2,3,4-tetrahydroisoquinoline-4-carboxylic acid;

7-(benzyloxy)-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

2-(4-tert-butyl-3-chlorophenyl)-3-(2,3-dihydro-1,4-benzodioxin-6-yl)-6-fluoro-1-oxo-1,2,3,4-tetrahydroisoquinoline-4-carboxylic acid;

2-(4-tert-butyl-3-chlorophenyl)-7-chloro-3-(2,3-dihydro-1,4-benzodioxin-6-yl)-1-oxo-1,2,3,4-tetrahydroisoquinoline-4-carboxylic acid;

2-(4-tert-butyl-3-chlorophenyl)-3-(4-methyl-3,4-dihydro-2H-1,4-benzoxazin-6-yl)-1-oxo-1,2,3,4-tetrahydroisoquinoline-4-carboxylic acid;

2-(4-tert-butyl-3-chlorophenyl)-3-(2,3-dihydro-1,4-benzodioxin-6-yl)-7-hydroxy-1-oxo-1,2,3,4-tetrahydroisoquinoline-4-carboxylic acid;

2-[3-chloro-4-(1-cyanocyclopropyl)phenyl]-3-(2,3-dihydro-1,4-benzodioxin-6-yl)-1-oxo-1,2,3,4-tetrahydroisoquinoline-4-carboxylic acid;

2-(4'-acetamido-[1,1'-biphenyl]-4-yl)-3-(2,3-dihydrobenzo[b][1,4]dioxin-6-yl)-1-oxo-1,2,3,4-tetrahydroisoquinoline-4-carboxylic acid;

2-[4-(I-acetylpiperidin-4-yl)phenyl]-3-(2,3-dihydro-1,4-benzodioxin-6-yl)-1-oxo-1,2,3,4-tetrahydroisoquinoline-4-carboxylic acid;

(2-(4'-acetamido-2-chloro-[1,1'-biphenyl]-4-yl)-3-(2,3-dihydrobenzo[b][1,4]dioxin-6-yl)-1-oxo-1,2,3,4-tetrahydroisoquinoline-4-carboxylic acid;

2-[4-(1-acetylpiperidin-4-yl)-3-methylphenyl]-3-(2,3-dihydro-1,4-benzodioxin-6-yl)-1-oxo-1,2,3,4-tetrahydroisoquinoline-4-carboxylic acid;

2-{4-[cis-4-(acetylamino)cyclohexyl]phenyl}-3-(2,3-dihydro-1,4-benzodioxin-6-yl)-1-oxo-1,2,3,4-tetrahydroisoquinoline-4-carboxylic acid;

2-{4-[trans-4-(acetylamino)cyclohexyl]phenyl}-3-(2,3-dihydro-1,4-benzodioxin-6-yl)-1-oxo-1,2,3,4-tetrahydroisoquinoline-4-carboxylic acid;

2-(4-(tert-butyl)-3-chlorophenyl)-3-(2,3-dihydrobenzo[b][1,4]dioxin-6-yl)-N-methyl-1-oxo-1,2,3,4-tetrahydroisoquinoline-4-carboxamide;

2-(4-ter-t-butyl-3-chlorophenyl)-3-(2,3-dihydro-1,4-benzodioxin-6-yl)-1-oxo-1,2,3,4-tetrahydroisoquinoline-4-carboxamide;

2-(4-tert-butyl-3-chlorophenyl)-3-(2,3-dihydro-1,4-benzodioxin-6-yl)-7-fluoro-1-oxo-1,2,3,4-tetrahydroisoquinoline-4-carboxamide;

2-(4-(tert-butyl)-3-chlorophenyl)-3-(2,3-dihydrobenzo[b][1,4]dioxin-6-yl)-1-oxo-7-vinyl-1,2,3,4-tetrahydroisoquinoline-4-carboxylic acid;

2-(4-tert-butyl-3-chlorophenyl)-3-(2,3-dihydro-1,4-benzodioxin-6-yl)-7-fluoro-1-oxo-1,2,3,4-tetrahydroisoquinoline-4-carboxamide;

2-(4-(tert-butyl)-3-chlorophenyl)-3-(2,3-dihydrobenzo[b][1,4]dithiin-6-yl)-1-oxo-1,2,3,4-tetrahydroisoquinoline-4-carboxylic acid;

2-(4-(tert-butyl)-3-chlorophenyl)-3-(2,3-dihydrobenzo[b][1,4]oxathiin-6-yl)-1-oxo-1,2,3,4-tetrahydroisoquinoline-4-carboxylic acid;

2-(4-(tert-butyl)-3-chlorophenyl)-3-(2,3-dihydrobenzo[b][1,4]oxathiin-7-yl)-1-oxo-1,2,3,4-tetrahydroisoquinoline-4-carboxylic acid;

2-(4-(tert-butyl)-3-chlorophenyl)-3-(2,3-dihydrobenzo[b][1,4]dioxin-6-yl)-N-hydroxyl-1-oxo-1,2,3,4-tetrahydroisoquinoline-4-carboxamide;

2-(4-(tert-butyl)-3-chlorophenyl)-3-(chroman-6-yl)-1-oxo-1,2,3,4-tetrahydroisoquinoline-4-carboxylic acid;

2-(4-(tert-butyl)-3-chlorophenyl)-3-(3,4-dihydro-2H-benzo[b][1,4]oxazin-6-yl)-1-oxo-1,2,3,4-tetrahydroisoquinoline-4-carboxylic acid;

2-(4-(tert-butyl)-3-chlorophenyl)-3-(4-isopropyl-3,4-dihydro-2H-benzo[b][1,4]oxazin-6-yl)-1-oxo-1,2,3,4-tetrahydroisoquinoline-4-carboxylic acid;

2-(4-(tert-butyl)-3-chlorophenyl)-3-(3-cyclopropyl-2,3-dihydrobenzo[b][1,4]dioxin-6-yl)-7-fluoro-1-oxo-1,2,3,4-tetrahydroisoquinoline-4-carboxylic acid;

2-(4-(tert-butyl)-3-chlorophenyl)-3-(2,3-dihydrobenzo[b][1,4]oxathiin-6-yl)-7-fluoro-1-oxo-1,2,3,4-tetrahydroisoquinoline-4-carboxylic acid;

(2-(4-(tert-butyl)-3-chlorophenyl)-3-(2,3-dihydrobenzo[b][1,4]dioxin-6-yl)-7-fluoro-1-oxo-1,2,3,4-tetrahydroisoquinolin-4-yl)acetic acid; and 3-(2,3-dihydrobenzo[b][1,4]dioxin-6-yl)-2-(-6-(hydroxymethyl)-5,6,7,8-tetrahydronaphthalen-2-yl)-1-oxo-1,2,3,4-tetrahydroisoquinoline-4-carboxylic acid.

In a variant of the above-embodiment, compounds of the instant invention include the following compounds and their pharmaceutically acceptable salts thereof:

(3S,4S)-2-(4-(tert-butyl)-3-chlorophenyl)-3-(2,3-dihydrobenzo[b][1,4]dioxin-6-yl)-1-oxo-1,2,3,4-tetrahydroisoquinoline-4-carboxylic acid;

(3R,4R)-2-(4-(tert-butyl)-3-chlorophenyl)-3-(2,3-dihydrobenzo[b][1,4]dioxin-6-yl)-1-oxo-1,2,3,4-tetrahydroisoquinoline-4-carboxylic acid;

(3S,4S)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinoline-4-carboxylic acid;

(3R,4R)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinoline-4-carboxylic acid;

(3R,4R)-3-(2,3-dihydro-1,4-benzodioxin-6-yl)-2-[4-(1-methylethyl)phenyl]-1-oxo-1,2,3,4-tetrahydroisoquinoline-4-carboxylic acid;

(3S,4S)-3-(2,3-dihydro-1,4-benzodioxin-6-yl)-2-[4-(1-methylethyl)phenyl]-1-oxo-1,2,3,4-tetrahydroisoquinoline-4-carboxylic acid;

(3R,4R)-3-(2,3-dihydro-1,4-benzodioxin-6-yl)-2-(2,3-dihydro-1H-inden-5-yl)-1-oxo-1,2,3,4-tetrahydroisoquinoline-4-carboxylic acid;

(3S,4S)-3-(2,3-dihydro-1,4-benzodioxin-6-yl)-2-(2,3-dihydro-1-H-inden-5-yl)-1-oxo-1,2,3,4-tetrahydroisoquinoline-4-carboxylic acid;

(3R,4R)-3-(2,3-dihydro-1,4-benzodioxin-6-yl)-2-(4-morpholin-4-ylphenyl)-1-oxo-1,2,3,4-tetrahydroisoquinoline-4-carboxylic acid;

(3S,4S)-3-(2,3-dihydro-1,4-benzodioxin-6-yl)-2-(4-morpholin-4-ylphenyl)-1-oxo-1,2,3,4-tetrahydroisoquinoline-4-carboxylic acid;

(3R,4R)-3-(2,3-dihydro-1,4-benzodioxin-6-yl)-2-[4-(methylsulfonyl)phenyl]-1-oxo-1,2,3,4-tetrahydroisoquinoline-4-carboxylic acid;

(3S,4S)-3-(2,3-dihydro-1,4-benzodioxin-6-yl)-2-[4-(methylsulfonyl)phenyl]-1-oxo-1,2,3,4-tetrahydroisoquinoline-4-carboxylic acid;

(3R,4R)-3-(2,3-dihydro-1,4-benzodioxin-6-yl)-2-[4-(dimethylsulfamoyl)phenyl]-1-oxo-1,2,3,4-tetrahydroisoquinoline-4-carboxylic acid;

(3S,4S)-3-(2,3-dihydro-1,4-benzodioxin-6-yl)-2-[4-(dimethylsulfamoyl)phenyl]-1-oxo-1,2,3,4-tetrahydroisoquinoline-4-carboxylic acid;

(3R,4R)(-2-[4-(1-cyano-1-methylethyl)phenyl]-3-(2,3-dihydro-1,4-benzodioxin-6-yl)-1-oxo-1,2,3,4-tetrahydroisoquinoline-4-carboxylic acid;

(3S,4S) (-2-[4-(1-cyano-1-methylethyl)phenyl]-3-(2,3-dihydro-1,4-benzodioxin-6-yl)-1-oxo-1,2,3,4-tetrahydroisoquinoline-4-carboxylic acid;

(3R,4R)-2-(2-chloropyridin-4-yl)-3-(2,3-dihydro-1,4-benzodioxin-6-yl)-1-oxo-1,2,3,4-tetrahydroisoquinoline-4-carboxylic acid;

(3S,4S)-2-(2-chloropyridin-4-yl)-3-(2,3-dihydro-1,4-benzodioxin-6-yl)-1-oxo-1,2,3,4-tetrahydroisoquinoline-4-carboxylic acid;

(3R,4R)-2-(4-cyclopropylphenyl)-3-(2,3-dihydro-1,4-benzodioxin-6-yl)-oxo-1,2,3,4-tetrahydroisoquinoline-4-carboxylic acid;

(3S,4S)-2-(4-cyclopropylphenyl)-3-(2,3-dihydro-1,4-benzodioxin-6-yl)-1-oxo-1,2,3,4-tetrahydroisoquinoline-4-carboxylic acid;

(3S,4S)-2-[4-(4-acetylpiperazin-1-yl)phenyl]-3-(2,3-dihydro-1,4-benzodioxin-6-yl)-oxo-1,2,3,4-tetrahydroisoquinoline-4-carboxylic acid;

(3R,4R))-2-[4-(4-acetylpiperazin-1-yl)phenyl]-3-(2,3-dihydro-1,4-benzodioxin-6-yl)-1-oxo-1,2,3,4-tetrahydroisoquinoline-4-carboxylic acid;

(3S,4S)-2-[4-(4-acetylpiperazin-1-yl)phenyl]-3-(2,3-dihydro-1,4-benzodioxin-6-yl)-1-oxo-1,2,3,4-tetrahydroisoquinoline-4-carboxylic acid;

(3R,4R)-2-[4-(4-acetylpiperazin-1-yl)phenyl]-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-{4-[1-(2-hydroxyethyl)-1H-pyrazol-4-yl]phenyl}-1-oxo-1,2,3,4-tetrahydroisoquinoline-4-carboxylic acid;

(3R,4R)-3-(2,3-dihydro-1,4-benzodioxin-6-yl)-2-{4-[1-(2-hydroxyethyl)-1H-pyrazol-4-yl]phenyl}-oxo-1,2,3,4-tetrahydroisoquinoline-4-carboxylic acid;

(3S,4S)-2-[4-(difluoromethoxy)phenyl]-3-(2,3-dihydro-1,4-benzodioxin-6-yl)-1-oxo-1,2,3,4-tetrahydroisoquinoline-4-carboxylic acid;

(3R,4R)-2-[4-(difluoromethoxy)phenyl]-3-(2,3-dihydro-1,4-benzodioxin-6-yl)-1-oxo-1,2,3,4-tetrahydroisoquinoline-4-carboxylic acid;

(3S,4S)-2-(1,3-benzothiazol-5-yl)-3-(2,3-dihydro-1,4-benzodioxin-6-yl)-1-oxo-1,2,3,4-tetrahydroisoquinoline-4-carboxylic acid;

(3R,4R)-2-(1,3-benzothiazol-5-yl)-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-(3,3-dimethyl-2-oxo-2,3-dihydro-1H-indol-6-yl)-1-oxo-1,2,3,4-tetrahydroisoquinoline-4-carboxylic acid;

(3R,4R)-3-(2,3-dihydro-1,4-benzodioxin-6-yl)-2-(3,3-dimethyl-2-oxo-2,3-dihydro-1H-indol-6-yl)-1-oxo-1,2,3,4-tetrahydroisoquinoline-4-carboxylic acid;

(3S,4S)-3-(2,3-dihydro-1,4-benzodioxin-6-yl)-1-oxo-2-[4-(1H-pyrazol-5-yl)phenyl]-1,2,3,4-tetrahydroisoquinoline-4-carboxylic acid;

(3R,4R)-3-(2,3-dihydro-1,4-benzodioxin-6-yl)-1-oxo-2-[4-(H-pyrazol-5-yl)phenyl]-1,2,3,4-tetrahydroisoquinoline-4-carboxylic acid;

(3S,4S)-2-(4-chloro-3-fluorophenyl)-3-(2,3-dihydro-1,4-benzodioxin-6-yl)-oxo-1,2,3,4-tetrahydroisoquinoline-4-carboxylic acid;

(3R,4R)-2-(4-chloro-3-fluorophenyl)-3-(2,3-dihydro-1,4-benzodioxin-6-yl)-1-oxo-1,2,3,4-tetrahydroisoquinoline-4-carboxylic acid;

(3S,4S)-2-(4-chloro-3-cyclopropylphenyl)-3-(2,3-dihydro-1,4-benzodioxin-6-yl)-1-oxo-1,2,3,4-tetrahydroisoquinoline-4-carboxylic acid;

(3R,4R)-2-(4-chloro-3-cyclopropylphenyl)-3-(2,3-dihydro-1,4-benzodioxin-6-yl)-1-oxo-1,2,3,4-tetrahydroisoquinoline-4-carboxylic acid;

(3S,4S)-2-(3-cyano-4-morpholin-4-ylphenyl)-3-(2,3-dihydro-1,4-benzodioxin-6-yl)-1-oxo-1,2,3,4-tetrahydroisoquinoline-4-carboxylic acid;

(3R,4R)-2-(3-cyano-4-morpholin-4-ylphenyl)-3-(2,3-dihydro-1,4-benzodioxin-6-yl)-1-oxo-1,2,3,4-tetrahydroisoquinoline-4-carboxylic acid;

(3S,4S)-2-[3-chloro-4-(difluoromethoxy)phenyl]-3-(2,3-dihydro-1,4-benzodioxin-6-yl)-1-oxo-1,2,3,4-tetrahydroisoquinoline-4-carboxylic acid;

(3R,4R)-2-[3-chloro-4-(difluoromethoxy)phenyl]-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-[4-(2-hydroxy-1,1-dimethylethyl)phenyl]-1-oxo-1,2,3,4-tetrahydroisoquinoline-4-carboxylic acid;

(3R,4R)-3-(2,3-dihydro-1,4-benzodioxin-6-yl)-2-[4-(2-hydroxy-1,1-dimethylethyl)phenyl]-1-oxo-1,2,3,4-tetrahydroisoquinoline-4-carboxylic acid;

(3S,4S)-2-(3-chlorophenyl)-3-(2,3-dihydro-1,4-benzodioxin-6-yl)-1-oxo-1,2,3,4-tetrahydroisoquinoline-4-carboxylic acid;

(3R,4R)-2-(3-chlorophenyl)-3-(2,3-dihydro-1,4-benzodioxin-6-yl)-1-oxo-1,2,3,4-tetrahydroisoquinoline-4-carboxylic acid;

(3S,4S)-2-(3-chloro-4-morpholin-4-ylphenyl)-3-(2,3-dihydro-1,4-benzodioxin-6-yl)-1-oxo-1,2,3,4-tetrahydroisoquinoline-4-carboxylic acid;

(3R,4R)-2-(3-chloro-4-morpholin-4-ylphenyl)-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-(2-methylpyridin-4-yl)-1-oxo-1,2,3,4-tetrahydroisoquinoline-4-carboxylic acid;

(3R,4R)-3-(2,3-dihydro-1,4-benzodioxin-6-yl)-2-(2-methylpyridin-4-yl)-1-oxo-1,2,3,4-tetrahydroisoquinoline-4-carboxylic acid;

(3S,4S)-3-(2,3-dihydro-1,4-benzodioxin-6-yl)-1-oxo-2-[4-(2,2,2-trifluoroethoxy)phenyl]-1,2,3,4-tetrahydroisoquinoline-4-carboxylic acid;

(3R,4R)-3-(2,3-dihydro-1,4-benzodioxin-6-yl)-1-oxo-2-[4-(2,2,2-trifluoroethoxy)phenyl]-1,2,3,4-tetrahydroisoquinoline-4-carboxylic acid;

(3S,4S)-2-{4-[(4-chlorophenyl)carbamoyl]phenyl}-3-(2,3-dihydro-1,4-benzodioxin-6-yl)-1-oxo-1,2,3,4-tetrahydroisoquinoline-4-carboxylic acid;

(3R,4R)-2-{4-[(4-chlorophenyl)carbamoyl]phenyl}-3-(2,3-dihydro-1,4-benzodioxin-6-yl)-1-oxo-1,2,3,4-tetrahydroisoquinoline-4-carboxylic acid;

(3S,4S)-2-(4-cyclohexylphenyl)-3-(2,3-dihydro-1,4-benzodioxin-6-yl)-1-oxo-1,2,3,4-tetrahydroisoquinoline-4-carboxylic acid;

(3R,4R)-2-(4-cyclohexylphenyl)-3-(2,3-dihydro-1,4-benzodioxin-6-yl)-1-oxo-1,2,3,4-tetrahydroisoquinoline-4-carboxylic acid;

(3S,4S)-2-[4-(1-cyanocyclohexyl)phenyl]-3-(2,3-dihydro-1,4-benzodioxin-6-yl)-1-oxo-1,2,3,4-tetrahydroisoquinoline-4-carboxylic acid;

(3S,4R)-2-[4-(1-cyanocyclohexyl)phenyl]-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-1-oxo-2-(5,6,7,8-tetrahydronaphthalen-2-yl)-1,2,3,4-tetrahydroisoquinoline-4-carboxylic acid;

(3S,4R)-3-(2,3-dihydro-1,4-benzodioxin-6-yl)-1-oxo-2-(5,6,7,8-tetrahydronaphthalen-2-yl)-1,2,3,4-tetrahydroisoquinoline-4-carboxylic acid;

(3S,4S)-3-(2,3-dihydro-1,4-benzodioxin-6-yl)-2-(2-fluoropyridin-4-yl)-1-oxo-1,2,3,4-tetrahydroisoquinoline-4-carboxylic acid;

(3R,4R)-3-(2,3-dihydro-1,4-benzodioxin-6-yl)-2-(2-fluoropyridin-4-yl)-1-oxo-1,2,3,4-tetrahydroisoquinoline-4-carboxylic acid;

(3S,4S)-3-(2,3-dihydro-1,4-benzodioxin-6-yl)-2-[6-(hydroxymethyl)-5,6,7,8-tetrahydronaphthalen-2-yl]-1-oxo-1,2,3,4-tetrahydroisoquinoline-4-carboxylic acid;

(3R,4R)-3-(2,3-dihydro-1,4-benzodioxin-6-yl)-2-[6-(hydroxymethyl)-5,6,7,8-tetrahydronaphthalen-2-yl]-1-oxo-1,2,3,4-tetrahydroisoquinoline-4-carboxylic acid;

(3S,4S)-2-(2-chloro-6-methylpyridin-4-yl)-3-(2,3-dihydro-1,4-benzodioxin-6-yl)-1-oxo-1,2,3,4-tetrahydroisoquinoline-4-carboxylic acid;

(3R,4R)-2-(2-chloro-6-methylpyridin-4-yl)-3-(2,3-dihydro-1,4-benzodioxin-6-yl)-1-oxo-1,2,3,4-tetrahydroisoquinoline-4-carboxylic acid;

(3S,4S)-2-(4-chloro-3-methylphenyl)-3-(2,3-dihydro-1,4-benzodioxin-6-yl)-1-oxo-1,2,3,4-tetrahydroisoquinoline-4-carboxylic acid;

(3R,4R)-2-(4-chloro-3-methylphenyl)-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-(4-{[(methylsulfonyl)amino]methyl}phenyl)-1-oxo-1,2,3,4-tetrahydroisoquinoline-4-carboxylic acid;

(3R,4R)-3-(2,3-dihydro-1,4-benzodioxin-6-yl)-2-(4-{[(methylsulfonyl)amino]methyl}phenyl)-1-oxo-1,2,3,4-tetrahydroisoquinoline-4-carboxylic acid;

(3S,4S)-3-(2,3-dihydro-1,4-benzodioxin-6-yl)-2-(2,6-dimethylpyridin-4-yl)-1-oxo-1,2,3,4-tetrahydroisoquinoline-4-carboxylic acid;

(3R,4R)-3-(2,3-dihydro-1,4-benzodioxin-6-yl)-2-(2,6-dimethylpyridin-4-yl)-1-oxo-1,2,3,4-tetrahydroisoquinoline-4-carboxylic acid;

(3S,4S)-2-[4-(1-cyanocyclohexyl)phenyl]-3-(2,3-dihydro-1,4-benzodioxin-6-yl)-1-oxo-1,2,3,4-tetrahydroisoquinoline-4-carboxylic acid;

(3R,4R)-2-[4-(1-cyanocyclohexyl)phenyl]-3-(2,3-dihydro-1,4-benzodioxin-6-yl)-1-oxo-1,2,3,4-tetrahydroisoquinoline-4-carboxylic acid;

(3R,4R)-3-(2,3-dihydro-1,4-benzodioxin-6-yl)-1-oxo-2-(5,6,7,8-tetrahydronaphthalen-2-yl)-1,2,3,4-tetrahydroisoquinoline-4-carboxylic acid;

(3S,4S)-3-(2,3-dihydro-1,4-benzodioxin-6-yl)-1-oxo-2-(5,6,7,8-tetrahydronaphthalen-2-yl)-1,2,3,4-tetrahydroisoquinoline-4-carboxylic acid;

(3S,4S)-2-[3-chloro-4-(morpholin-4-ylmethyl)phenyl]-3-(2,3-dihydro-1,4-benzodioxin-6-yl)-1-oxo-1,2,3,4-tetrahydroisoquinoline-4-carboxylic acid;

(3R,4R)-2-[3-chloro-4-(morpholin-4-ylmethyl)phenyl]-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-(3,4-dimethylphenyl)-1-oxo-1,2,3,4-tetrahydroisoquinoline-4-carboxylic acid;

(3R,4R)-3-(2,3-dihydro-1,4-benzodioxin-6-yl)-2-(3,4-dimethylphenyl)-1-oxo-1,2,3,4-tetrahydroisoquinoline-4-carboxylic acid;

(3S,4S)-2-(3,4-dichlorophenyl)-3-(2,3-dihydro-1,4-benzodioxin-6-yl)-1-oxo-1,2,3,4-tetrahydroisoquinoline-4-carboxylic acid;

(3R,4R)-2-(3,4-dichlorophenyl)-3-(2,3-dihydro-1,4-benzodioxin-6-yl)-1-oxo-1,2,3,4-tetrahydroisoquinoline-4-carboxylic acid;

(3S,4S)-2-[4-(benzyloxy)-3-chlorophenyl]-3-(2,3-dihydro-1,4-benzodioxin-6-yl)-1-oxo-1,2,3,4-tetrahydroisoquinoline-4-carboxylic acid;

(3R,4R)-2-[4-(benzyloxy)-3-chlorophenyl]-3-(2,3-dihydro-1,4-benzodioxin-6-yl)-1-oxo-1,2,3,4-tetrahydroisoquinoline-4-carboxylic acid;

(3S,4S)-2-(3-bromophenyl)-3-(2,3-dihydro-1,4-benzodioxin-6-yl)-1-oxo-1,2,3,4-tetrahydroisoquinoline-4-carboxylic acid;

(3R,4R)-2-(3-bromophenyl)-3-(2,3-dihydro-1,4-benzodioxin-6-yl)-1-oxo-1,2,3,4-tetrahydroisoquinoline-4-carboxylic acid;

(3S,4S)-2-(4-cyclopropyl-3-fluorophenyl)-3-(2,3-dihydro-1,4-benzodioxin-6-yl)-1-oxo-1,2,3,4-tetrahydroisoquinoline-4-carboxylic acid;

(3R,4R)-2-(4-cyclopropyl-3-fluorophenyl)-3-(2,3-dihydro-1,4-benzodioxin-6-yl)-1-oxo-1,2,3,4-tetrahydroisoquinoline-4-carboxylic acid;

(3S,4S)-2-[4-(1-cyanocyclohexyl)phenyl]-3-(3,4-dihydro-2H-1,5-benzodioxepin-7-yl)-1-oxo-1,2,3,4-tetrahydroisoquinoline-4-carboxylic acid;

(3R,4R)-2-[4-(1-cyanocyclohexyl)phenyl]-3-(3,4-dihydro-2H-1,5-benzodioxepin-7-yl)-1-oxo-1,2,3,4-tetrahydroisoquinoline-4-carboxylic acid;

(3R,4R)-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

(3S,4S)-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

(3S,4S)-6-bromo-3-(2,3-dihydro-1,4-benzodioxin-6-yl)-2-(2,3-dihydro-1H-inden-5-yl)-1-oxo-1,2,3,4-tetrahydroisoquinoline-4-carboxylic acid;

(3R,4R)-6-bromo-3-(2,3-dihydro-1,4-benzodioxin-6-yl)-2-(2,3-dihydro-1H-inden-5-yl)-1-oxo-1,2,3,4-tetrahydroisoquinoline-4-carboxylic acid;

(3S,4S)-3-(2,3-dihydro-1,4-benzodioxin-6-yl)-2-naphthalen-2-yl-1-oxo-1,2,3,4-tetrahydroisoquinoline-4-carboxylic acid;

(3R,4R)-3-(2,3-dihydro-1,4-benzodioxin-6-yl)-2-naphthalen-2-yl-oxo-1,2,3,4-tetrahydroisoquinoline-4-carboxylic acid;

(3S,4S)-3-(2,3-dihydro-1,4-benzodioxin-6-yl)-1-oxo-2-(3,4,5-trichlorophenyl)-1,2,3,4-tetrahydroisoquinoline-4-carboxylic acid;

(3R,4R)-3-(2,3-dihydro-1,4-benzodioxin-6-yl)-1-oxo-2-(3,4,5-trichlorophenyl)-1,2,3,4-tetrahydroisoquinoline-4-carboxylic acid;

(3S,4S)-2-[3-chloro-4-(1-cyano-1-methylethyl)phenyl]-3-(2,3-dihydro-1,4-benzodioxin-6-yl)-1-oxo-1,2,3,4-tetrahydroisoquinoline-4-carboxylic acid;

(3R,4R)-2-[3-chloro-4-(1-cyano-1-methylethyl)phenyl]-3-(2,3-dihydro-1,4-benzodioxin-6-yl)-1-oxo-1,2,3,4-tetrahydroisoquinoline-4-carboxylic acid;

(3S,4S)-6-bromo-2-(3-chloro-4-methylphenyl)-3-(2,3-dihydro-1,4-benzodioxin-6-yl)-1-oxo-1,2,3,4-tetrahydroisoquinoline-4-carboxylic acid;

(3R,4R)-6-bromo-2-(3-chloro-4-methylphenyl)-3-(2,3-dihydro-1,4-benzodioxin-6-yl)-1-oxo-1,2,3,4-tetrahydroisoquinoline-4-carboxylic acid;

(3S,4S)-7-bromo-2-(3-chloro-4-methylphenyl)-3-(2,3-dihydro-1,4-benzodioxin-6-yl)-1-oxo-1,2,3,4-tetrahydroisoquinoline-4-carboxylic acid;

(3R,4R)-7-bromo-2-(3-chloro-4-methylphenyl)-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-(3,4-dihydro-1H-isochromen-7-yl)-1-oxo-1,2,3,4-tetrahydroisoquinoline-4-carboxylic acid;

(3R,4R)-3-(2,3-dihydro-1,4-benzodioxin-6-yl)-2-(3,4-dihydro-1H-isochromen-7-yl)-1-oxo-1,2,3,4-tetrahydroisoquinoline-4-carboxylic acid;

(3R,4R)-2-(3-chloro-4-cyclohexylphenyl)-3-(2,3-dihydro-1,4-benzodioxin-6-yl)-1-oxo-1,2,3,4-tetrahydroisoquinoline-4-carboxylic acid;

(3S,4S)-2-(3-chloro-4-cyclohexylphenyl)-3-(2,3-dihydro-1,4-benzodioxin-6-yl)-1-oxo-1,2,3,4-tetrahydroisoquinoline-4-carboxylic acid;

(3R,4R)-2-(4-tert-butyl-3-chlorophenyl)-3-(3,4-dihydro-2H-chromen-6-yl)-1-oxo-1,2,3,4-tetrahydroisoquinoline-4-carboxylic acid;

(3S,4S)-2-(4-tert-butyl-3-chlorophenyl)-3-(3,4-dihydro-2H-chromen-6-yl)-1-oxo-1,2,3,4-tetrahydroisoquinoline-4-carboxylic acid;

(3S,4S)-7-bromo-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

(3R,4R)-7-bromo-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

(3S,4S)-2-(4-tert-butyl-3-chlorophenyl)-7-chloro-3-(2,3-dihydro-1,4-benzodioxin-6-yl)-1-oxo-1,2,3,4-tetrahydroisoquinoline-4-carboxylic acid;

(3R,4R)-2-(4-tert-butyl-3-chlorophenyl)-7-chloro-3-(2,3-dihydro-1,4-benzodioxin-6-yl)-1-oxo-1,2,3,4-tetrahydroisoquinoline-4-carboxylic acid;

(3S,4S)-7-(benzyloxy)-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

(3R,4R)-7-(benzyloxy)-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

(3R,4R)-2-(4-tert-butyl-3-chlorophenyl)-3-(2,3-dihydro-1,4-benzodioxin-6-yl)-6-fluoro-1-oxo-1,2,3,4-tetrahydroisoquinoline-4-carboxylic acid;

(3S,4S)-2-(4-tert-butyl-3-chlorophenyl)-3-(2,3-dihydro-1,4-benzodioxin-6-yl)-6-fluoro-1-oxo-1,2,3,4-tetrahydroisoquinoline-4-carboxylic acid;

(3R,4R)-2-(4-tert-butyl-3-chlorophenyl)-3-(2,3-dihydro-1,4-benzodioxin-6-yl)-6-fluoro-1-oxo-1,2,3,4-tetrahydroisoquinoline-4-carboxylic acid;

(3S,4S)-2-(4-tert-butyl-3-chlorophenyl)-3-(2,3-dihydro-1,4-benzodioxin-6-yl)-6-fluoro-1-oxo-1,2,3,4-tetrahydroisoquinoline-4-carboxylic acid;

(3R,4R)-2-(4-tert-butyl-3-chlorophenyl)-7-chloro-3-(2,3-dihydro-1,4-benzodioxin-6-yl)-1-oxo-1,2,3,4-tetrahydroisoquinoline-4-carboxylic acid;

(3S,4S)-2-(4-tert-butyl-3-chlorophenyl)-7-chloro-3-(2,3-dihydro-1,4-benzodioxin-6-yl)-1-oxo-1,2,3,4-tetrahydroisoquinoline-4-carboxylic acid;

(3R,4R)-2-(4-tert-butyl-3-chlorophenyl)-3-(4-methyl-3,4-dihydro-2H-1,4-benzoxazin-6-yl)-1-oxo-1,2,3,4-tetrahydroisoquinoline-4-carboxylic acid;

(3S,4S)-2-(4-tert-butyl-3-chlorophenyl)-3-(4-methyl-3,4-dihydro-2H-1,4-benzoxazin-6-yl)-1-oxo-1,2,3,4-tetrahydroisoquinoline-4-carboxylic acid;

(3R,4R)-2-(4-tert-butyl-3-chlorophenyl)-3-(4-methyl-3,4-dihydro-2H-1,4-benzoxazin-6-yl)-1-oxo-1,2,3,4-tetrahydroisoquinoline-4-carboxylic acid;

(3S,4S)-2-(4-tert-butyl-3-chlorophenyl)-3-(4-methyl-3,4-dihydro-2H-1,4-benzoxazin-6-yl)-1-oxo-1,2,3,4-tetrahydroisoquinoline-4-carboxylic acid;

(3S,4S)-2-(4-tert-butyl-3-chlorophenyl)-3-(2,3-dihydro-1,4-benzodioxin-6-yl)-7-hydroxy-1-oxo-1,2,3,4-tetrahydroisoquinoline-4-carboxylic acid;

(3R,4R)-2-(4-tert-butyl-3-chlorophenyl)-3-(2,3-dihydro-1,4-benzodioxin-6-yl)-7-hydroxy-1-oxo-1,2,3,4-tetrahydroisoquinoline-4-carboxylic acid;

(3S,4S)-2-[3-chloro-4-(1-cyanocyclopropyl)phenyl]-3-(2,3-dihydro-1,4-benzodioxin-6-yl)-1-oxo-1,2,3,4-tetrahydroisoquinoline-4-carboxylic acid;

(3R,4R)-2-[3-chloro-4-(1-cyanocyclopropyl)phenyl]-3-(2,3-dihydro-1,4-benzodioxin-6-yl)-1-oxo-1,2,3,4-tetrahydroisoquinoline-4-carboxylic acid;

(3R,4R)-2-[3-chloro-4-(1-cyanocyclopropyl)phenyl]-3-(2,3-dihydro-1,4-benzodioxin-6-yl)-1-oxo-1,2,3,4-tetrahydroisoquinoline-4-carboxylic acid;

(3S,4S)-2-[3-chloro-4-(1-cyanocyclopropyl)phenyl]-3-(2,3-dihydro-1,4-benzodioxin-6-yl)-1-oxo-1,2,3,4-tetrahydroisoquinoline-4-carboxylic acid;

(3R,4R)-2-(4'-acetamido-[1,1'-biphenyl]-4-yl)-3-(2,3-dihydrobenzo[b][1,4]dioxin-6-yl)-1-oxo-1,2,3,4-tetrahydroisoquinoline-4-carboxylic acid;

(3S,4S)-2-(4'-acetamido-[1,1'-biphenyl]-4-yl)-3-(2,3-dihydrobenzo[b][1,4]dioxin-6-yl)-1-oxo-1,2,3,4-tetrahydroisoquinoline-4-carboxylic acid;

(3S,4S)-2-[4-(1-acetylpiperidin-4-yl)phenyl]-3-(2,3-dihydro-1,4-benzodioxin-6-yl)-1-oxo-1,2,3,4-tetrahydroisoquinoline-4-carboxylic acid;

(3R,4R)-2-[4-(1-acetylpiperidin-4-yl)phenyl]-3-(2,3-dihydro-1,4-benzodioxin-6-yl)-1-oxo-1,2,3,4-tetrahydroisoquinoline-4-carboxylic acid;

(3R,4R)-2-(4'-acetamido-2-chloro-[1,1'-biphenyl]-4-yl)-3-(2,3-dihydrobenzo[b][1,4]dioxin-6-yl)-1-oxo-1,2,3,4-tetrahydroisoquinoline-4-carboxylic acid;

(3S,4S)-2-(4'-acetamido-2-chloro-[1,1'-biphenyl]-4-yl)-3-(2,3-dihydrobenzo[b][1,4]dioxin-6-yl)-1-oxo-1,2,3,4-tetrahydroisoquinoline-4-carboxylic acid;

(3S,4S)-2-(4-(tert-butyl)-3-chlorophenyl)-3-(2,3-dihydrobenzo[b][1,4]dioxin-6-yl)-N-methyl-1-oxo-1,2,3,4-tetrahydroisoquinoline-4-carboxamide;

(3R,4R)-2-(4-(tert-butyl)-3-chlorophenyl)-3-(2,3-dihydrobenzo[b][1,4]dioxin-6-yl)-N-methyl-1-oxo-1,2,3,4-tetrahydroisoquinoline-4-carboxamide;

(3S,4S)-2-(4-tert-butyl-3-chlorophenyl)-3-(2,3-dihydro-1,4-benzodioxin-6-yl)-1-oxo-1,2,3,4-tetrahydroisoquinoline-4-carboxamide;

(3R,4R)-2-(4-tert-butyl-3-chlorophenyl)-3-(2,3-dihydro-1,4-benzodioxin-6-yl)-1-oxo-1,2,3,4-tetrahydroisoquinoline-4-carboxamide;

(3S,4S)-2-(4-tert-butyl-3-chlorophenyl)-3-(2,3-dihydro-1,4-benzodioxin-6-yl)-N,N-dimethyl-1-oxo-1,2,3,4-tetrahydroisoquinoline-4-carboxamide;

(3R,4R)-2-(4-tert-butyl-3-chlorophenyl)-3-(2,3-dihydro-1,4-benzodioxin-6-yl)-N,N-di methyl-1-oxo-1,2,3,4-tetrahydroisoquinoline-4-carboxamide;

(3S,4S)-2-(4-tert-butyl-3-chlorophenyl)-3-(2,3-dihydro-1,4-benzodioxin-6-yl)-7-fluoro-1-oxo-1,2,3,4-tetrahydroisoquinoline-4-carboxamide;

(3R,4R)-2-(4-tert-butyl-3-chlorophenyl)-3-(2,3-dihydro-1,4-benzodioxin-6-yl)-7-fluoro-1-oxo-1,2,3,4-tetrahydroisoquinoline-4-carboxamide;

(3S,4S)-2-(4-(tert-butyl)-3-chlorophenyl)-3-(2,3-dihydrobenzo[b][1,4]dioxin-6-yl)-1-oxo-7-vinyl-1,2,3,4-tetrahydroisoquinoline-4-carboxylic acid;

(3R,4R)-2-(4-(tert-butyl)-3-chlorophenyl)-3-(2,3-dihydrobenzo[b][1,4]dioxin-6-yl)-1-oxo-7-vinyl-1,2,3,4-tetrahydroisoquinoline-4-carboxylic acid;

(3R,4R)-2-(4-(tert-butyl)-3-chlorophenyl)-3-(2,3-dihydrobenzo[b][1,4]dithiin-6-yl)-1-oxo-1,2,3,4-tetrahydroisoquinoline-4-carboxylic acid;

(3S,4S)-2-(4-(tert-butyl)-3-chlorophenyl)-3-(2,3-dihydrobenzo[b][1,4]dithiin-6-yl)-1-oxo-1,2,3,4-tetrahydroisoquinoline-4-carboxylic acid;

(3R,4R)-2-(4-(tert-butyl)-3-chlorophenyl)-3-(2,3-dihydrobenzo[b][1,4]oxathiin-6-yl)-1-oxo-1,2,3,4-tetrahydroisoquinoline-4-carboxylic acid;

(3S,4S)-2-(4-(tert-butyl)-3-chlorophenyl)-3-(2,3-dihydrobenzo[b][1,4]oxathiin-6-yl)-1-oxo-1,2,3,4-tetrahydroisoquinoline-4-carboxylic acid;

(3R,4R)-2-(4-(tert-butyl)-3-chlorophenyl)-3-(2,3-dihydrobenzo[b][1,4]oxathiin-7-yl)-1-oxo-1,2,3,4-tetrahydroisoquinoline-4-carboxylic acid;

(3S,4S)-2-(4-(tert-butyl)-3-chlorophenyl)-3-(2,3-dihydrobenzo[b][1,4]oxathiin-7-yl)-1-oxo-1,2,3,4-tetrahydroisoquinoline-4-carboxylic acid;

(3R,4R)-2-(4-(tert-butyl)-3-chlorophenyl)-3-(2,3-dihydrobenzo[b][1,4]dioxin-6 yl)-N hydroxy-1-oxo-1,2,3,4-tetrahydroisoquinoline-4-carboxamide;

(3S,4S)-2-(4-(tert-butyl)-3-chlorophenyl)-3-(2,3-dihydrobenzo[b][1,4]dioxin-6-yl)-N-hydroxy-1-oxo-1,2,3,4-tetrahydroisoquinoline-4-carboxamide;

(3S,4S)-2-(4-(tert-butyl)-3-chlorophenyl)-3-(chroman-6-yl)-1-oxo-1,2,3,4-tetrahydroisoquinoline-4-carboxylic acid;

(3R,4R)-2-(4-(tert-butyl)-3-chlorophenyl)-3-(chroman-6-yl)-1-oxo-1,2,3,4-tetrahydroisoquinoline-4-carboxylic acid;

(3S,4S)-2-(4-(tert-butyl)-3-chlorophenyl)-3-(3,4-dihydro-2H-benzo[b][1,4]oxazin-6-yl)-1-oxo-1,2,3,4-tetrahydroisoquinoline-4-carboxylic acid;

(3R,4R)-2-(4-(tert-butyl)-3-chlorophenyl)-3-(3,4-dihydro-2H-benzo[b][1,4]oxazin-6-yl)-1-oxo-1,2,3,4-tetrahydroisoquinoline-4-carboxylic acid;

(3S,4S)-2-(4-(tert-butyl)-3-chlorophenyl)-3-(4-isopropyl-3,4-dihydro-2H-benzo[b][1,4]oxazin-6-yl)-1-oxo-1,2,3,4-tetrahydroisoquinoline-4-carboxylic acid;

(3R,4R)-2-(4-(tert-butyl)-3-chlorophenyl)-3-(4-isopropyl-3,4-dihydro-2H-benzo[b][1,4]oxazin-6-yl)-1-oxo-1,2,3,4-tetrahydroisoquinoline-4-carboxylic acid;

(3S,4S)-2-(4-(tert-butyl)-3-chlorophenyl)-3-(3-cyclopropyl-2,3-dihydrobenzo[b][1,4]dioxin-6-yl)-7-fluoro-1-oxo-1,2,3,4-tetrahydroisoquinoline-4-carboxylic acid;

(3R,4R)-2-(4-(tert-butyl)-3-chlorophenyl)-3-(3-cyclopropyl-2,3-dihydrobenzo[b][1,4]dioxin-6-yl)-7-fluoro-1-oxo-1,2,3,4-tetrahydroisoquinoline-4-carboxylic acid;

(3S,4S)-2-(4-(tert-butyl)-3-chlorophenyl)-3-(2,3-dihydrobenzo[b][1,4]oxathiin-6-yl)-7-fluoro-1-oxo-1,2,3,4-tetrahydroisoquinoline-4-carboxylic acid;

(3R,4R)-2-(4-(tert-butyl)-3-chlorophenyl)-3-(2,3-dihydrobenzo[b][1,4]oxathiin-6-yl)-7-fluoro-1-oxo-1,2,3,4-tetrahydroisoquinoline-4-carboxylic acid;

2-((3S,4S)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinolin-4-yl)acetic acid;

2-((3R,4R)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinolin-4-yl)acetic acid;

(3R,4R)-3-(2,3-dihydrobenzo[b][1,4]dioxin-6-yl)-2-((S)-6-(hydroxymethyl)-5,6,7,8-tetrahydronaphthalen-2-yl)-1-oxo-1,2,3,4-tetrahydroisoquinoline-4-carboxylic acid;

(3R,4R)-3-(2,3-dihydrobenzo[b][1,4]dioxin-6-yl)-2-((R)-6-(hydroxymethyl)-5,6,7,8-tetrahydronaphthalen-2-yl)-1-oxo-1,2,3,4-tetrahydroisoquinoline-4-carboxylic acid;

(3S,4S)-3-(2,3-dihydrobenzo[b][1,4]dioxin-6-yl)-2-((S)-6-(hydroxymethyl)-5,6,7,8-tetrahydronaphthalen-2-yl)-1-oxo-1,2,3,4-tetrahydroisoquinoline-4-carboxylic acid; and (3S,4S)-3-(2,3-dihydrobenzo[b][1,4]dioxin-6-yl)-2-((R)-6-(hydroxymethyl)-5,6,7,8-tetrahydronaphthalen-2-yl)-1-oxo-1,2,3,4-tetrahydroisoquinoline-4-carboxylic acid.

The invention also encompasses pharmaceutical compositions containing a compound of formula I, and methods for treatment or prevention of STING mediated diseases using compounds of formula I.

One aspect of the present invention is to provide compounds that can inhibit the biological activity of STING. Another aspect of the invention is to provide methods of selectively modulating human STING activity and thereby promoting medical treatment of diseases mediated by STING dysfunction.

In one embodiment of the invention, the compounds of formula I inhibit STING activity in biochemical and cell-based assays and exhibit therapeutic activity in medical conditions in which STING activity is excessive or undesirable.

The invention is described using the following definitions unless otherwise indicated.

When any variable (e.g. aryl, heteroaryl, $R^1$, $R^5$, etc.) occurs more than one time in any constituent, its definition on each occurrence is independent at every other occurrence. Also, combinations of substituents/or variables are permissible only if such combinations result in stable compounds.

The wavy line ~~~ , as used herein, indicates a point of attachment to the rest of the compound.

Lines drawn into the ring systems, such as, for example:

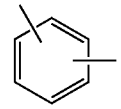

indicate that the indicated line (bond) may be attached to any of the substitutable ring carbon atoms. The term "alkyl," as used herein, refers to an aliphatic hydrocarbon group having one of its hydrogen atoms replaced with a bond. An alkyl group may be straight or branched and contain from about 1 to about 10 carbon atoms. In different embodiments, an alkyl group contains from 1 to 6 carbon atoms ($C_{1-6}$ alkyl) or from about 1 to about 3 carbon atoms ($C_{1-3}$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl In one embodiment, an alkyl group is linear. In another embodiment, an alkyl group is branched. Unless otherwise indicated, an alkyl group is unsubstituted.

The term "alkoxy" represents a linear or branched alkyl group of indicated number of carbon atoms attached through an oxygen bridge.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH)CH_3$.

"Aminoalkyl" refers to an alkyl group as described above in which one hydrogen atom has been replaced by an amino (—NH₂), monoalkylamino or dialkylamino group. Examples include CH₂NH₂, CH₂CH₂NHCH₃ and CH(N(CH₃)₂)CH₃.

The term "$C_0$" as employed in expressions such as "$C_{0-6}$alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

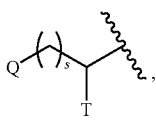

wherein s is an integer equal to zero, 1 or 2, the structure is

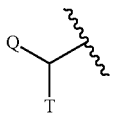

when s is zero.

The term "halogen" or "halo") refers to fluorine, chlorine, bromine and iodine (alternatively referred to as fluoro (F), chloro (Cl), bromo (Br), and iodo (I)).

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl. In one embodiment, an aryl group contains from about 6 to about 10 carbon atoms. In one embodiment, an aryl group can be optionally fused to a cycloalkyl or cycloalkanoyl. Non-limiting examples of aryl groups include phenyl and naphthyl. In one embodiment, an aryl group is phenyl. Unless otherwise indicated, an aryl group is unsubstituted.

"Carboxy" refers to the functional group —C(O)OR, for example: ethylcarboxy is

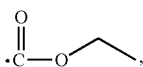

phenylcarboxy is

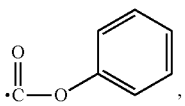

and cyclopropycarboxy is

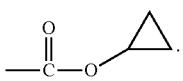

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound.

"Cycloalkyl" or "$C_{12}$ cycloalkyl" means any univalent radical derived from a monocyclic or bicyclic ring system having 3 to 12 ring carbons atoms; said ring system may be (a) a $C_3$ to a $C_8$ monocyclic, saturated ring, or (b) a bicyclic saturated ring. Here, the point of attachment for a "cycloalkyl" to the rest of the molecule is on the saturated ring. For a bicyclic system, with (b), the rings are fused across two adjacent ring carbon atoms (e.g., decalin), or are bridged groups (e.g., norbornane). Additional examples within the above meaning include, but are not limited to univalent radicals of cyclopropane, cyclobutane, cyclopentane, cyclohexane, decalin, bicyclo[2.2.2]octane and 3a,5,6,7-tetrahydro-4H-indene.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl" "$C_{3-6}$ cycloalkyl", "$C_{5-7}$ cycloalkyl" and the like have analogous meanings.

The term "heteroaryl," as used herein, refers to an aromatic monocyclic ring comprising about 5 to about 7 ring atoms, wherein from 1 to 4 of the ring atoms are independently O, N or S and the remaining ring atoms are carbon atoms. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, pyrrolyl, triazolyl, 1,2,4-thiadiazolyl, pyridinyl, pyrazinyl, pyridazinyl, imidazolyl, and the like, and all isomeric forms thereof. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, or N, and the remainder of the ring atoms are carbon atoms. A heterocycloalkyl group can be joined via a ring carbon or ring nitrogen atom. Said ring system may be (a) a saturated monocyclic ring or a partially unsaturated ring, or (b) a bicyclic saturated carbocycle. For a bicyclic system, within either (a) or (b), the rings are fused across two adjacent ring carbon atoms (e.g., decahydroisoquinoline), at one ring carbon atom (e.g., spiro[2.4]heptyl, spiro[2.2]pentane), or are bridged groups (e.g., 2,5-diazabicyclo[2.2.1]heptyl).

In one embodiment, a heterocycloalkyl group is monocyclic and has from about 3 to about 7 ring atoms. In another embodiment, a heterocycloalkyl group is monocyclic has from about 5 to about 8 ring atoms. In another embodiment, a heterocycloalkyl group is bicyclic and has from about 8 to about 11 ring atoms. In still another embodiment, a heterocycloalkyl group is monocyclic and has 5 or 6 ring atoms.

In one embodiment, a heterocycloalkyl group is monocyclic. In another embodiment, a heterocycloalkyl group is bicyclic. There are no adjacent oxygen and/or sulfur atoms present in the ring system. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

"Haloalkyl" refers to an alkyl group as described above wherein one or more (in particular 1 to 5) hydrogen atoms have been replaced by halogen atoms, with up to complete substitution of all hydrogen atoms with halo groups. Cr haloalkyl, for example, includes —CF$_3$, —CF$_2$CF$_3$, —CHFCH$_3$, and the like.

"Hydroxyalkyl" refers to an alkyl group as described above in which one or more (in particular 1 to 3) hydrogen atoms have been replaced by hydroxy groups. Examples include CH$_2$OH, CH$_2$CHOH and CHOHCH$_3$.

The term "sulfamoyl" is a suffix to denote radicals derived from sulfamide such as —SO$_2$NH$_2$, —SO$_2$NHR and —SO$_2$N(RR$_1$).

"Sulfanyl" refers to mercapto radical, —SH. For example, methylsulfanyl is —SCH$_3$.

"Sulfonyl" refers to —S(=O)$_2$R. For example, —S(=O)$_2$H, methylsulfonyl (—S(=O)$_2$CH$_3$), or cyclopropylsulfonyl

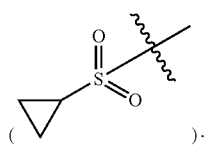
( ).

Unless expressly stated to the contrary, an "unsaturated" ring is a partially or fully unsaturated ring. For example, an "unsaturated monocyclic C$_{1-6}$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

Structural representations of compounds having substituents terminating with a methyl group may display the terminal methyl group either using the characters "CH$_3$", e.g. "—CH$_3$" or using a straight line representing the presence of the methyl group, e.g. " —— ", i.e.

and

have equivalent meanings.

For variable definitions containing terms having repeated terms, e.g., (CR$_i$R$_j$)$_r$, where r is the integer 2, R$_i$ is a defined variable, and R$_j$ is a defined variable, the value of R$_i$ may differ in each instance in which it occurs, and the value of R may differ in each instance in which it occurs. For example, if R$_i$ and R$_j$ are independently selected from the group consisting of methyl, ethyl, propyl and butyl, then (CR$_i$R$_j$)$_2$ can be

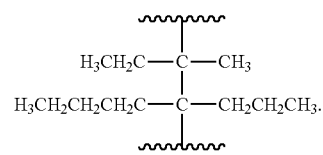

In one embodiment of the invention, R$_1$ is selected from —OH, amino, —NHOH, —N(C$_{1-3}$ alkyl)$_2$, and —N(C$_{1-3}$alkyl) and the other groups are provided in the general formula I.

In a second embodiment of the invention, R$_1$ is selected from -OH, amino, —NHOH, dimethylamino, diethylamino, dipropylamino, methylamino, ethylamino, and propylamino and the other groups are provided in the general formula I above.

In a third embodiment of the invention, R$_1$ is selected from —OH, amino, —NHOH, dimethylamino, and methylamino, and the other groups are provided in the general formula I above.

In a fourth embodiment, n is 0, 1, or 2, and the other groups are provided in general formula I above or or as in the first through third embodiments.

In a fifth embodiment, n is 0, or 1, and the other groups are provided in general formula I above or or as in the first through third embodiments.

In a sixth embodiment of the disclosure, z is 0, 1, or 2, and the other groups are provided in general formula I above or or as in the first through fifth embodiments.

In a seventh embodiment, z is 0, or 1, and the other groups are provided in general formula I above or or as in the first through fifth embodiments.

In a eighth embodiment of the disclosure, z is 0, 1, or 2, and the other groups are provided in general formula I above or as in the first through seventh embodiments.

In a ninth embodiment, z is 0, or 1, and the other groups are provided in general formula I above or or as in the first through seventh embodiments.

In a tenth embodiment of the disclosure, each R$_3$ is independently selected from C$_{1-6}$ alkyl, C$_{1-6}$haloalkyl, (C$_{3-7}$cycloakylC$_{0-6}$alkyl, and C$_{3-7}$heterocycloalkylC$_{0-6}$alkyl and the other groups are provided in general formula I above or as in the first through ninth embodiments.

In an eleventh embodiment of the disclosure, each R$_3$ is independently selected from C$_{1-6}$ alkyl and C$_{3-7}$-cycloalkyl$C_{0-6}$alkyl, and the other groups are provided in general formula I above or as in the first through ninth embodiments.

In a twelfth embodiment of the invention, each $R_3$ is independently selected from methyl, isopropyl, and cyclopropyl, and the other groups are provided in general formula I above or as in the first through ninth embodiments.

In a thirteenth embodiment of the disclosure, each $R_4$ is independently selected from halogen, hydroxy, $C_{2-10}$ alkenyl, and aryl($C_{0-10}$ alkyl)oxy($C$)$_{0-10}$ alkyl), and the other groups are provided in general formula I above or as in the first through twelfth embodiments.

In a fourteenth embodiment of the disclosure, each $R_4$ is independently selected from halogen, hydroxy, $C_{2-6}$ alkenyl, and aryl($C_{0-10}$alkyl)oxy, and the other groups are provided in general formula I above or as in the first through twelfth embodiments.

In a fifteenth embodiment, each $R_4$ is independently selected from halogen, hydroxy, ethenyl, and phenylmethoxy, and the other groups are provided in general formula I above or as in the first through twelfth embodiments.

In a sixteenth embodiment of the disclosure, each $R_5$ is independently selected from: halogen, $C_{1-10}$ alkyl(oxy)$_{0-1}C_{0-10}$ alkyl, $C_{0-10}$ heteroalkyl(oxy)$_{0-1}C_{0-10}$ alkyl, $C_{2-10}$ alkenyl(oxy)$_{0-1}$ $C_{0-10}$ alkyl, aryl $C_{0-10}$ alkyl(oxy)$_{0-1}C_{0-10}$ alkyl, $C_{3-12}$ cycloalkyl $C_{0-10}$ alkyl(oxy)$_{0-1}C_{0-10}$ alkyl, heteroaryl $C_{0-10}$ alkyl(oxy)$_{0-1}C_{0-10}$ alkyl, ($C_{3-12}$)heterocycloalkyl $C_{0-10}$ alkyl(oxy)$_{0-1}C_{0-10}$ alkyl, amino, $C_{1-10}$ alkylamino$C_{0-10}$ alkyl, aryl $C_{0-10}$ alkylamino (carbonyl)$C_{0-10}$ alkyl, $C_{1-10}$ alkylsulfonyl$C_{0-10}$ alkyl, $C_{1-10}$ alkylsulfonylamino$C_{0-10}$ alkyl, ($C_{1-10}$ alkyl)$_{1-2}$ amino, —SO$_2$NH$_2$, —SO$_2$NH($C_{1-10}$ alkyl), —SO$_2$N($C_{1-10}$ alkyl)$_2$, —SH, —S($C_{1-10}$ alkyl), —NH=CH$_2$, hydroxy, —($C_{1-10}$ alkyl)OR, —$C_{0-10}$ alkylalkoxy, cyano, —($C_{1-6}$alkyl)cyano, and $C_{1-6}$haloalkyl(oxy)$_{0-1}$; wherein each $R_5$ is substituted with 0, 1, 2, or 3 $R_6$ substituents, and the other groups are provided in general formula I above or as in the first through fifteenth embodiments.

In a seventeenth embodiment, each $R_5$ is independently selected from: halogen, $C_{1-6}$ alkyl(oxy)$_{0-1}C_{0-10}$ alkyl, $C_{2-10}$ alkenyl, aryl $C_{0-10}$ alkyl(oxy)$_{0-1}C_{0-10}$ alkyl, $C_{3-2}$ cycloalkyl $C_{0-10}$ alkyl, heteroaryl $C_{0-10}$ alkyl, ($C_{3-12}$) heterocycloalkyl $C_{0-10}$ alkyl, $C_{1-10}$ alkylamino$C_{0-10}$ alkyl, aryl $C_{0-10}$ alkylamino (carbonyl)$C_{0-10}$ alkyl, $C_{1-10}$ alkylsulfonyl$C_{0-10}$ alkyl, $C_{1-10}$ alkylsulfonylamino $C_{0-10}$ alkyl, ($C_{1-10}$ alkyl)$_{1-2}$ amino, —SO$_2$NH ($C_{1-10}$ alkyl), —SO$_2$N($C_{1-10}$ alkyl)$_2$, —SH, —NH=CH$_2$, —($C_{1-10}$ alkyl)OH, —$C_{0-10}$ alkylalkoxy, cyano, —($C_{1-6}$alkyl)cyano, and $C_{1-6}$haloalkyl(oxy)$_{0-1}$; wherein each $R_5$ is substituted with 0, 1, 2, or 3 $R_6$ substituents, and the other groups are provided in general formula I above or as in the first through fifteenth embodiments.

In an eighteenth embodiment, each $R_5$ is independently selected from: F, Cl, tert-butyl, isopropyl, methyl, ethyl, morpholinyl, methylsufonyl, dimethysulfamoyl, 1-cyano-1-methylethyl, cyclopropyl, piperazinyl, pyrazolyl, methoxy, —SH, —N=CH$_2$, methylamino, cyano, hydroxyethyl, 2,2,2-trifluoroethyloxy, phenylaminocarbonyl, cyclohexyl, propyl, ((methylsulfonyl)amino)methyl, morpholinylmethyl, phenylethyloxy (benzyloxy), Br, prop-2-enyl, hydroxymethyl, phenyl, and piperidinyl, wherein each $R_5$ is substituted with 0, 1 or 2 $R_6$ substituents, and the other groups are provided in general formula I above or as in the first through fifteenth embodiments.

In a nineteenth embodiment of the disclosure, each $R_6$ is independently selected from halogen, cyano, oxo, $C_{1-6}$ alkylcarbonyl, $C_{1-6}$ alkyl, $C_{1-6}$ alkylcarbonylamino, and —($C_{1-10}$ alkyl)OH, and the other groups are provided in general formula I above or as in the first through eighteenth embodiments.

In a twentieth embodiment of the invention, each R is independently selected from halogen, methylcarbonyl, hydroxyethyl, oxo, cyano, hydroxymethyl, methylcarbonyl amino, and methyl, and the other groups are provided in general formula I above or as in the first through eighteenth embodiments.

In a twenty-first embodiment of the disclosure,

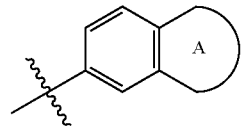

is selected from:

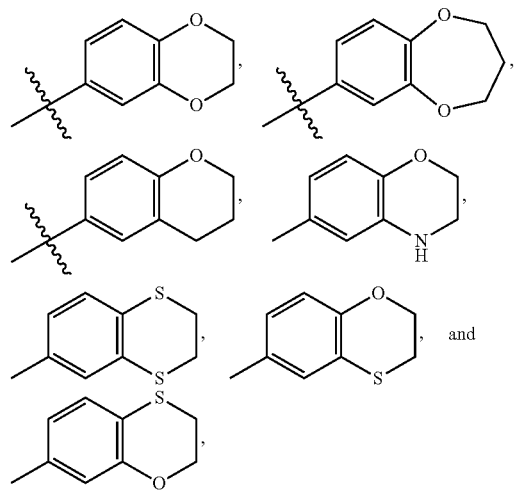

and the other groups are provided in general formula I above or as in the first through twentieth embodiments.

In a twenty-second embodiment of the invention,

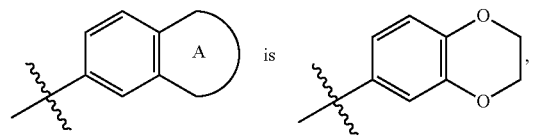

and the other groups are provided in general formula I above or as in the first through twentieth embodiments.

"Patient" for the purposes of the present invention includes humans and other animals, particularly mammals and other organisms. Thus the methods are applicable to both human therapy and veterinary applications.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —$(CR_3R_3)_2$—, each occurrence of the two R groups may be the same or different. As used herein, unless explicitly stated to the contrary, each reference to a specific compound of the present invention or a generic formula of compounds of the present invention is intended to include the compound(s) as well as pharmaceutically acceptable salts thereof.

Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers.

Optical Isomers-Diastereomers-Geometric Isomers-Tautomers

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereometric compound is named using an "and" in the stereometric designation, for example, (3S,4S) and (3R,4R)-3-(2,3-dihydro-1,4-benzodioxin-6-yl)-2-(3,3-dimethyl-2-oxo-2,3-dihydro-1H-indol-6-yl)-1-oxo-1,2,3,4-tetrahydroisoquinoline-4-carboxylic acid, the "and" indicates a racemic mixture of the enantiomers. That is, the individual enantiomers were not individually isolated.

When the stereometric nomenclature includes "or", for example, (3S,4S) or (3R,4R)-2-[4-(1-cyanocyclohexyl)phenyl]-3-(2,3-dihydro-1,4-benzodioxin-6-yl)-1-oxo-1,2,3,4-tetrahydroisoquinoline-4-carboxylic acid, the "or" indicates that chiral resolution of racemate into individual enantiomers was accomplished but the actual optical activity of the specific enantiomer was not determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

Diastereomeric mixtures can be separated into their individual diastereomers on the basis of their physical chemical differences by methods well known to those skilled in the art, such as, for example, by chromatography (e.g. chiral HPLC column) and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride ((2R)-3,3,3-trifluoro-2-methoxy-2-phenylpropanoyl chloride), separating the diastereomers and converting (e.g., hydrolyzing) the individual diastereomers to the corresponding pure enantiomers. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I, subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$) cycloalkyl, benzyl, or R-carbonyl is a natural α-aminoacyl or natural α-aminoacyl, C(OH)C(O)OY$^1$ wherein Y$^1$ is H, ($C_1$-$C_6$)alkyl or benzyl, C(OY$^2$)Y$^3$ wherein Y$^2$ is ($C_1$-$C_4$) alkyl and Y$^3$ is ($C_1$-$C_6$)alkyl, carboxy ($C_1$-$C_6$) alkyl, amino($C_1$-$C_4$)alkyl or mono-N- or di-N,N—($C_1$-$C_6$) alkylaminoalkyl, —C(Y$^4$)Y$^5$ wherein Y$^4$ is H or methyl and Y$^5$ is mono-N- or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et a, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Additionally, the present invention is meant to include in compounds of generic Formula I, all suitable replacements of sp3 orbital carbons to sp3 Si as can readily be envisioned by one of ordinary skill in the art.

Utilities

Compounds of the Invention have activity for STING. Compounds of this invention have been tested using the assays described in the Biological Examples and have been determined to be inhibitors of STING. Suitable in vitro assays for measuring STING activity and the inhibition thereof by compounds are known in the art. For further details of an in vitro assay for measuring STING activity, see the Biological Examples herein. Cell-based assays for measurement of in vitro efficacy in treatment of cancer are known in the art. In addition, assays are described in the Biological Examples provided herein.

Compounds of Formula I may be useful for treating diseases, including autoimmune disorders, inflammatory diseases, and cancers, which are listed below.

Cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannomas, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplasia syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Autoimmune diseases: Hashimoto's thyroiditis, systemic lupus erythematosus (SLE), Goodpasture's syndrome, pemphigus, receptor autoimmune diseases, Basedow's disease (Graves' disease), myasthemia gravis, insulin resistant diseases, autoimmune hemolytic anemia, autoimmune thrombocytopenic purpura, autoimmune encephalomyelitis, rheumatism, rheumatoid arthritis, scleroderma, mixed connective tissue disease, polymyositis, pernicious anemia, idiopathic Addison's disease, some types of infertility, glomerulonephritis, bullous pemphigus, Sjogren's syndrome, some types of diabetes, adrenergic agent resistance, chronic active hepatitis, primary biliary cirrhosis, endocrine failure, vitiligo, angiitis, post-cardiac surgery syndrome, urticaria, atopic dermatiti and multiple sclerosis, autoimmune polyglandular disease (also known as autoimmune polyglandular syndrome), autoimmune alopecia; pernicious anemia; vitiligo; autoimmune hypopituatarism, and Guillain-Barre syndrome.

Inflammatory Diseases: asthma, allergic rhinitis, psoriasis, inflammatory arthritis, rheumatoid arthritis, psoriatic arthritis or osteoarthritis, irritable bowel syndrome, ulcerative colitis, Crohn's disease, respiratory allergies (asthma, hay fever, allergic rhinitis) or skin allergies, scleracierma, mycosis fungoides, acute inflammatory responses (such as acute respiratory distress syndrome and ishchemia/reperfusion injury), dermatomyositis, alopecia greata, chronic actinic dermatitis, eczema, Behcet's disease, Pustulosis palmoplanteris, Pyoderma gangrenum, Sezary's syndrome, atopic dermatitis, systemic sclerosis, and morphea.

Central Nervous System Disorders: Multiple sclerosis, schizophrenia and Alzheimer's disease.

Thus, in one embodiment, the invention provides a method of inhibiting STING activation comprising binding to STING with an effective amount of a compound as disclosed herein.

In another embodiment, the invention provides a method of treating a STING modulated disease comprising administering to a mammal in need of such treatment a therapeutically effective amount of a compound as disclosed herein.

In another embodiment, the invention provides a method of treating cancer disease mediated by STING comprising administering to a mammal in need of such treatment a therapeutically effective amount of a compound as disclosed herein.

Compounds of the invention may also useful as inhibitors of STING in vivo for studying the in vivo role of STING in biological processes, including the diseases described herein. Accordingly, the invention also comprises a method of inhibiting STING in vivo comprising administering a compound or composition of the invention to a mammal.

Accordingly, another aspect of the present invention provides a method for the treatment or prevention of a STING mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a STING mediated diseases or disorders.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 milligram of active agent per kilogram body weight of a mammal (mg/kg) to about 100 mg/kg, typically, between 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.01 mg to 10 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, 400 mg, or 500 mg.

The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of the disease state. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be preferred for continuous infusion.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or *arachis* oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

In certain embodiments, a compound of Formula I is combined in a pharmaceutical combination formulation, or dosing regimen as combination therapy, with one or more other therapeutic agents that has anti-inflammatory or anti-hyperproliferative properties or that is useful for treating an inflammation, immune-response disorder, or hyperproliferative disorder (e.g., cancer). The other therapeutic agent of the pharmaceutical combination formulation or dosing regimen preferably has complementary activities to the compound of Formula I such that they do not adversely affect each other. Such agents are suitably present in combination in amounts that are effective for the purpose intended.

In one embodiment of the invention, the compound of Formula I, or a stereoisomer, tautomer, or pharmaceutically acceptable salt or prodrug thereof, may be co-administered with one or more other therapeutic agents for the treatment and prevention of STING mediated diseases. Thus in another aspect the present invention provides pharmaceutical compositions for treating STING mediated diseases comprising a therapeutically effective amount of a compound of formula I and one or more other therapeutic agents.

In one embodiment for example, for the treatment of the inflammatory diseases rheumatoid arthritis, psoriasis, inflammatory bowel disease, COPD, asthma and allergic rhinitis a compound of formula I may be combined with other therapeutic agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-10) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic 1-1 receptor antagonists such as cetirizine, loratadine, desloratadine, fexofenadine, astemnizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate, and (14) PI3K-delta inhibitors (Phosphatidylinositol-4,5-bisphosphate 3-kinase-delta inhibitors).

In another embodiment of the invention, the compounds of Formula I, or a stereoisomer, tautomer, or pharmaceutically acceptable salt or prodrug thereof, may be employed alone or in combination with other therapeutic agents for the treatment of hyperproliferative disorders (e.g., cancer) including standard chemotherapy regimens, and anti-CD20 monoclonal antibodies, rituximab, bendamustine, ofatumumab, fludarabine, lenalidomide, and/or bortezomib.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active therapeutic agents simultaneously exert their biological activities.

SCHEMES AND EXAMPLES

The abbreviations used herein have the following tabulated meanings. Abbreviations not tabulated below have their meanings as commonly used unless specifically stated otherwise.

| | |
|---|---|
| ACN | Acetonitrile |
| AcOH | acetic acid |
| AQ, aq, | Aqueous |
| (Boc)$_2$O | di-tert-butyl dicarbonate |
| Boc | tert-butoxycarbamate |
| tBu—OH | tert-butyl alcohol |

| | |
|---|---|
| BuLi (n-BuLi) | n-butyllithium |
| calcd | Calculated |
| CELITE, Celite ™, Celite | A trademarked version of diatomaceous earth |
| D, d | Day |
| DABCO | 1,4-diazabicyclo[2.2.2]octane |
| DCM | Dichloromethane |
| DMP Dess-Martin Periodinane | DessMartin Periodinane, 1,1,1-Triacetoxy)-1,1-dihydro-1,2-benziodoxol-3(1H)-one;. A reagent used for mild oxidation of alcohols to aldehydes and ketones. |
| DiBAl-H, DIBAL-H | diisobutylaluminum hydride |
| DIAD | Diisopropyl azodicarboxylate |
| DIPEA | Diisopropylethylamine |
| DMA | Dimethylacetamide |
| DMAP | Dimethylaminopyridine |
| DMEA | Dimethylethylamine |
| DMF | Dimethylformamide |
| DMSO | dimethyl sulfoxide |
| Dppp | 1,3-bis(diphenylphosphino)propane |
| ES | electron spray |
| MS ESI, ESI MS | Electrospray ionization mass spectrometers (ESI MS) |
| EtOAc | ethyl acetate |
| EtOH | Ethanol |
| $Et_3N$ | Trimethylamine |
| g, gm | Gram |
| HATU | 1-[bis(dimethylamino)methylene]-1H-1,2,3-triazolo[4,5-b]pyridinium 3-oxid hexafluorophosphate |
| Hunig's Base | N,N-diisopropylethylamine |
| HPLC | high performance liquid chromatography |
| $IC_{50}$, IC50 | concentration of drug at which 50% of the target is inhibited |
| J | NMR Coupling constant |
| $K_2CO_3$ | Potassium carbonate |
| LCMS | liquid chromatography coupled to mass spectrometer |
| $LiBH_4$ | Lithium borohydride |
| mg | Milligram |
| mL | Milliliter |
| mmol | Millimole |
| MeCN | Acetonitrile |
| MHz | Mega Hertz |
| MeOH | Methanol |
| MS | mass spectrum (data) |
| MsCl | methanesulfonyl chloride |
| N | Normal, equivalents of solute/liter of solution |
| $Na_2SO_4$ | sodium sulfate |
| NaCl | Sodium chloride |
| $NaHCO_3$ | Sodium bicarbonate |
| NaOH | Sodium hydroxide |
| $NEt_3$, $Et_3N$ | Triethylamine |
| NMR | nuclear magnetic resonance (data) |
| $Pd(OAc)_2$ | palladium II acetate |
| $PdCl_2(dppf)$ | 1,1'-bis(diphenylphosphino)ferrocene-palladium(II)dichloride |
| $Pd_2(dba)_3$ | tris(dibenzylideneacetone) dipalladium(0) |
| $Pd(PPh_3)_4$, $Pd(Ph_3P)_4$ | tetrakis(triphenylphosphine) palladium(0) |
| PG | Protecting Group |
| RPM, rpm | Revolutions per minute |
| RT, rt, rt. | room temperature |
| Sat., SAT, sat | Saturated |
| SFC | Supercritical fluid chromatography |
| tBu, t-BU | Tert-butyl |
| TBAI | Tetrabutylammonium iodide |
| TEA | Trimethylamine |
| TFA | trifluoroacetic acid |
| THF | Tetrahydrofuran |
| THP1 cells | A human monocytic cell line derived from an acute monocytic leukemia patient. |
| XPhos | 2-dicyclohexylphosphino-2',4',6'-triisopropylbiphenyl |
| μ | Micro |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated.

All reactions were stirred (mechanically, stir bar/stir plate, or shaken) and conducted under an inert atmosphere of nitrogen or argon unless specifically stated otherwise. All temperatures are degrees Celsius (° C.) unless otherwise noted. Ambient temperature is 15-25° C.

Most compounds were purified by reverse-phase preparative HPLC, MPLC on silica gel, recrystallization and/or trituration (suspension in a solvent followed by filtration of the solid). The course of the reactions was followed by thin layer chromatography (TLC) and/or LCMS and/or NMR and reaction times are given for illustration only.

All end products were analyzed by NMR and LCMS. Intermediates were analyzed by NMR and/or TLC and/or LCMS.

In cases where mixtures or gradients of solvents or solution reagents are described, the mixtures are on a volume basis unless otherwise indicated.

General Synthetic Schemes

The compounds of the generic formula may be prepared from known or readily prepared starting materials, following methods known to one skilled in the art of organic synthesis. Methods useful for making the compounds are set forth in the Examples below and are generalized in Schemes 1 through 2 presented below. Alternative synthetic pathways and analogous structures will be apparent to those skilled in the art of organic synthesis.

Scheme 1

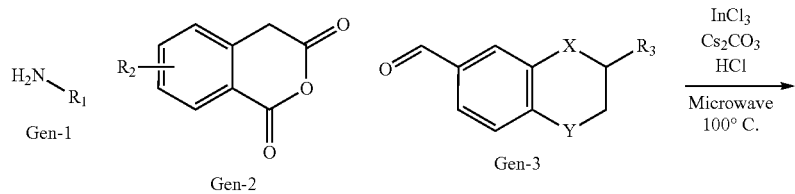

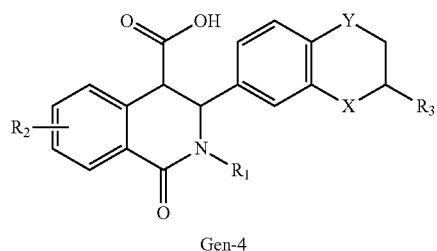

Several synthetic routes may be employed in the syntheses of the compounds described herein. One such route is illustrated in Scheme 1. In this approach, structures of Gen-4 can be synthesized in a one pot with commercially available Gen-1 anilines, Gen-2 homophthalic anhydrides, and Gen-3 aldehydes by heating in a microwave reactor with cesium carbonate ($Cs_2CO_3$), acid, and indium chloride ($InCl_3$) as a catalyst.

Scheme 2

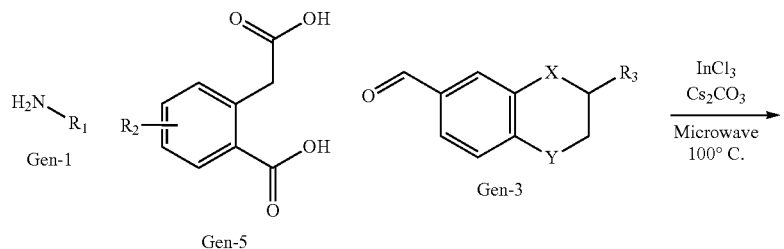

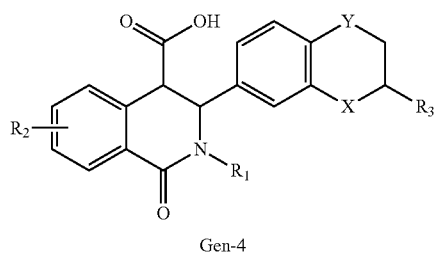

Alternatively, structures of Gen-4, may be synthesized using a modified route illustrated in Scheme 2, where the homophthalic anhydride is replaced with commercially available benzoic acid (Gen-5) to provide Gen-4.

Example 1

(3S,4S or 3R,4R)-2-(4-(tert-butyl)-3-chlorophenyl)-3-(2,3-dihydrobenzo[b][1,4]dioxin-6-yl)-1-oxo-1,2,3,4-tetrahydroisoquinoline-4-carboxylic acid (1-1)

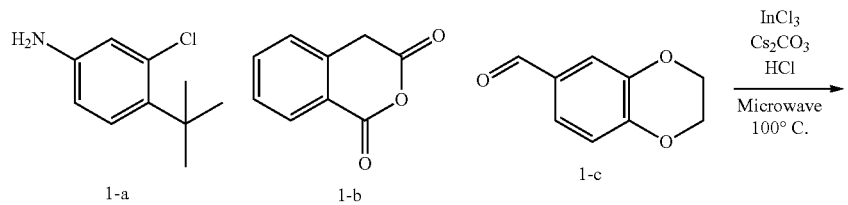

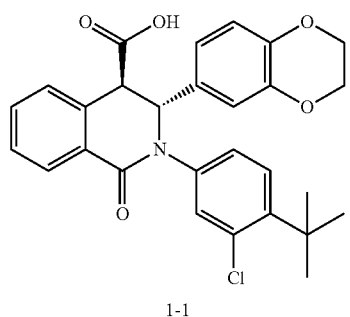

4-(tert-butyl)-3-chloroaniline (1-a) (60 mg, 0.327 mmol), isochromane-1,3-dione (1-b) (53 mg 0.327 mmol), and 2,3-dihydrobenzo[b][1,4]dioxine-6-carbaldehyde (1-c) (59 mg, 0.359 mmol) were added to a microwave vial followed by Indium(III) chloride (InCl₃) (4.3 mg, 0.02 mmol). The vial was sparged with nitrogen then MeCN (acetonitrile) (1.1 mL) was added. The vial was sealed and heated in a microwave reactor for 45 minutes at 100° C. The reaction mixture was cooled to ambient temperature and Cs₂CO₃ (cesium carbonate) (160 mg, 0.490 mmol) was added. The resulting mixture was heated in the microwave reactor for 45 minutes at 100° C. The reaction mixture was diluted with water (1 mL), 2N HCl (0.49 mL) and EtOAc (3 mL). After stirring for 10 minutes the organic phase was separated and concentrated under reduced pressure. The resulting residue was dissolved in DMSO (1 mL), filtered, and purified by mass triggered reverse phase HPLC (ACN/water with 0.1% TFA modifier) to afford a mixture of trans enantiomers. The mixture was further purified by chiral SFC (Chiralpak® AS-H column (Chiral Technologies, Inc., West Chester, Pa., USA), 15%/85% methanol+0.25% Dimethyl Ethyl Amine/CO₂ to afford 1-1 (faster eluting). MS ESI calcd. for $C_{28}H_{26}ClNO_5$ [M+H]⁺ 492, found 492. ¹H NMR (499 MHz, DMSO-$d_6$) δ 7.95 (d, J=7.7 Hz, 1H), 7.50-7.43 (m, 3H), 7.41-7.35 (m, 1H), 7.30-7.23 (m, 2H), 6.71 (d, J=8.3 Hz, 1H), 6.65-6.58 (m, 2H), 5.66 (s, 1H), 4.14 (s, 4H), 3.98 (s, 1H), 1.43 (s, 9H).

Example 2

(3S,4S or 3R,4R)-2-(4-(tert-butyl)-3-chlorophenyl)-3-(2,3-dihydrobenzo[b][1,4]dioxin-6-yl)-7-fluoro-oxo-1,2,3,4-tetrahydroisoquinoline-4-carboxylic acid (1-2)

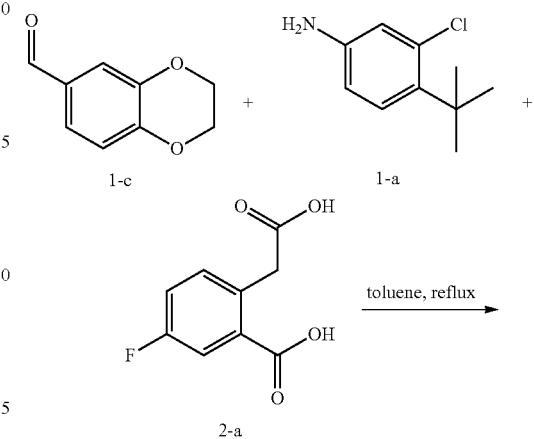

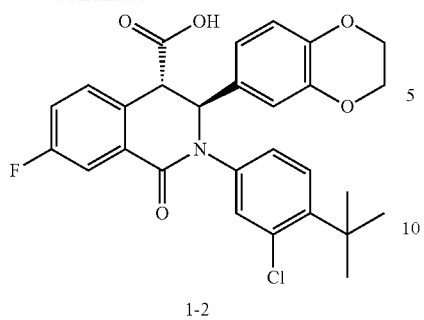

1-2

To a solution of 4-(tert-butyl)-3-chloroaniline (70 mg, 0381 mmol) in toluene (1.9 mL), 2-(carboxymethyl)-5-fluorobenzoic acid (*Bioorg. Med Chem. Left.*, 2012, 22, 7707-7710) (76 mg, 0.381 mmol) and 2,3-dihydrobenzo[b][1,4]dioxine-6-carbaldehyde (63 mg, 0.381 mmol) were added at RT. The vial was sparged with nitrogen, sealed and brought to 110° C. for 18 hours. The reaction mixture was concentrated under reduced pressure and the resulting residue was purified by mass triggered reverse phase HPLC (ACN/water with 0.1% TFA modifier) to afford a mixture of trans enantiomers. The mixture was further purified by chiral SFC (Chiralpak® AS-H column, 20%/80% methanol 0.25% Dimethyl Ethyl Amine/CO$_2$) to afford 2-1-2 (faster eluting). MS ESI calcd. for $C_{28}H_{25}ClFNO_5[M+H]^+$ 510, found 510. $^1$H NMR (600 MHz, DMSO-d$_6$) δ 7.60 (d, J=9.1 Hz, 1H), 7.46-7.40 (m, 2H), 7.31-7.20 (m, 3H), 6.68 (d, J=8.4 Hz, 1H), 6.61-6.52 (m, 2H), 5.64 (s, 1H), 4.11 (s, 4H), 3.94 (s, 1H), 1.39 (s, 9H).

Intermediate 1 for 1-56

7-(benzyloxy)isochromane-1,3-dione (I-1)

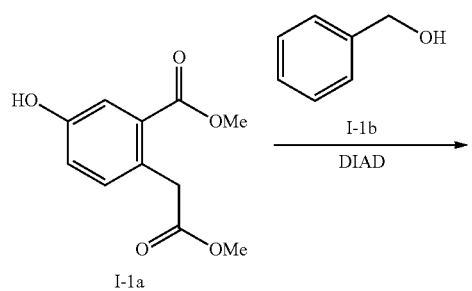

I-1a

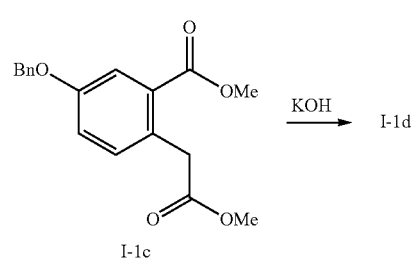

I-1c

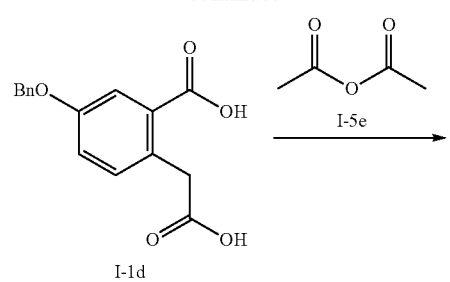

I-1d

I-1

Step 1: Diisopropyl azodicarboxylate (DIAD) (1-1b) (6.9 g, 27 mmol) was added to a solution of methyl 5-hydroxy-2-(2-methoxy-2-oxoethyl)benzoate (1-1a) (3.0 g, 13.4 mmol) and triphenylphosphine (5.3 g, 20 mmol) in DCM (67 mL) at 0° C. The reaction mixture was warmed to room temperature and stirred for 3 hours then concentrated under reduced pressure. The resulting residue was directly purified by silica gel chromatography to afford methyl 5-(benzyloxy)-2-(2-methoxy-2-oxoethyl)benzoate (1-1c). MS ESI calcd. for $C_{18}H_{19}O_5$ $[M+H]^+$ 315, found 315.

Step 2: KOH (1.0M, 5.7 mL, 5.7 mmol) was added to a solution of methyl 5-(benzyloxy)-2-(2-methoxy-2-oxoethyl)benzoate (I-1c) (0.3 g, 0.95 mmol) in dioxane (3.2 mL). The reaction mixture was stirred at 40° C. for 3 hours. The reaction mixture was concentrated under reduced pressure and remaining aqueous solution was washed with ether. Aqueous solution adjusted to pH 7 with IM HCl (hydrochloric acid) then extracted with ethyl acetate. The organic layer was separated, dried over sodium sulfate, filtered and concentrated under reduced pressure to afford 5-(benzyloxy)-2-(carboxymethyl)benzoic acid (I-1d). MS ESI calcd. for $C_{16}H_{15}O_5$ $[M+H]^+$ 287, found 287.

Step 3: 5-(benzyloxy)-2-(carboxymethyl)benzoic acid (I-1d) (0.1 g, 0.35 mmol) was refluxed in a mixture of toluene (2.5 mL) and acetic anhydride (2.5 mL, 27 mmol) for 5 hours. The reaction mixture was concentrated under reduced pressure to afford 7-(benzyloxy)isochromane-1,3-dione (I-1). MS ESI calcd. for $C_{16}H_{13}O_4$ $[M+H]^+$ 269, found 269.

Compounds 1-3 through 1-64 disclosed in Table 1 were prepared in a manner analogous to Examples 1 and 2, using the appropriate amines and aldehydes from commercially available vendors.

TABLE 1

| Ex. | Structure | Name | Exact Mass [M + H]+ |
|---|---|---|---|
| 1-3 | 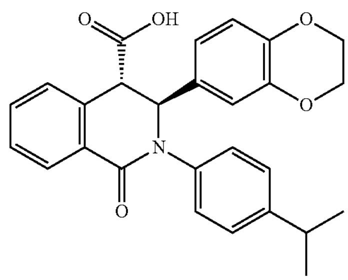 [SMILES: CC(C)c1ccc(N2C(=O)c3ccccc3[C@H](C(=O)O)[C@H]2c2ccc3c(c2)OCCO3)cc1] | (3R,4R) or (3S,4S)-3-(2,3-dihydro-1,4-benzodioxin-6-yl)-2-[4-(1-methylethyl)phenyl]-1-oxo-1,2,3,4-tetrahydroisoquinoline-4-carboxylic acid | Calcd 444; found 444 |
| 1-4 | 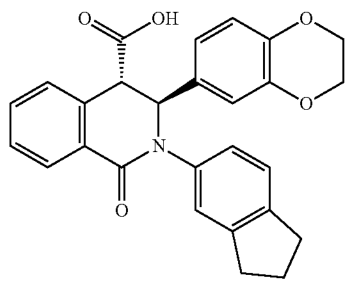 [SMILES: O=C(O)[C@H]1c2ccccc2C(=O)N(c2ccc3c(c2)CCC3)[C@@H]1c1ccc2c(c1)OCCO2] | (3S,4S) or (3R,4R)-3-(2,3-dihydro-1,4-benzodioxin-6-yl)-2-(2,3-dihydro-1H-inden-5-yl)-1-oxo-1,2,3,4-tetrahydroisoquinoline-4-carboxylic acid | Calcd 442; found 442 |
| 1-5 | 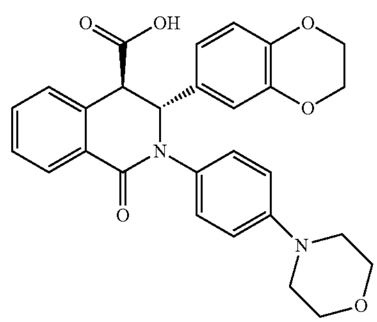 [SMILES: O=C(O)[C@@H]1c2ccccc2C(=O)N(c2ccc(N3CCOCC3)cc2)[C@H]1c1ccc2c(c1)OCCO2] | (3R,4R) and (3S,4S)-3-(2,3-dihydro-1,4-benzodioxin-6-yl)-2-(4-morpholin-4-ylphenyl)-1-oxo-1,2,3,4-tetrahydroisoquinoline-4-carboxylic acid | Calcd 487; found 487 |
| 1-6 | 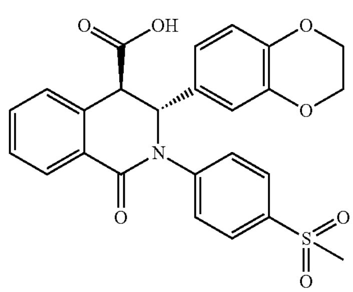 [SMILES: CS(=O)(=O)c1ccc(N2C(=O)c3ccccc3[C@@H](C(=O)O)[C@@H]2c2ccc3c(c2)OCCO3)cc1] | (3R,4R) and (3S,4S)-3-(2,3-dihydro-1,4-benzodioxin-6-yl)-2-[4-(methylsulfonyl)phenyl]-1-oxo-1,2,3,4-tetrahydroisoquinoline-4-carboxylic acid | Calcd 480; found 480 |
| 1-7 | 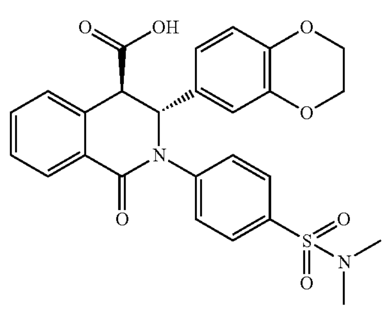 [SMILES: CN(C)S(=O)(=O)c1ccc(N2C(=O)c3ccccc3[C@@H](C(=O)O)[C@@H]2c2ccc3c(c2)OCCO3)cc1] | (3R,4R) and (3S,4S)-3-(2,3-dihydro-1,4-benzodioxin-6-yl)-2-[4-(dimethylsulfamoyl)phenyl]-1-oxo-1,2,3,4-tetrahydroisoquinoline-4-carboxylic acid | Calcd 509; found 509 |

TABLE 1-continued

| Ex. | Structure | Name | Exact Mass [M + H]+ |
|---|---|---|---|
| 1-8 | 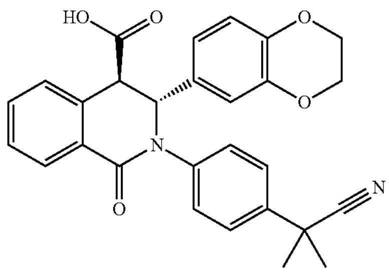 [SMILES: CC(C)(C#N)c1ccc(N2C(=O)c3ccccc3[C@@H](C(=O)O)[C@@H]2c2ccc3c(c2)OCCO3)cc1] | (3R,4R) and (3S,4S) (-2-[4-(1-cyano-1-methylethyl)phenyl]-3-(2,3-dihydro-1,4-benzodioxin-6-yl)-1-oxo-1,2,3,4-tetrahydroisoquinoline-4-carboxylic acid | Calcd 469; found 469 |
| 1-9 | 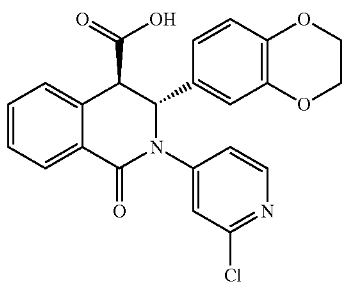 [SMILES: O=C(O)[C@@H]1c2ccccc2C(=O)N(c2ccnc(Cl)c2)[C@H]1c1ccc2c(c1)OCCO2] | (3R,4R) and (3S,4S)-2-(2-chloropyridin-4-yl)-3-(2,3-dihydro-1,4-benzodioxin-6-yl)-1-oxo-1,2,3,4-tetrahydroisoquinoline-4-carboxylic acid | Calcd 437; found 437 |
| 1-10 | 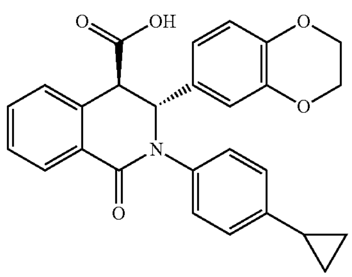 [SMILES: O=C(O)[C@@H]1c2ccccc2C(=O)N(c2ccc(C3CC3)cc2)[C@H]1c1ccc2c(c1)OCCO2] | (3R,4R) and (3S,4S)-2-(4-cyclopropylphenyl)-3-(2,3-dihydro-1,4-benzodioxin-6-yl)-1-oxo-1,2,3,4-tetrahydroisoquinoline-4-carboxylic acid | Calcd 442; found 442 |
| 1-11 | 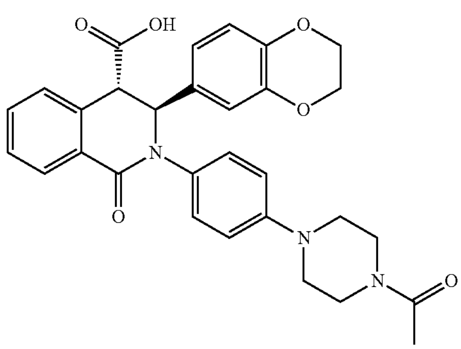 [SMILES: CC(=O)N1CCN(c2ccc(N3C(=O)c4ccccc4[C@H](C(=O)O)[C@H]3c3ccc4c(c3)OCCO4)cc2)CC1] | (3S,4S and (3R,4R))-2-[4-(4-acetylpiperazin-1-yl)phenyl]-3-(2,3-dihydro-1,4-benzodioxin-6-yl)-1-oxo-1,2,3,4-tetrahydroisoquinoline-4-carboxylic acid | Calcd 528; found 528 |
| 1-12 | 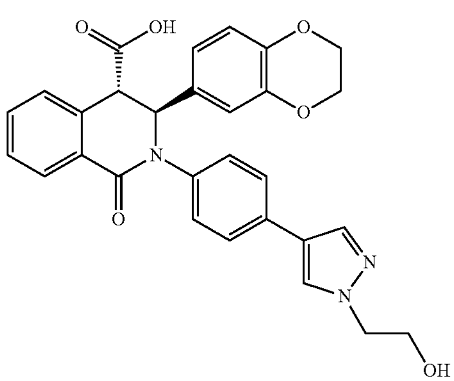 [SMILES: O=C(O)[C@H]1c2ccccc2C(=O)N(c2ccc(-c3cnn(CCO)c3)cc2)[C@@H]1c1ccc2c(c1)OCCO2] | (3S,4S) and (3R,4R)-3-(2,3-dihydro-1,4-benzodioxin-6-yl)-2-{4-[1-(2-hydroxyethyl)-1H-pyrazol-4-yl]phenyl}-1-oxo-1,2,3,4-tetrahydroisoquinoline-4-carboxylic acid | Calcd 512; found 512 |

TABLE 1-continued

| Ex. | Structure | Name | Exact Mass [M + H]+ |
|---|---|---|---|
| 1-13 | 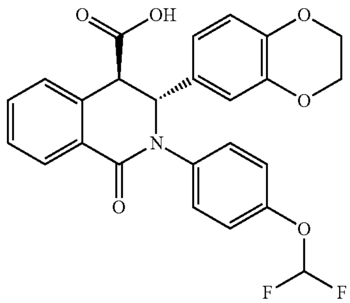 [SMILES: O=C(O)[C@@H]1c2ccccc2C(=O)N(c2ccc(OC(F)F)cc2)[C@H]1c1ccc2c(c1)OCCO2] | (3S,4S) and (3R,4R)-2-[4-(difluoromethoxy)phenyl]-3-(2,3-dihydro-1,4-benzodioxin-6-yl)-1-oxo-1,2,3,4-tetrahydroisoquinoline-4-carboxylic acid | Calcd 468; found 468 |
| 1-14 | 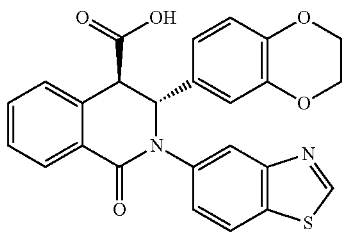 [SMILES: O=C(O)[C@@H]1c2ccccc2C(=O)N(c2ccc3scnc3c2)[C@H]1c1ccc2c(c1)OCCO2] | (3S,4S) and (3R,4R)-2-(1,3-benzothiazol-5-yl)-3-(2,3-dihydro-1,4-benzodioxin-6-yl)-1-oxo-1,2,3,4-tetrahydroisoquinoline-4-carboxylic acid | Calcd 459; found 459 |
| 1-15 | 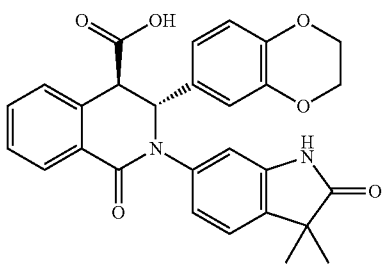 [SMILES: CC1(C)C(=O)Nc2cc(N3C(=O)c4ccccc4[C@@H](C(=O)O)[C@@H]3c3ccc4c(c3)OCCO4)ccc21] | (3S,4S) and (3R,4R)-3-(2,3-dihydro-1,4-benzodioxin-6-yl)-2-(3,3-dimethyl-2-oxo-2,3-dihydro-1H-indol-6-yl)-1-oxo-1,2,3,4-tetrahydroisoquinoline-4-carboxylic acid | Calcd 485; found 485 |
| 1-16 | 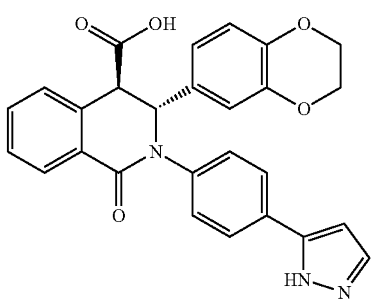 [SMILES: O=C(O)[C@@H]1c2ccccc2C(=O)N(c2ccc(-c3ccn[nH]3)cc2)[C@H]1c1ccc2c(c1)OCCO2] | (3S,4S) and (3R,4R)-3-(2,3-dihydro-1,4-benzodioxin-6-yl)-1-oxo-2-[4-(1H-pyrazol-5-yl)phenyl]-1,2,3,4-tetrahydroisoquinoline-4-carboxylic acid | Calcd 468; found 468 |
| 1-17 | 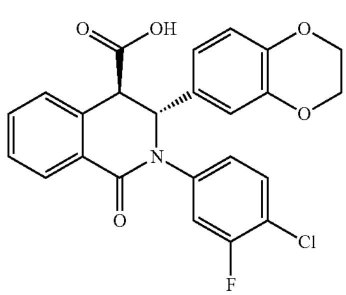 [SMILES: O=C(O)[C@@H]1c2ccccc2C(=O)N(c2ccc(Cl)c(F)c2)[C@H]1c1ccc2c(c1)OCCO2] | (3S,4S) and (3R,4R)-2-(4-chloro-3-fluorophenyl)-3-(2,3-dihydro-1,4-benzodioxin-6-yl)-1-oxo-1,2,3,4-tetrahydroisoquinoline-4-carboxylic acid | Calcd 454; found 454 |

TABLE 1-continued

| Ex. | Structure | Name | Exact Mass [M + H]+ |
|---|---|---|---|
| 1-18 | 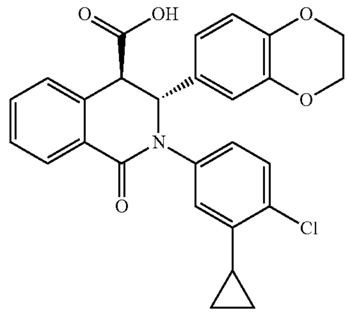 [SMILES: O=C(O)[C@@H]1c2ccccc2C(=O)N(c2ccc(Cl)c(C3CC3)c2)[C@H]1c1ccc2c(c1)OCCO2] | (3S,4S) and (3R,4R)-2-(4-chloro-3-cyclopropylphenyl)-3-(2,3-dihydro-1,4-benzodioxin-6-yl)-1-oxo-1,2,3,4-tetrahydroisoquinoline-4-carboxylic acid | Calcd 476; found 476 |
| 1-19 | 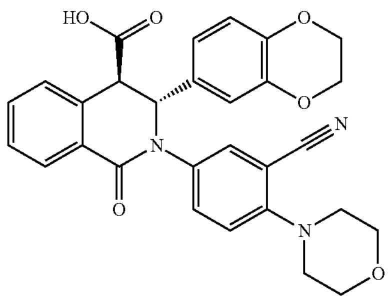 [SMILES: N#Cc1cc(N2C(=O)c3ccccc3[C@@H](C(=O)O)[C@@H]2c2ccc3c(c2)OCCO3)ccc1N1CCOCC1] | (3S,4S) and (3R,4R)-2-(3-cyano-4-morpholin-4-ylphenyl)-3-(2,3-dihydro-1,4-benzodioxin-6-yl)-1-oxo-1,2,3,4-tetrahydroisoquinoline-4-carboxylic acid | Calcd 512; found 512 |
| 1-20 | 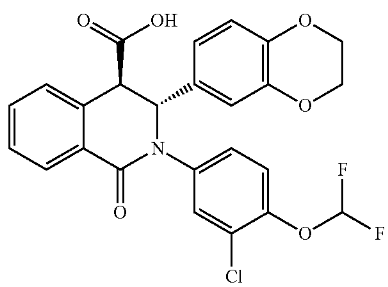 [SMILES: O=C(O)[C@@H]1c2ccccc2C(=O)N(c2ccc(OC(F)F)c(Cl)c2)[C@H]1c1ccc2c(c1)OCCO2] | (3S,4S) and (3R,4R)-2-[3-chloro-4-(difluoromethoxy)phenyl]-3-(2,3-dihydro-1,4-benzodioxin-6-yl)-1-oxo-1,2,3,4-tetrahydroisoquinoline-4-carboxylic acid | Calcd 502; found 502 |
| 1-21 | 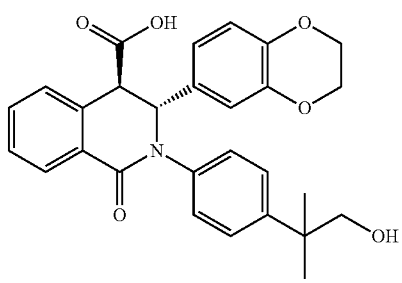 [SMILES: CC(C)(CO)c1ccc(N2C(=O)c3ccccc3[C@@H](C(=O)O)[C@@H]2c2ccc3c(c2)OCCO3)cc1] | (3S,4S) and (3R,4R)-3-(2,3-dihydro-1,4-benzodioxin-6-yl)-2-[4-(2-hydroxy-1,1-dimethylethyl)phenyl]-1-oxo-1,2,3,4-tetrahydroisoquinoline-4-carboxylic acid | Calcd 474; found 474 |
| 1-22 | 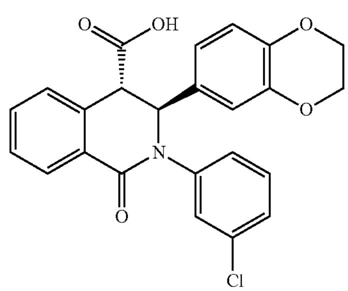 [SMILES: O=C(O)[C@H]1c2ccccc2C(=O)N(c2cccc(Cl)c2)[C@@H]1c1ccc2c(c1)OCCO2] | (3S,4S) and (3R,4R)-2-(3-chlorophenyl)-3-(2,3-dihydro-1,4-benzodioxin-6-yl)-1-oxo-1,2,3,4-tetrahydroisoquinoline-4-carboxylic acid | Calcd 436; found 436 |

TABLE 1-continued

| Ex. | Structure | Name | Exact Mass [M + H]+ |
|---|---|---|---|
| 1-23 | 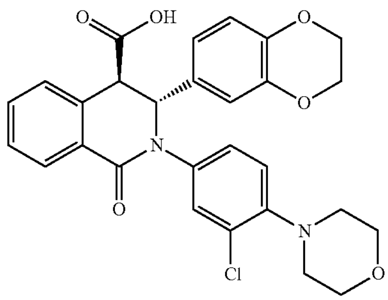 [SMILES: O=C(O)[C@@H]1c2ccccc2C(=O)N(c2ccc(N3CCOCC3)c(Cl)c2)[C@H]1c1ccc2c(c1)OCCO2] | (3S,4S) and (3R,4R)-2-(3-chloro-4-morpholin-4-ylphenyl)-3-(2,3-dihydro-1,4-benzodioxin-6-yl)-1-oxo-1,2,3,4-tetrahydroisoquinoline-4-carboxylic acid | Calcd 521; found 521 |
| 1-24 | 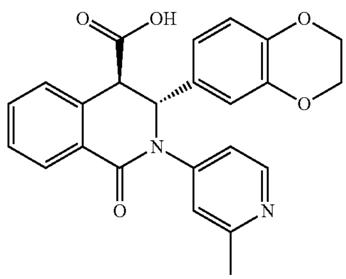 [SMILES: Cc1cc(N2C(=O)c3ccccc3[C@@H](C(=O)O)[C@@H]2c2ccc3c(c2)OCCO3)ccn1] | (3S,4S) and (3R,4R)-3-(2,3-dihydro-1,4-benzodioxin-6-yl)-2-(2-methylpyridin-4-yl)-1-oxo-1,2,3,4-tetrahydroisoquinoline-4-carboxylic acid | Calcd 417; found 417 |
| 1-25 | 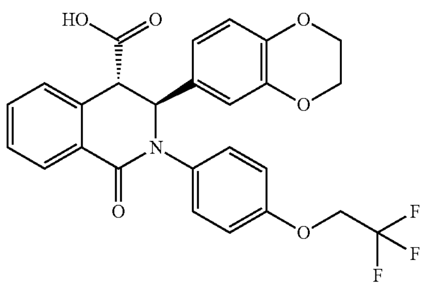 [SMILES: O=C(O)[C@H]1c2ccccc2C(=O)N(c2ccc(OCC(F)(F)F)cc2)[C@@H]1c1ccc2c(c1)OCCO2] | (3S,4S and (3R,4R))-3-(2,3-dihydro-1,4-benzodioxin-6-yl)-1-oxo-2-[4-(2,2,2-trifluoroethoxy)phenyl]-1,2,3,4-tetrahydroisoquinoline-4-carboxylic acid | Calcd 500; found 500 |
| 1-26 | 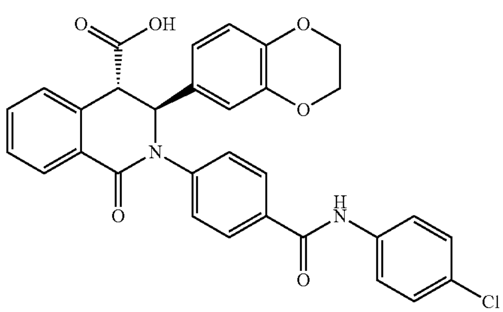 [SMILES: O=C(Nc1ccc(Cl)cc1)c1ccc(N2C(=O)c3ccccc3[C@H](C(=O)O)[C@H]2c2ccc3c(c2)OCCO3)cc1] | (3S,4S and (3R,4R))-2-{4-[(4-chlorophenyl)carbamoyl]phenyl}-3-(2,3-dihydro-1,4-benzodioxin-6-yl)-1-oxo-1,2,3,4-tetrahydroisoquinoline-4-carboxylic acid | Calcd 555; found 555 |
| 1-27 | 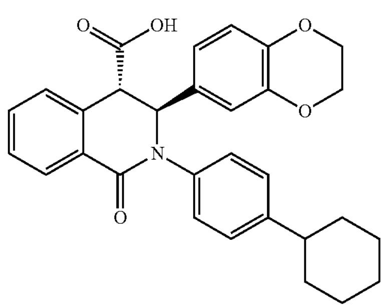 [SMILES: O=C(O)[C@H]1c2ccccc2C(=O)N(c2ccc(C3CCCCC3)cc2)[C@@H]1c1ccc2c(c1)OCCO2] | (3S,4S) and (3R,4R)-2-(4-cyclohexylphenyl)-3-(2,3-dihydro-1,4-benzodioxin-6-yl)-1-oxo-1,2,3,4-tetrahydroisoquinoline-4-carboxylic acid | Calcd 484; found 484 |

TABLE 1-continued

| Ex. | Structure | Name | Exact Mass [M + H]+ |
|---|---|---|---|
| 1-28 | 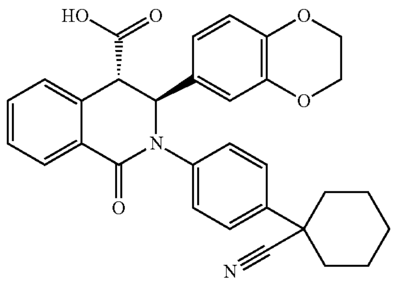 [SMILES: N#CC1(c2ccc(N3C(=O)c4ccccc4[C@H](C(=O)O)[C@H]3c3ccc4c(c3)OCCO4)cc2)CCCCC1] | (3S,4S) and (3S,4R)-2-[4-(1-cyanocyclohexyl)phenyl]-3-(2,3-dihydro-1,4-benzodioxin-6-yl)-1-oxo-1,2,3,4-tetrahydroisoquinoline-4-carboxylic acid | Calcd 509; found 509 |
| 1-29 | 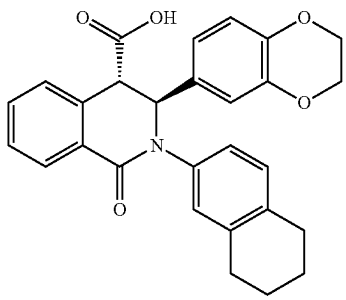 [SMILES: O=C(O)[C@H]1c2ccccc2C(=O)N(c2ccc3c(c2)CCCC3)[C@@H]1c1ccc2c(c1)OCCO2] | (3S,4S) and (3S,4R)-3-(2,3-dihydro-1,4-benzodioxin-6-yl)-1-oxo-2-(5,6,7,8-tetrahydronaphthalen-2-yl)-1,2,3,4-tetrahydroisoquinoline-4-carboxylic acid | Calcd 456; found 456 |
| 1-30 | 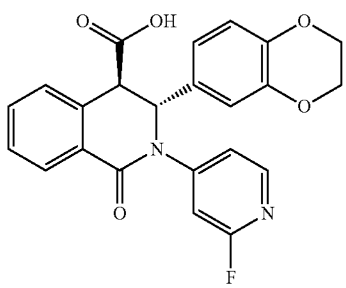 [SMILES: O=C(O)[C@@H]1c2ccccc2C(=O)N(c2ccnc(F)c2)[C@H]1c1ccc2c(c1)OCCO2] | (3S,4S) and (3R,4R)-3-(2,3-dihydro-1,4-benzodioxin-6-yl)-2-(2-fluoropyridin-4-yl)-1-oxo-1,2,3,4-tetrahydroisoquinoline-4-carboxylic acid | Calcd 421; found 421 |
| 1-31 | 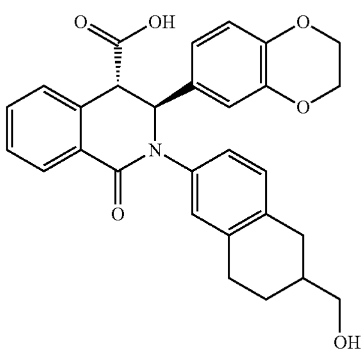 [SMILES: O=C(O)[C@H]1c2ccccc2C(=O)N(c2ccc3c(c2)CCC(CO)C3)[C@@H]1c1ccc2c(c1)OCCO2] | (3S,4S) and (3R,4R)-3-(2,3-dihydro-1,4-benzodioxin-6-yl)-2-[6-(hydroxymethyl)-5,6,7,8-tetrahydronaphthalen-2-yl]-1-oxo-1,2,3,4-tetrahydroisoquinoline-4-carboxylic acid | Calcd 486; found 486 |
| 1-32 | 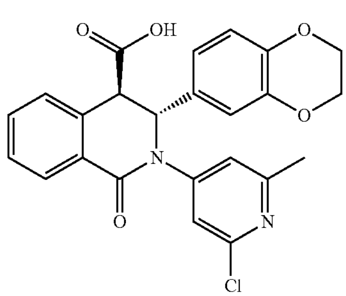 [SMILES: Cc1cc(N2C(=O)c3ccccc3[C@@H](C(=O)O)[C@@H]2c2ccc3c(c2)OCCO3)cc(Cl)n1] | (3S,4S) and (3R,4R)-2-(2-chloro-6-methylpyridin-4-yl)-3-(2,3-dihydro-1,4-benzodioxin-6-yl)-1-oxo-1,2,3,4-tetrahydroisoquinoline-4-carboxylic acid | Calcd 451; found 451 |

TABLE 1-continued

| Ex. | Structure | Name | Exact Mass [M + H]+ |
|---|---|---|---|
| 1-33 | 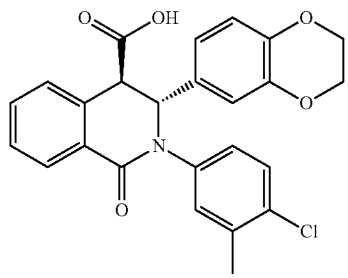 [SMILES: Cc1cc(N2C(=O)c3ccccc3[C@@H](C(=O)O)[C@@H]2c2ccc3c(c2)OCCO3)ccc1Cl] | (3S,4S) and (3R,4R)-2-(4-chloro-3-methylphenyl)-3-(2,3-dihydro-1,4-benzodioxin-6-yl)-1-oxo-1,2,3,4-tetrahydroisoquinoline-4-carboxylic acid | Calcd 450; found 450 |
| 1-34 | 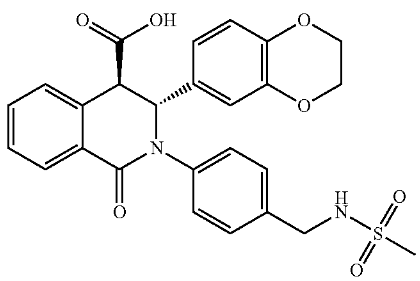 [SMILES: CS(=O)(=O)NCc1ccc(N2C(=O)c3ccccc3[C@@H](C(=O)O)[C@@H]2c2ccc3c(c2)OCCO3)cc1] | (3S,4S) and (3R,4R)-3-(2,3-dihydro-1,4-benzodioxin-6-yl)-2-(4-{[(methylsulfonyl)amino]methyl}phenyl)-1-oxo-1,2,3,4-tetrahydroisoquinoline-4-carboxylic acid | Calcd 509; found 509 |
| 1-35 | 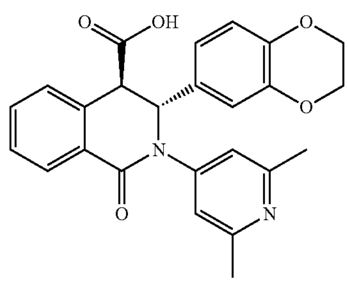 [SMILES: Cc1cc(N2C(=O)c3ccccc3[C@@H](C(=O)O)[C@@H]2c2ccc3c(c2)OCCO3)cc(C)n1] | (3S,4S) and (3R,4R)-3-(2,3-dihydro-1,4-benzodioxin-6-yl)-2-(2,6-dimethylpyridin-4-yl)-1-oxo-1,2,3,4-tetrahydroisoquinoline-4-carboxylic acid | Calcd 431; found 431 |
| 1-36 | 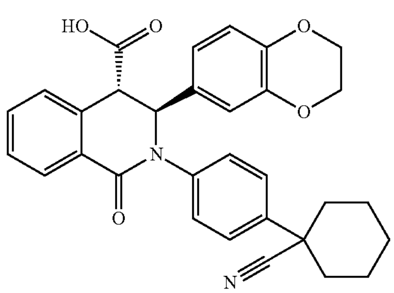 [SMILES: N#CC1(c2ccc(N3C(=O)c4ccccc4[C@H](C(=O)O)[C@H]3c3ccc4c(c3)OCCO4)cc2)CCCCC1] | (3S,4S) or (3R,4R)-2-[4-(1-cyanocyclohexyl)phenyl]-3-(2,3-dihydro-1,4-benzodioxin-6-yl)-1-oxo-1,2,3,4-tetrahydroisoquinoline-4-carboxylic acid | Calcd 509; found 509 |
| 1-37 | 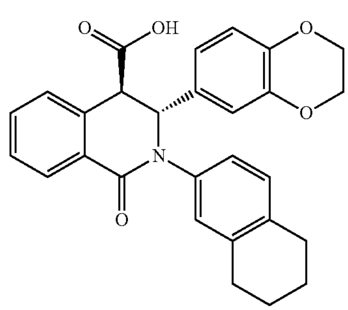 [SMILES: O=C(O)[C@@H]1c2ccccc2C(=O)N(c2ccc3c(c2)CCCC3)[C@H]1c1ccc2c(c1)OCCO2] | (3R,4R) or (3S,4S)-3-(2,3-dihydro-1,4-benzodioxin-6-yl)-1-oxo-2-(5,6,7,8-tetrahydronaphthalen-2-yl)-1,2,3,4-tetrahydroisoquinoline-4-carboxylic acid | Calcd 456; found 456 |

TABLE 1-continued

| Ex. | Structure | Name | Exact Mass [M + H]+ |
|---|---|---|---|
| 1-38 | 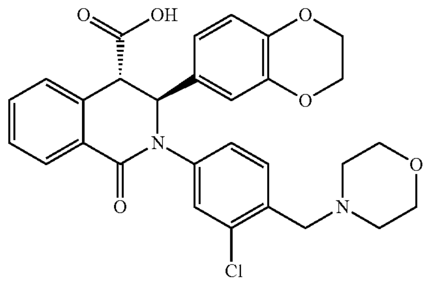 [SMILES: O=C(O)[C@H]1c2ccccc2C(=O)N(c2ccc(CN3CCOCC3)c(Cl)c2)[C@@H]1c1ccc2c(c1)OCCO2] | (3S,4S) and (3R,4R)-2-[3-chloro-4-(morpholin-4-ylmethyl)phenyl]-3-(2,3-dihydro-1,4-benzodioxin-6-yl)-1-oxo-1,2,3,4-tetrahydroisoquinoline-4-carboxylic acid | Calcd 535; found 535 |
| 1-39 | 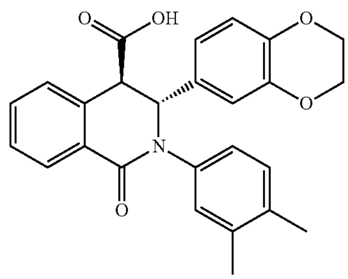 [SMILES: Cc1ccc(N2C(=O)c3ccccc3[C@@H](C(=O)O)[C@@H]2c2ccc3c(c2)OCCO3)cc1C] | (3S,4S) and (3R,4R)-3-(2,3-dihydro-1,4-benzodioxin-6-yl)-2-(3,4-dimethylphenyl)-1-oxo-1,2,3,4-tetrahydroisoquinoline-4-carboxylic acid | Calcd 430; found 430 |
| 1-40 | 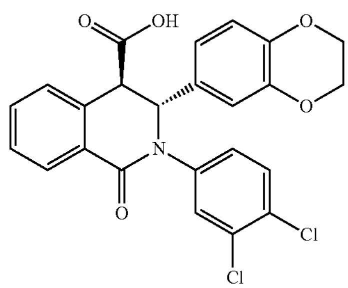 [SMILES: O=C(O)[C@@H]1c2ccccc2C(=O)N(c2ccc(Cl)c(Cl)c2)[C@H]1c1ccc2c(c1)OCCO2] | (3S,4S) or (3R,4R)-2-(3,4-dichlorophenyl)-3-(2,3-dihydro-1,4-benzodioxin-6-yl)-1-oxo-1,2,3,4-tetrahydroisoquinoline-4-carboxylic acid | Calcd 470; found 470 |
| 1-41 | 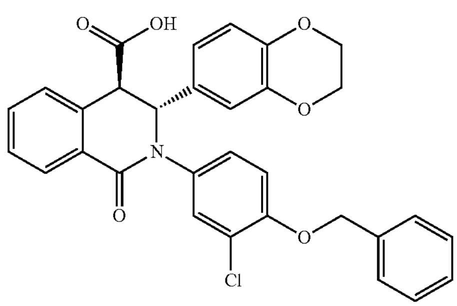 [SMILES: O=C(O)[C@@H]1c2ccccc2C(=O)N(c2ccc(OCc3ccccc3)c(Cl)c2)[C@H]1c1ccc2c(c1)OCCO2] | (3S,4S) and (3R,4R)-2-[4-(benzyloxy)-3-chlorophenyl]-3-(2,3-dihydro-1,4-benzodioxin-6-yl)-1-oxo-1,2,3,4-tetrahydroisoquinoline-4-carboxylic acid | Calcd 542; found 542 |
| 1-42 | 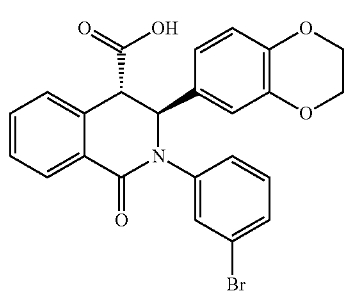 | (3S,4S) and (3R,4R)-2-(3-bromophenyl)-3-(2,3-dihydro-1,4-benzodioxin-6-yl)-1-oxo-1,2,3,4-tetrahydroisoquinoline-4-carboxylic acid | Calcd 480; found 480 |

TABLE 1-continued

| Ex. | Structure | Name | Exact Mass [M + H]+ |
|---|---|---|---|
| 1-43 | 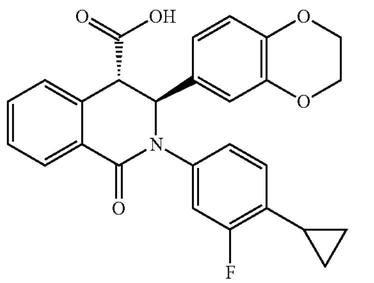 [SMILES: O=C(O)[C@H]1c2ccccc2C(=O)N(c2ccc(C3CC3)c(F)c2)[C@@H]1c1ccc2c(c1)OCCO2] | (3S,4S) and (3R,4R)-2-(4-cyclopropyl-3-fluorophenyl)-3-(2,3-dihydro-1,4-benzodioxin-6-yl)-1-oxo-1,2,3,4-tetrahydroisoquinoline-4-carboxylic acid | Calcd 460; found 460 |
| 1-44 | 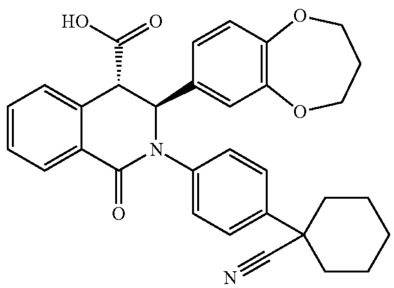 [SMILES: N#CC1(c2ccc(N3C(=O)c4ccccc4[C@H](C(=O)O)[C@H]3c3ccc4c(c3)OCCCO4)cc2)CCCCC1] | (3S,4S) or (3R,4R)-2-[4-(1-cyanocyclohexyl)phenyl]-3-(3,4-dihydro-2H-1,5-benzodioxepin-7-yl)-1-oxo-1,2,3,4-tetrahydroisoquinoline-4-carboxylic acid | Calcd 523; found 523 |
| 1-45 | 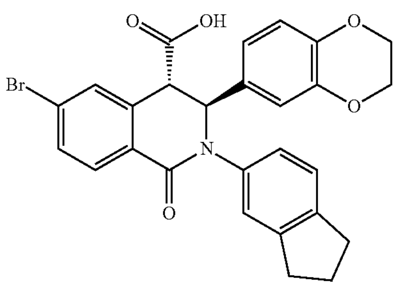 [SMILES: O=C(O)[C@H]1c2cc(Br)ccc2C(=O)N(c2ccc3c(c2)CCC3)[C@@H]1c1ccc2c(c1)OCCO2] | (3S,4S) and (3R,4R)-6-bromo-3-(2,3-dihydro-1,4-benzodioxin-6-yl)-2-(2,3-dihydro-1H-inden-5-yl)-1-oxo-1,2,3,4-tetrahydroisoquinoline-4-carboxylic acid | Calcd 520; found 520 |
| 1-46 | 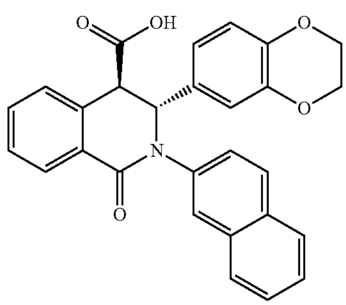 [SMILES: O=C(O)[C@@H]1c2ccccc2C(=O)N(c2ccc3ccccc3c2)[C@H]1c1ccc2c(c1)OCCO2] | (3S,4S) and (3R,4R)-3-(2,3-dihydro-1,4-benzodioxin-6-yl)-2-naphthalen-2-yl-1-oxo-1,2,3,4-tetrahydroisoquinoline-4-carboxylic acid | Calcd 42; found 452 |
| 1-47 | 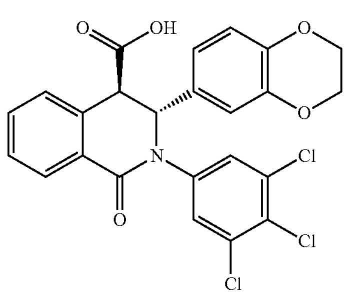 [SMILES: O=C(O)[C@@H]1c2ccccc2C(=O)N(c2cc(Cl)c(Cl)c(Cl)c2)[C@H]1c1ccc2c(c1)OCCO2] | (3S,4S) and (3R,4R)-3-(2,3-dihydro-1,4-benzodioxin-6-yl)-1-oxo-2-(3,4,5-trichlorophenyl)-1,2,3,4-tetrahydroisoquinoline-4-carboxylic acid | Calcd 504; found 504 |

TABLE 1-continued

| Ex. | Structure | Name | Exact Mass [M + H]+ |
|---|---|---|---|
| 1-48 | 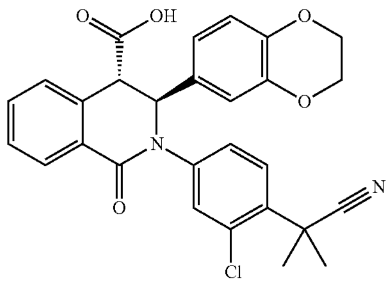 [SMILES: CC(C)(C#N)c1ccc(N2C(=O)c3ccccc3[C@H](C(=O)O)[C@H]2c2ccc3c(c2)OCCO3)cc1Cl] | (3S,4S) and (3R,4R)-2-[3-chloro-4-(1-cyano-1-methylethyl)phenyl]-3-(2,3-dihydro-1,4-benzodioxin-6-yl)-1-oxo-1,2,3,4-tetrahydroisoquinoline-4-carboxylic acid | Calcd 503; found 503 |
| 1-49 | 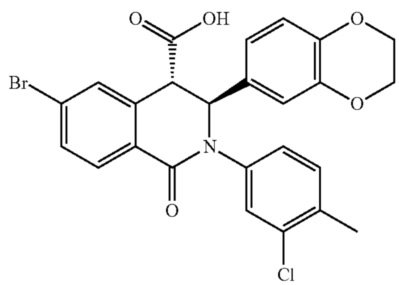 [SMILES: Cc1ccc(N2C(=O)c3ccc(Br)cc3[C@H](C(=O)O)[C@H]2c2ccc3c(c2)OCCO3)cc1Cl] | (3S,4S) and (3R,4R)-6-bromo-2-(3-chloro-4-methylphenyl)-3-(2,3-dihydro-1,4-benzodioxin-6-yl)-1-oxo-1,2,3,4-tetrahydroisoquinoline-4-carboxylic acid | Calcd 528; found 528 |
| 1-50 | 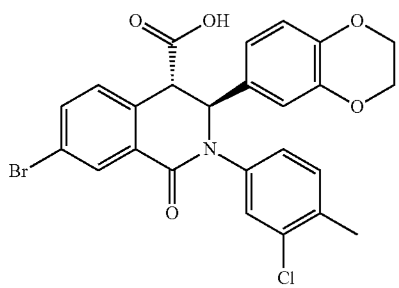 [SMILES: Cc1ccc(N2C(=O)c3cc(Br)ccc3[C@H](C(=O)O)[C@H]2c2ccc3c(c2)OCCO3)cc1Cl] | (3S,4S) and (3R,4R)-7-bromo-2-(3-chloro-4-methylphenyl)-3-(2,3-dihydro-1,4-benzodioxin-6-yl)-1-oxo-1,2,3,4-tetrahydroisoquinoline-4-carboxylic acid | Calcd 528; found 528 |
| 1-51 | 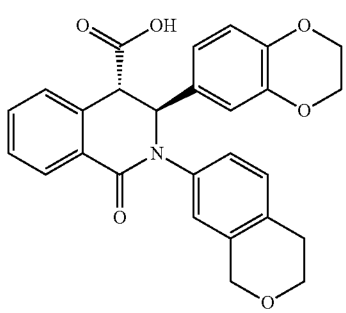 [SMILES: O=C(O)[C@H]1c2ccccc2C(=O)N(c2ccc3c(c2)COCC3)[C@@H]1c1ccc2c(c1)OCCO2] | (3S,4S) and (3R,4R)-3-(2,3-dihydro-1,4-benzodioxin-6-yl)-2-(3,4-dihydro-1H-isochromen-7-yl)-1-oxo-1,2,3,4-tetrahydroisoquinoline-4-carboxylic acid | Calcd 458; found 458 |
| 1-52 | 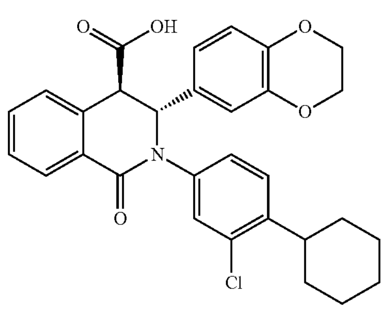 [SMILES: O=C(O)[C@@H]1c2ccccc2C(=O)N(c2ccc(C3CCCCC3)c(Cl)c2)[C@H]1c1ccc2c(c1)OCCO2] | (3R,4R) or (3S,4S)-2-(3-chloro-4-cyclohexylphenyl)-3-(2,3-dihydro-1,4-benzodioxin-6-yl)-1-oxo-1,2,3,4-tetrahydroisoquinoline-4-carboxylic acid | Calcd 518; found 518 |

TABLE 1-continued

| Ex. | Structure | Name | Exact Mass [M + H]+ |
|---|---|---|---|
| 1-53 | 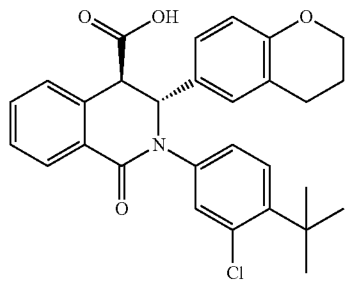 [SMILES: CC(C)(C)c1ccc(N2C(=O)c3ccccc3[C@@H](C(=O)O)[C@@H]2c2ccc3c(c2)CCCO3)cc1Cl] | (3R,4R) and (3S,4S)-2-(4-tert-butyl-3-chlorophenyl)-3-(3,4-dihydro-2H-chromen-6-yl)-1-oxo-1,2,3,4-tetrahydroisoquinoline-4-carboxylic acid | Calcd 490; found 490 |
| 1-54 | 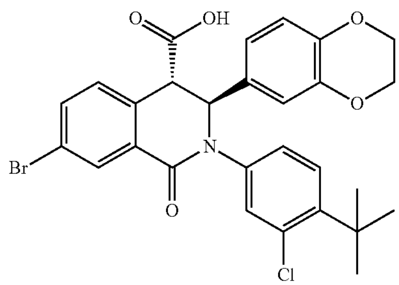 [SMILES: CC(C)(C)c1ccc(N2C(=O)c3cc(Cl)ccc3[C@H](C(=O)O)[C@H]2c2ccc3c(c2)OCCO3)cc1Cl] | (3S,4S) and (3R,4R)-7-bromo-2-(4-tert-butyl-3-chlorophenyl)-3-(2,3-dihydro-1,4-benzodioxin-6-yl)-1-oxo-1,2,3,4-tetrahydroisoquinoline-4-carboxylic acid | Calcd 570; found 570 |
| 1-55 | 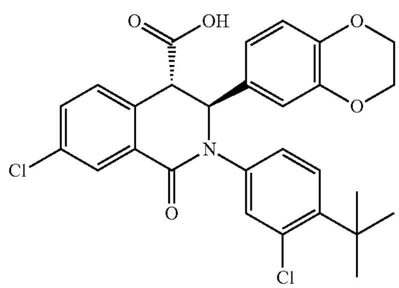 | (3S,4S) and (3R,4R)-2-(4-tert-butyl-3-chlorophenyl)-7-chloro-3-(2,3-dihydro-1,4-benzodioxin-6-yl)-1-oxo-1,2,3,4-tetrahydroisoquinoline-4-carboxylic acid | Calcd 526; found 526 |
| 1-56 | 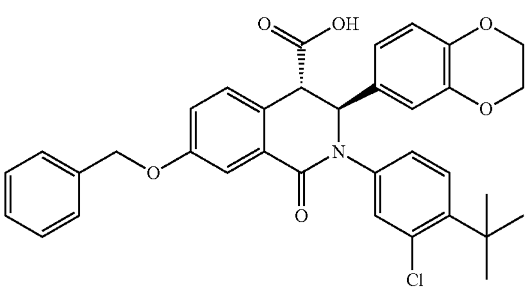 [SMILES: CC(C)(C)c1ccc(N2C(=O)c3cc(OCc4ccccc4)ccc3[C@H](C(=O)O)[C@H]2c2ccc3c(c2)OCCO3)cc1Cl] | (3S,4S) and (3R,4R)-7-(benzyloxy)-2-(4-tert-butyl-3-chlorophenyl)-3-(2,3-dihydro-1,4-benzodioxin-6-yl)-1-oxo-1,2,3,4-tetrahydroisoquinoline-4-carboxylic acid | Calcd 598; found 598 |
| 1-57 | 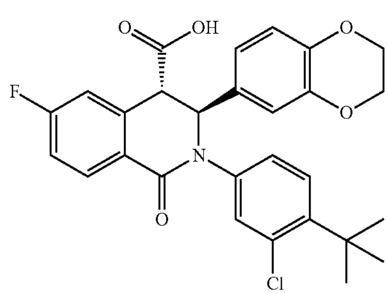 [SMILES: CC(C)(C)c1ccc(N2C(=O)c3ccc(F)cc3[C@H](C(=O)O)[C@H]2c2ccc3c(c2)OCCO3)cc1Cl] | (3R,4R) or (3S,4S)-2-(4-tert-butyl-3-chlorophenyl)-3-(2,3-dihydro-1,4-benzodioxin-6-yl)-6-fluoro-1-oxo-1,2,3,4-tetrahydroisoquinoline-4-carboxylic acid | Calcd 510; found 510 |

TABLE 1-continued

| Ex. | Structure | Name | Exact Mass [M + H]+ |
|---|---|---|---|
| 1-58 | 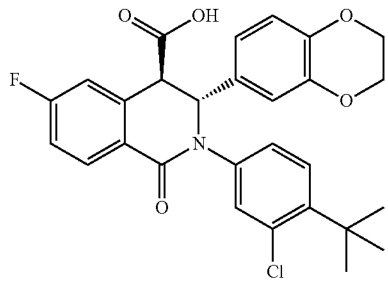 [SMILES: CC(C)(C)c1ccc(N2C(=O)c3ccc(F)cc3[C@@H](C(=O)O)[C@@H]2c2ccc3c(c2)OCCO3)cc1Cl] | (3R,4R) or (3S,4S)-2-(4-tert-butyl-3-chlorophenyl)-3-(2,3-dihydro-1,4-benzodioxin-6-yl)-6-fluoro-1-oxo-1,2,3,4-tetrahydroisoquinoline-4-carboxylic acid | Calcd 510; found 510 |
| 1-59 | 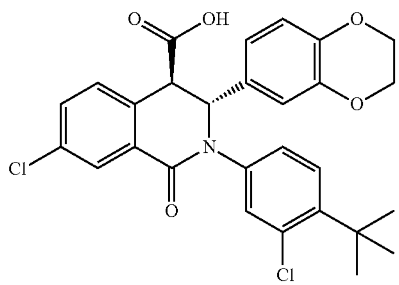 [SMILES: CC(C)(C)c1ccc(N2C(=O)c3cc(Cl)ccc3[C@@H](C(=O)O)[C@@H]2c2ccc3c(c2)OCCO3)cc1Cl] | (3R,4R) or (3S,4S)-2-(4-tert-butyl-3-chlorophenyl)-7-chloro-3-(2,3-dihydro-1,4-benzodioxin-6-yl)-1-oxo-1,2,3,4-tetrahydroisoquinoline-4-carboxylic acid | Calcd 526; Found 526 |
| 1-60 | 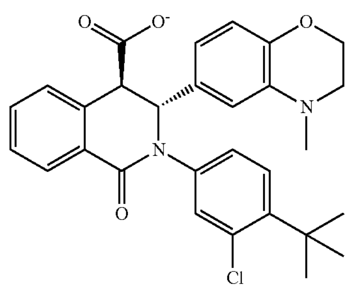 [SMILES: CN1CCOc2ccc([C@H]3[C@H](C(=O)[O-])c4ccccc4C(=O)N3c3ccc(C(C)(C)C)c(Cl)c3)cc21] | (3R,4R) or (3S,4S)-2-(4-tert-butyl-3-chlorophenyl)-3-(4-methyl-3,4-dihydro-2H-1,4-benzoxazin-6-yl)-1-oxo-1,2,3,4-tetrahydroisoquinoline-4-carboxylic acid | Calcd 505; Found 505 |
| 1-61 | 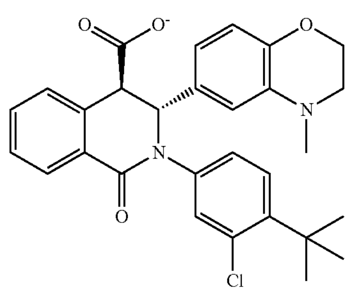 [SMILES: CN1CCOc2ccc([C@H]3[C@H](C(=O)[O-])c4ccccc4C(=O)N3c3ccc(C(C)(C)C)c(Cl)c3)cc21] | (3R,4R) or (3S,4S)-2-(4-tert-butyl-3-chlorophenyl)-3-(4-methyl-3,4-dihydro-2H-1,4-benzoxazin-6-yl)-1-oxo-1,2,3,4-tetrahydroisoquinoline-4-carboxylic acid | Calcd 505; Found 505 |
| 1-62 | 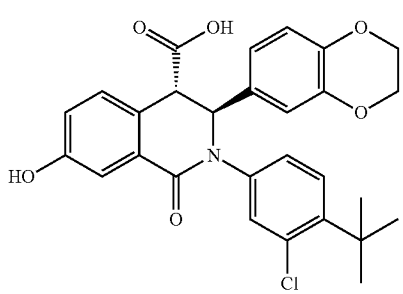 [SMILES: CC(C)(C)c1ccc(N2C(=O)c3cc(O)ccc3[C@H](C(=O)O)[C@H]2c2ccc3c(c2)OCCO3)cc1Cl] | (3S,4S) or (3R,4R)-2-(4-tert-butyl-3-chlorophenyl)-3-(2,3-dihydro-1,4-benzodioxin-6-yl)-7-hydroxy-1-oxo-1,2,3,4-tetrahydroisoquinoline-4-carboxylic acid | Calcd 508; found 508 |

TABLE 1-continued

| Ex. | Structure | Name | Exact Mass [M + H]+ |
|---|---|---|---|
| 1-63 | 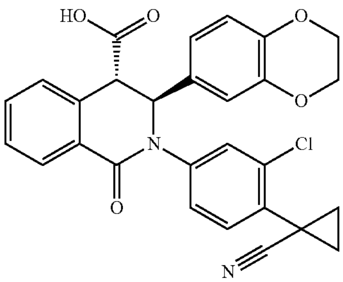 [SMILES: N#CC1(c2ccc(N3C(=O)c4ccccc4[C@H](C(=O)O)[C@H]3c3ccc4c(c3)OCCO4)cc2Cl)CC1] | (3S,4S) or (3R,4R)-2-[3-chloro-4-(1-cyanocyclopropyl)phenyl]-3-(2,3-dihydro-1,4-benzodioxin-6-yl)-1-oxo-1,2,3,4-tetrahydroisoquinoline-4-carboxylic acid | Calcd 501; found 501 |
| 1-64 | 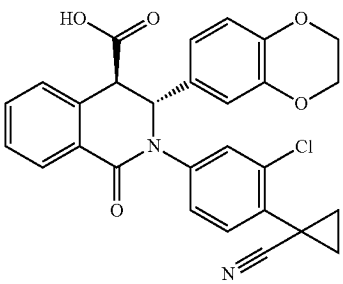 [SMILES: N#CC1(c2ccc(N3C(=O)c4ccccc4[C@@H](C(=O)O)[C@@H]3c3ccc4c(c3)OCCO4)cc2Cl)CC1] | (3R,4R) or (3S,4S)-2-[3-chloro-4-(1-cyanocyclopropyl)phenyl]-3-(2,3-dihydro-1,4-benzodioxin-6-yl)-1-oxo-1,2,3,4-tetrahydroisoquinoline-4-carboxylic acid | Calcd 501; found 501 |

Example 3

(3R,4R and 3S,4S)-2-(4'-acetamido-[1,1'-biphenyl]-4-yl)-3-(2,3-dihydrobenzo[b][1,4]dioxin-6-yl)-1-xo-1,2,3,4-tetrahydroisoquinoline-4-carboxylicacid (1-65)

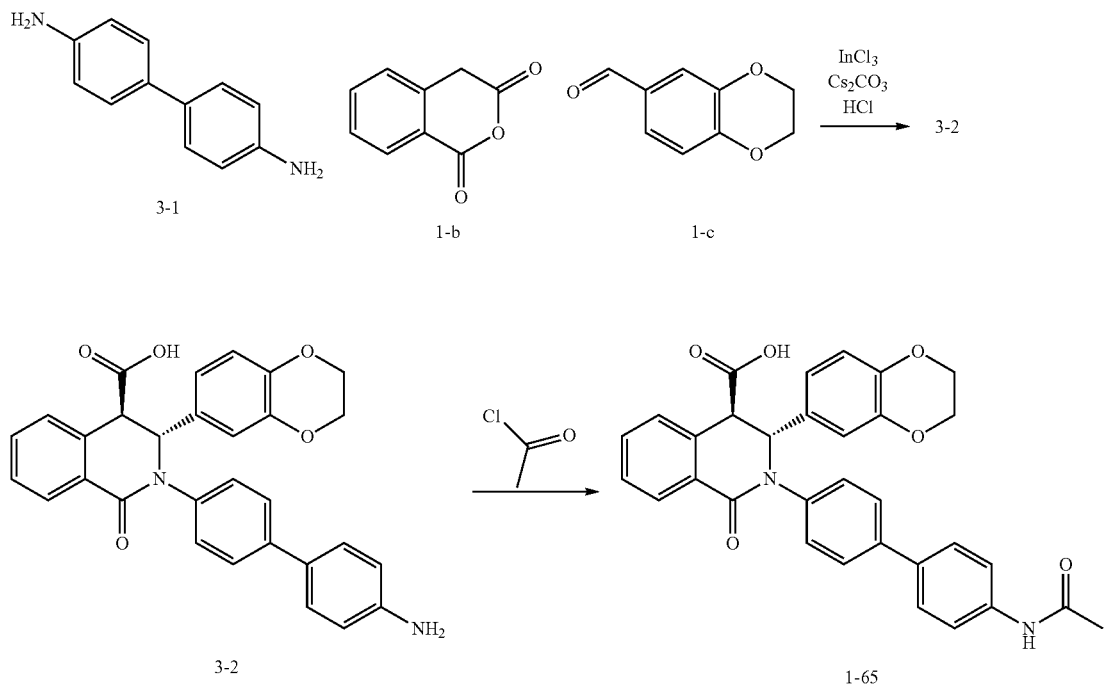

Step 1 (3R,4R and 3S,4S)-2-(4'-amino-[1,1'-biphenyl]-4-yl)-3-(2,3-dihydrobenzo[b][,4]dioxin-6-yl)-1-oxo-1,2,3,4-tetrahydroisoquinoline-4-carboxylic acid (1-65) was synthesized following an analogous procedure to that reported for Example 1. MS APCI calcd for $C_{30}H_{25}N_2O_5$ [M+H]$^+$ 493, found 493.

Step 2: To a solution of (3R,4R and 3S,4S)-2-(4'-amino-[1,1'-biphenyl]-4-yl)-3-(2,3-dihydrobenzo[b][1,4]dioxin-6-yl)-1-oxo-1,2,3,4-tetrahydroisoquinoline-4-carboxylic acid (3-2) (8.0 mg, 0.016 mmol) in dichloromethane (4 mL) was added acetyl chloride (2 µL, 0.03 mmol) and Hunig's base (0.014 mL, 0.081 mmol) at room temperature. The reaction mixture was stirred at room temperature for 1 hour. Sodium hydroxide (1.0M in water, 0.065 mL, 0.065 mol) was added and the reaction mixture was stirred for an additional 2 hours at room temperature. The reaction mixture was quenched with TFA (0.013 mL, 0.162 mmol), concentrated under reduced pressure, and directly purified by reverse phase chromatography on a C18 column ($CH_3CN/H_2O$ with 0.1% TFA) to afford (3R,4R and 3S,4S)-2-(4-acetamido-[1,1'-biphenyl]-4-yl)-3-(2,3-dihydrobenzo[b][1,4]dioxin-6-yl)-1-oxo-1,2,3,4-tetrahydroisoquinoline-4-carboxylic acid (1-65). LCMS ($C_{32}H_{27}N_2O_6$) (ES, m/z) 535 [M+H]$^+$. $^1$H NMR (499 MHz, DMSO-d$_6$) δ 13.15 (s, 1H), 10.04 (s, 1H), 8.00 (d, J=6.8 Hz, 1H), 7.68-7.63 (m, 4H), 7.60 (d, J=8.7 Hz, 2H), 7.53-7.49 (m, 1H), 7.47-7.43 (m, 1H), 7.38 (d, J=8.6 Hz, 2H), 733 (d, J=7.3 Hz, 1H), 6.76-6.62 (m, 3H), 5.63 (s, 1H), 4.23 (s, 1H), 4.14 (s, 4H), 2.06 (s, 3H).

Compound 1-66 found in Table 2, was prepared in a manner analogous to Example 3, using the appropriate amines from commercially available vendors.

Example 4

(3R,4R and 3S,4S)-2-(4'-acetamido-2-chloro-[1,1'-biphenyl]-4-yl)-3-(2,3-dihydrobenzo[b][1,4]dioxin-6-yl)-1-oxo-1,2,3,4-tetrahydroisoquinoline-4-carboxylicacid (1-67)

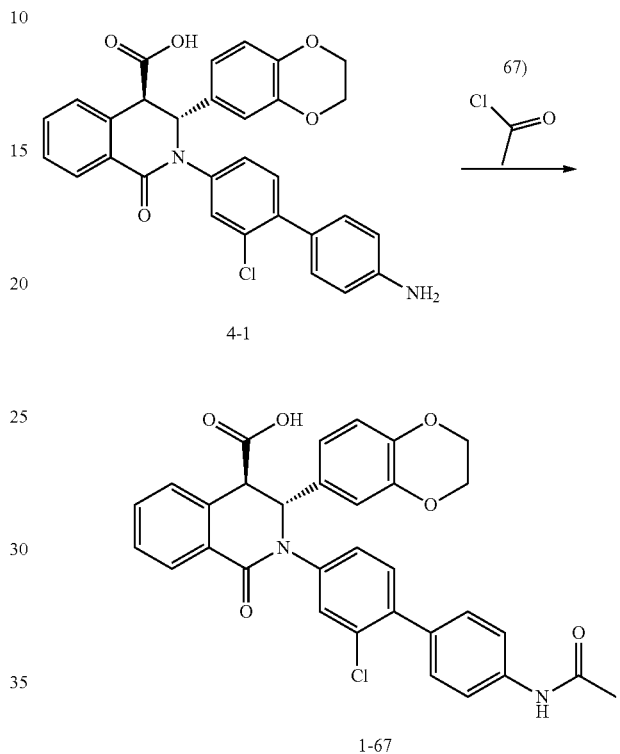

TABLE 2

| Ex. | Structure | Name | Exact Mass [M + H]+ |
|---|---|---|---|
| 1-66 | ![structure] | (3S,4S) and (3R,4R)-2-[4-(1-acetylpiperidin-4-yl)phenyl]-3-(2,3-dihydro-1,4-benzodioxin-6-yl)-1-oxo-1,2,3,4-tetrahydroisoquinoline-4-carboxylic acid | Calcd 527; found 527 |

Step 1: To a solution of (3R,4R and 3S,4S)-2-(4'-amino-2-chloro-[1,1'-biphenyl]-4-yl)-3-(2,3-dihydrobenzo[b][1,4]dioxin-6-yl)-1-oxo-1,2,3,4-tetrahydroisoquinoline-4-carboxylic acid (4-1) (10.0 mg, 0.016 mmol) in dichloromethane (1 mL) was added acetyl chloride (1 μL, 0.02 mmol) and N,N-diisopropylethylamine (Hunig's Base) (0.008 mL, 0.05 mmol) at room temperature. The reaction mixture was stirred at room temperature for 1 hour. Sodium hydroxide (1.0M in water, 0.094 ml, 0.094 mmol) was added and the reaction mixture was stirred for an additional 2 hours at room temperature. The reaction mixture was quenched with TFA (0.008 mL, 0.1 mmol), concentrated under reduced pressure, and directly purified by reverse phase chromatography on a C18 column. ($CH_3CN/H_2O$ with 0.1% TFA) to afford (3R,4R and 3S,4S)-2-(4'-acetamido-2-chloro-[1,1'-biphenyl]-4-yl)-3-(2,3-dihydrobenzo[b][1,4]dioxin-6-yl)-1-oxo-1,2,3,4-tetrahydroisoquinoline-4-carboxylic acid (1-67). LCMS ($C_{32}H_{26}ClN_2O_6$) (ES, m/z) 569 $[M+H]^+$. $^1$H NMR (499 MHz, DMSO-$d_6$) δ 13.18 (s, 1H), 10.08 (s, 1H), 8.00 (d, J=7.5 Hz, 1H), 7.65 (d, J=8.5 Hz, 2H), 7.57-7.49 (m, 2H), 7.48-7.41 (m, 2H), 7.40-7.32 (m, 4H), 6.77-6.63 (m, 3H), 5.68 (s, 1H), 4.25 (s, 1H), 4.15 (s, 4H), 2.07 (s, 3H).

Example Compounds 1-68 through 1-70, found in Table 3, were prepared in a manner analogous to Example 4, using the appropriate amines from commercially available vendors.

TABLE 3

| Ex. | Structure | Name | Exact Mass [M + H]+ |
|---|---|---|---|
| 1-68 | 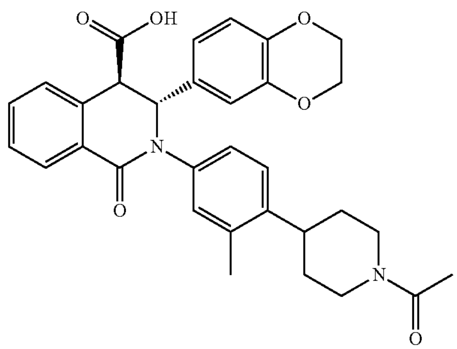 [SMILES: CC(=O)N1CCC(c2ccc(N3C(=O)c4ccccc4[C@@H](C(=O)O)[C@@H]3c3ccc4c(c3)OCCO4)cc2C)CC1] | (3R,4R) and (3S,4S)-2-[4-(1-acetylpiperidin-4-yl)-3-methylphenyl]-3-(2,3-dihydro-1,4-benzodioxin-6-yl)-1-oxo-1,2,3,4-tetrahydroisoquinoline-4-carboxylic acid | Calcd 541; found 541 |
| 1-69 | 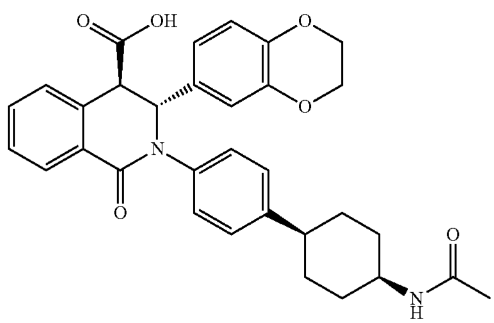 [SMILES: CC(=O)N[C@H]1CC[C@@H](c2ccc(N3C(=O)c4ccccc4[C@@H](C(=O)O)[C@@H]3c3ccc4c(c3)OCCO4)cc2)CC1] | (3R,4R) and (3S,4S)-2-{4-[cis-4-(acetylamino)cyclohexyl]phenyl}-3-(2,3-dihydro-1,4-benzodioxin-6-yl)-1-oxo-1,2,3,4-tetrahydroisoquinoline-4-carboxylic acid | Calcd 541; found 541 |
| 1-70 | 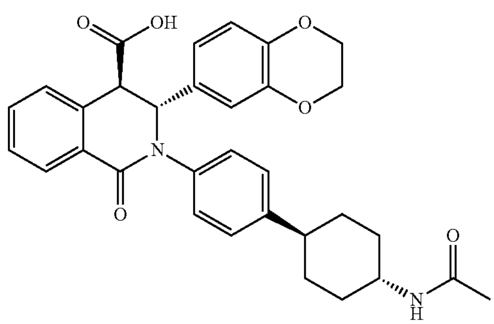 [SMILES: CC(=O)N[C@H]1CC[C@H](c2ccc(N3C(=O)c4ccccc4[C@@H](C(=O)O)[C@@H]3c3ccc4c(c3)OCCO4)cc2)CC1] | (3R,4R) and (3S,4S)-2-{4-[trans-4-(acetylamino)cyclohexyl]phenyl}-3-(2,3-dihydro-1,4-benzodioxin-6-yl)-1-oxo-1,2,3,4-tetrahydroisoquinoline-4-carboxylic acid | Calcd 541; found 541 |

Example 5

(3S,4S and 3R,4R)-2-(4-(tert-butyl)-3-chlorophenyl)-3-(2,3-dihydrobenzo[b][1,4]dioxin-6-yl)-N-methyl-1-oxo-1,2,3,4-tetrahydroisoquinoline-4-carboxamide (1-71)

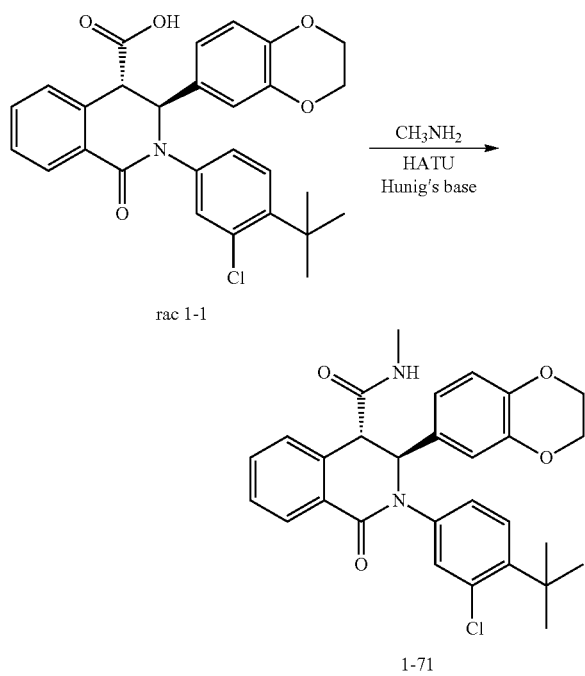

Step 1: Methylamine HCl (16 mg, 024 mmol), HATU (28 mg, 0.073 mmol) and Hunig's base (32 µl, 0.18 mmol) were added to a racemic mixture of 2-(4-(tert-butyl)-3-chlorophenyl)-3-(2,3-dihydrobenzo[b][1,4]dioxin-6-yl)-1-oxo-1,2,3,4-tetrahydroisoquinoline-4-carboxylic acid (1-1) (30 mg, 0.061 mmol) in DMF (0.20 mL). The reaction mixture was stirred at room temperature for 1.5 hours. The reaction mixture was diluted with EtOAc and water. The organic layer was separated and concentrated under reduced pressure. The residue was purified by silica gel chromatography [(25% ethanol in ethyl acetate) in hexanes] to afford (3S,4S and 3R,4R)-2-(4-(tert-butyl)-3-chlorophenyl)-3-(2,3-dihydrobenzo[b][1,4]dioxin-6-yl)-N-methyl-1-oxo-1,2,3,4-tetrahydroisoquinoline-4-carboxamide (1-71). LCMS ($C_{29}H_{30}ClN_2O_4$) (ES, m/z) 505 [M+H]$^+$. $^1$H NMR (600 MHz, DMSO-d$_6$) δ 8.05-7.87 (m, 2H), 7.49-7.29 (m, 4H), 7.24 (d, J=7.0 Hz, 1H), 7.11 (d, J=8.2 Hz, 1H), 6.71-6.65 (m, 2H), 6.59 (d, J=83 Hz, 1H), 5.34 (s, 1H), 4.11 (s, 4H), 3.96 (s, 1H), 2.59 (d, J=4.0 Hz, 3H), 1.39 (s, 9H).

Example Compounds 1-72 through 1-74 found in Table 4, were prepared in a manner analogous to Example 5, using the appropriate amines from commercially available vendors.

TABLE 4

| Ex. | Structure | Name | Exact Mass [M + H]+ |
|---|---|---|---|
| 1-72 | 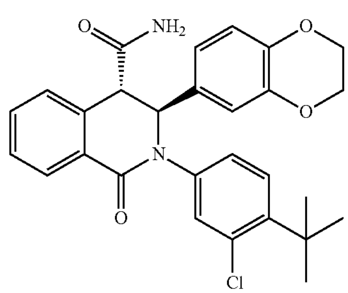 [SMILES: CC(C)(C)c1ccc(N2C(=O)c3ccccc3[C@H](C(N)=O)[C@H]2c2ccc3c(c2)OCCO3)cc1Cl] | (3S,4S) or (3R,4R)-2-(4-tert-butyl-3-chlorophenyl)-3-(2,3-dihydro-1,4-benzodioxin-6-yl)-1-oxo-1,2,3,4-tetrahydroisoquinoline-4-carboxamide | Calcd 491; found 491 |
| 1-73 | 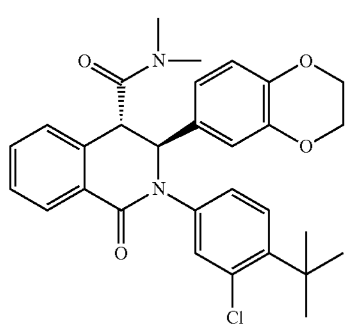 [SMILES: CN(C)C(=O)[C@H]1c2ccccc2C(=O)N(c2ccc(C(C)(C)C)c(Cl)c2)[C@@H]1c1ccc2c(c1)OCCO2] | (3S,4S) and (3R,4R)-2-(4-tert-butyl-3-chlorophenyl)-3-(2,3-dihydro-1,4-benzodioxin-6-yl)-N,N-dimethyl-1-oxo-1,2,3,4-tetrahydroisoquinoline-4-carboxamide | Calcd 519; found 519 |

TABLE 4-continued

| Ex. | Structure | Name | Exact Mass [M + H]+ |
|---|---|---|---|
| 1-74 | 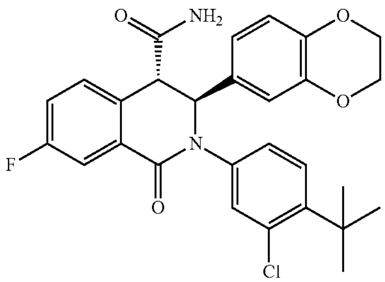 [SMILES: CC(C)(C)c1ccc(N2C(=O)c3cc(F)ccc3[C@H](C(N)=O)[C@H]2c2ccc3c(c2)OCCO3)cc1Cl] | (3S,4S) or (3R,4R)-2-(4-tert-butyl-3-chlorophenyl)-3-(2,3-dihydro-1,4-benzodioxin-6-yl)-7-fluoro-1-oxo-1,2,3,4-tetrahydroisoquinoline-4-carboxamide | Calcd 509; found 509 |

Example 6

(3S,4S and 3R,4R)-2-(4-(tert-butyl)-3-chlorophenyl)-3-(2,3-dihydrobenzo[b][1,4]dioxin-6-yl)-1-oxo-7-vinyl-1,2,3,4-tetrahydroisoquinoline-4-carboxylic acid (1-75)

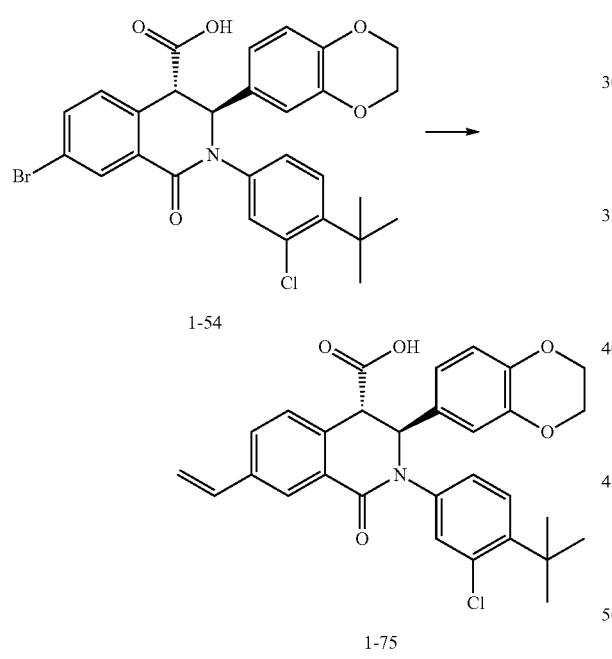

Step 1: (3S,4S and 3R,4R)-7-bromo-2-(4-(tert-butyl)-3-chlorophenyl)-3-(2,3-dihydrobenzo[b][1,4]dioxin-6-yl)-1-oxo-1,2,3,4-tetrahydroisoquinoline-4-carboxylic acid (1-54) (40 mg, 0.068 mmol), potassium vinyltrifluoroborate (14 mg, 0.10 mmol) and PdCl$_2$(dppf) (5 mg, 7 μmol) were combined and suspended in ethanol (0.7 mL). Triethylamine (0.024 mL, 0.17 mmol) was added to the mixture. The reaction mixture was heated to 90° C. for 1.5 hours. The reaction mixture was cooled to room temperature and then diluted with ethyl acetate and aqueous saturated sodium bicarbonate. The organic layer was separated, and the aqueous layer was extracted with ethyl acetate (3×). The organic layers were combined, washed with brine, dried over sodium sulfate, and concentrated under reduced pressure. The product residue was purified by reverse phase chromatography on a C18 column (CH$_3$CN/H$_2$O with 0.1/TFA) to afford (3S,4S and 3R,4R)-2-(4-(tert-butyl)-3-chlorophenyl)-3-(2,3-dihydrobenzo[b][,4]dioxin-6-yl)-1-oxo-7-vinyl-1,2,3,4-tetrahydroisoquinoline-4-carboxylic acid (1-75). LCMS (C$_{30}$H$_{29}$ClNO$_5$) (ES, m/z) 518 [M+H]$^+$. $^1$H NMR (600 MHz, DMSO-d$_6$) δ 13.11 (s, 1H), 7.98 (s, 1H), 7.61 (d, J=7.9 Hz, 1H), 7.46 (d, J=8.6 Hz, 1H), 7.38 (s, 1H), 7.28 (d, J=7.9 Hz, 1H), 7.20 (d, J=7.3 Hz, 1H), 6.78 (dd, J=17.6, 10.9 Hz, 1H), 6.69 (d, J=8.4 Hz, 1H), 6.64 (s, 1H), 6.60 (d, J=8.3 Hz, 1H), 5.86 (d, J=17.6 Hz, 1H), 5.57 (s, 1m), 5.30 (d, J=10.9 Hz, 1H), 4.18 (s, 1H), 4.11 (s, 4H), 1.39 (s, 9H).

Intermediate 2 tert-butyl (4'-amino-2'-chloro-[1,1'-biphenyl]-4-yl)carbamate (1-2)

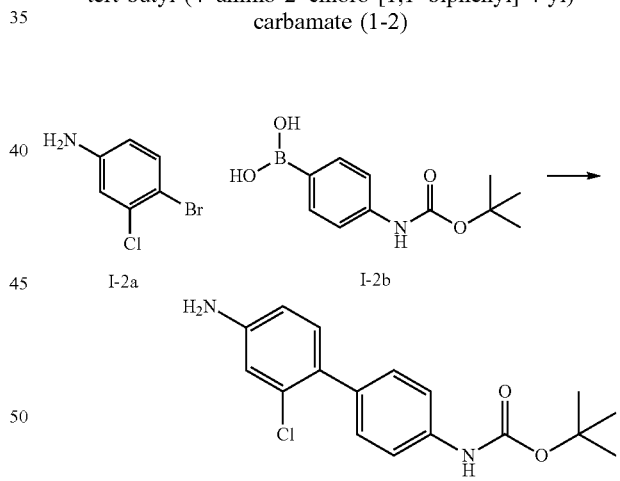

Step 1: A mixture of 4-bromo-3-chloroaniline (1-2a) (250 mg, 1.2 mmol) (4-((tert-butoxycarbonyl)amino)phenyl)boronic acid (1-2b) (287 mg, 1.21 mmol), Pd$_2$(dba)$_3$ (55 mg, 0.061 mmol), 2-Dicyclohexylphosphino-2',4',6'-triisopropylbiphenyl (X-phos) (58 mg, 0.12 mmol), and cesium carbonate (789 mg, 2.42 mmol) was degassed with argon for 3 minutes. Dioxane (4.0 mL) and water (0.4 mL) were added to the reaction mixture at room temperature. The reaction mixture was stirred for 5 minutes at room temperature while degassing with argon. The reaction mixture was then heated to 95° C. and stirred for 6 hours. The reaction mixture was then cooled to room temperature, diluted with ethyl acetate (100 mL), and washed with brine (25 mL). The organic layer was separated, dried over magnesium sulfate, filtered, and concentrated under reduced pressure to afford the crude product residue. The crude product residue was purified by silica gel chromatography (eluting ethyl acetate in hexanes) to afford tert-butyl (4'-amino-2'-chloro-[1,1'-biphenyl]-4-yl) carbamate (I-2) LCMS ($C_{17}H_{20}ClN_2O_2$) (ES, m/z) 319 [M+H]$^+$. $^1$H NMR (499 MHz, DMSO-$d_6$) δ 9.38 (s, 1H), 7.44 (d, J=8.4 Hz, 2H), 7.22 (d, J=8.6 Hz, 2H), 7.00 (d, J=8.3 Hz, 1H), 6.67 (d, J=2.2 Hz, 1H), 6.55 (dd, J=8.3, 2.2 Hz, 1H), 5.43 (s, 2H), 1.48 (s, 9H).

Intermediate 3

4-methyl-3,4-dihydro-2H-benzo[b][1,4]oxazine-6-carbaldehyde (I-3)

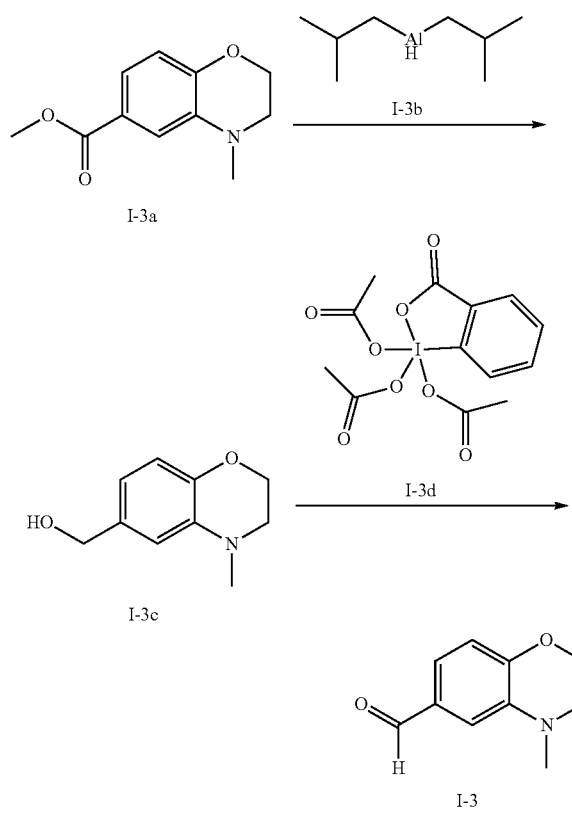

Step 1: DIBAL-H (I-3b) (1.0M in THF, 5.3 mL, 5.3 mmol) was added dropwise to a solution of methyl 4-methyl-3,4-dihydro-2H-benzo[b][1,4]oxazine-6-carboxylate (I-3a) (500 mg, 2.41 mmol) in tetrahydrofuran (5.0 mL) at 0° C. The reaction mixture was stirred at 0° C. for 1 hour and then allowed to warm to room temperature. The reaction mixture was then stirred at room temperature for 1 hour. The reaction mixture was then cooled to 0° C. and additional DIBAL-H (1.0M in THF, 6.0 mL, 6.0 mmol) was added. The reaction mixture was stirred at 0° C. for 1 hour and then allowed to warm to room temperature. The reaction mixture was then stirred for 1 hour at room temperature. The reaction mixture was cooled to 0° C. under a stream of argon gas. The mixture was quenched with saturated aqueous ammonium chloride solution under a stream of argon gas. Additional water was added (50 mL) and the mixture was diluted with ethyl acetate (50 mL) and methanol (50 mL). The resulting suspension was filtered and the filtrate was concentrated under reduced pressure, azeotroping several times with acetonitrile, to afford the crude product residue. The isolated residue was suspended in methanol and filtered. The filtrate was purified by silica gel chromatography (eluting [5% methanol in ethyl acetate] in dichloromethane) to afford (4-methyl-3,4-dihydro-2H-benzo[b][1,4]oxazin-6-yl) methanol (I-3c). LCMS ($C_{10}H_{14}NO_2$) (ES, m/z) 180 [M+H]$^+$. $^1$H NMR (499 MHz, DMSO-$d_6$) δ 6.64 (s, 1H), 6.58 (d, J=8.0 Hz, 1H), 6.50 (d, J=7.9 Hz, 1H), 4.94 (t, J=5.7 Hz, 1H), 4.34 (d, J=5.7 Hz, 2H), 4.23-4.16 (m, 2H), 3.24-3.16 (m, 2H), 2.81 (s, 3H).

Step 2: Dess-Martin periodinane (I-3d) (1270 mg, 3.00 mmol) was added portion wise to a solution of (4-methyl-3,4-dihydro-2H-benzo[b][1,4]oxazin-6-yl)methanol (I-3c) (430 mg, 2.4 mmol) in dichloromethane (5.0 mL) at 0° C. The reaction mixture was stirred at 0° C. for 1 hour and then allowed to warm to room temperature. The reaction mixture was then stirred for 1 hour at room temperature. The reaction mixture was quenched by the addition of saturated aqueous sodium bicarbonate solution (25 mL), and the mixture was then diluted with ethyl acetate (250 mL) and water (25 mL). The organic layer was separated, and the aqueous layer was washed with additional ethyl acetate (50 mL). The organic layers were combined, dried over magnesium sulfate, filtered, and concentrated under reduced pressure to afford the crude product residue. The crude product residue was purified by silica gel chromatography (eluting ethyl acetate in hexanes) to afford 4-methyl-3,4-dihydro-2H-benzo[b][1,4]oxazine-6-carbaldehyde (I-3). LCMS ($C_{10}H_{12}NO_2$) (ES, m/z) 178 [M+]$^+$. $^1$H NMR (499 MHz, DMSO-$d_6$) δ 9.77 (s, 1H), 7.19 (dd, J=8.1, 1.7 Hz, 1H), 7.14 (d, J=1.4 Hz, 1H), 6.86 (d, J=8.0 Hz, 1H), 4.36-4.29 (m, 2H), 3.31-3.25 (m, 2H), 2.89 (s, 3H).

Intermediate 4 tert-butyl 4-(4-amino-2-methylphenyl)piperidine-1-carboxylate (I-4)

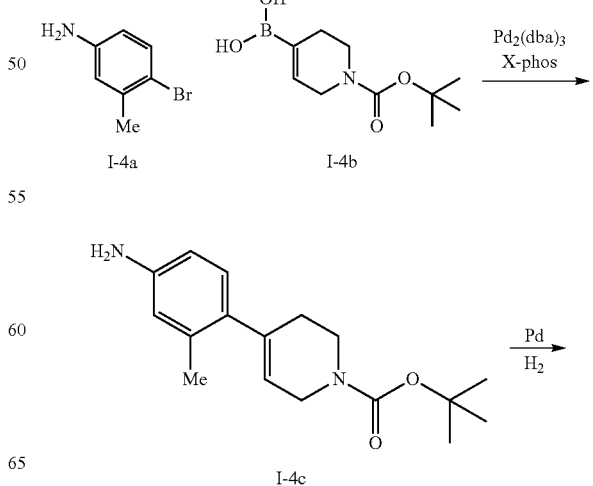

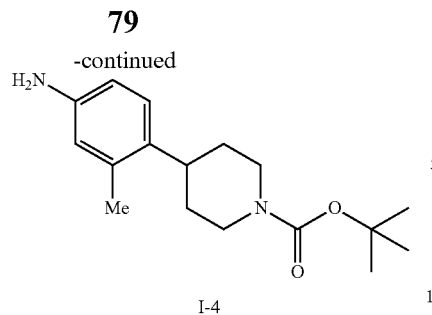

I-4

Step 1: A mixture of 4-bromo-3-methylaniline (I-4a) (1.23 g, 6.61 mmol), (1-(tert-butoxycarbonyl)-1,2,3,6-tetrahydropyridin-4-yl)boronic acid (I-4b) (1.50 g, 6.61 mmol), Pd$_2$(dba)$_3$ (0.30 g, 0.33 mmol), 2-Dicyclohexylphosphino-2'4'6'-triisopropylbiphenyl (X-phos) (0.32 g, 0.66 mmol), and cesium carbonate (431 g, 13.2 mmol) was degassed with argon for 3 minutes. Dioxane (10.0 mL) and water (1.0 mL) were added to the mixture at room temperature. The reaction mixture was stirred for 5 minutes while degassing with argon, and then the mixture was heated to 90° C. and stirred for 18 hours. The reaction mixture was cooled to room temperature, diluted with ethyl acetate (250 mL), and washed with brine (50 mL). The organic layer was separated, dried over magnesium sulfate, filtered, and concentrated under reduced pressure to afford the crude product residue. The crude product residue was purified by silica gel chromatography (eluting ethyl acetate in hexanes) to tert-butyl 4-(4-amino-2-methylphenyl)-5,6-dihydropyridine-(2H)-carboxylate (I-4c). LCMS (C$_{17}$H$_{25}$N$_2$O$_2$) (ES, m/z) 289 [M+H]$^+$. $^1$H NMR (499 MHz, DMSO-de) 6.73 (d, J=8.1 Hz, 1H), 6.36 (s, 1H), 6.35-6.30 (m, 1H), 5.42 (s, 1H), 4.92 (s, 2H), 3.90 (s, 2H), 3.48 (s, 2H), 2.20 (s, 2H), 2.09 (s, 3H), 1.42 (s, 9H).

Step 2: A flask containing tert-butyl 4-(4-amino-2-methylphenyl)-5,6-dihydropyridine-1(2H)-carboxylate (I-4c) (1.68 g, 5.83 mmol) and palladium on carbon (0.310 g, 0.291 mmol) was degassed with argon for 5 minutes. Ethanol (20 mL) and hydrochloric acid (370 in water, 0.96 mL, 12 mmol) were added under a stream of argon. The headspace above the reaction mixture was evacuated by vacuum and backfilled with hydrogen gas. The reaction mixture was stirred under a hydrogen atmosphere for 18 hours at room temperature. The reaction mixture was filtered through Celite™ and washed with methanol. The filtrate was concentrated under reduced pressure to afford the crude product residue. The crude product residue was suspended in ethyl acetate (250 mL) and diluted with saturated aqueous sodium bicarbonate solution (50 mL). The mixture was stirred until all solids had dissolved. The organic layer was separated and washed with brine (25 mL). The organic layer was separated, dried over magnesium sulfate, filtered, and concentrated under reduced pressure to afford the crude product residue. The crude product residue was purified by silica gel chromatography (eluting ethyl acetate in hexanes) to afford the product. A portion of the isolated product was further purified by reverse phase HPLC (eluting acetonitrile in water with 0.1% TFA modifier) to afford tert-butyl 4-(4-amino-2-methylphenyl)piperidine-1-carboxylate (I-4) LCMS (C$_{17}$H$_{27}$N$_2$O$_2$—C$_4$H$_8$) (ES, m/z) 235 [M+H-tBu]$^+$. $^1$H NMR (499 MHz, DMSO-d$_6$) δ 9.06 (s, 2H), 7.21 (d, J=8.1 Hz, 1H), 6.98-6.93 (m, 2H), 4.06 (s, 2H), 2.84 (t, J=11.9 Hz, 2H), 2.30 (s, 3H), 1.64 (d, J=12.8 Hz, 2H), 1.48-1.40 (m, 3H), 1.41 (s, 9H)

Intermediate 5 tert-butyl ((cis)-4-(4-aminophenyl)cyclohexyl)carbamate and tert-butyl ((trans)-4-(4-aminophenyl)cyclohexyl)carbamate (I-5)

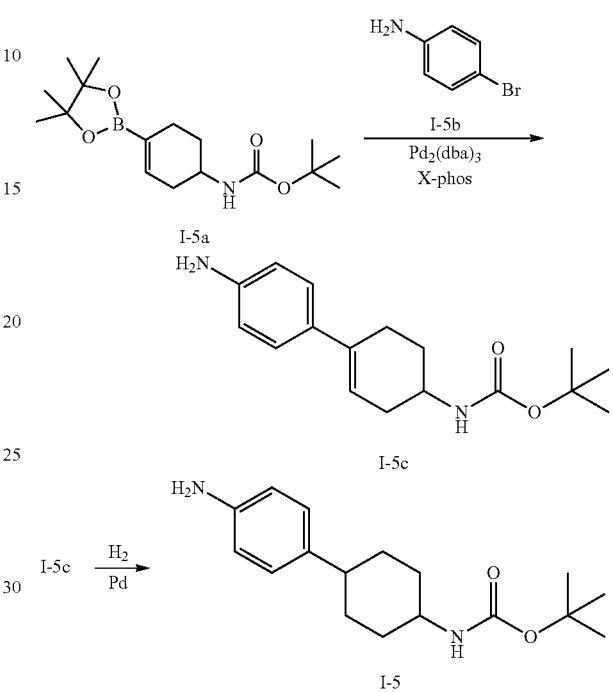

Step 1: A mixture of 4-bromoaniline (I-5b) (500 mg, 2.91 mmol), tert-butyl (4-(4,4,5,5-tetramethyl-1,3,2-dioxaborolan-2-yl)cyclohex-3-en-1-yl)carbamate (1-5a) (940 mg, 2.91 mmol), Pd$_2$(dba)$_3$ (133 mg, 0.145 mmol), X-phos (139 mg, 0.291 mmol), and cesium carbonate (1.9 g, 5.8 mmol) was degassed with argon for 3 minutes. Dioxane (8.0 mL) and water (0.8 mL) were added to the mixture at room temperature. The reaction mixture was stirred for 5 minutes while degassing with argon, and then the reaction mixture was heated to 90° C. and stirred for 18 hours. The reaction mixture was cooled to room temperature, diluted with ethyl acetate (250 ml), and washed with brine (50 mL). The organic layer was separated, dried over magnesium sulfate, filtered, and concentrated under reduced pressure to afford the crude product residue. The crude product residue was purified by silica gel chromatography (eluting ethyl acetate in hexanes) to afford tert-butyl (4'-amino-2,3,4,5-tetrahydro-[1,1'-biphenyl]-4-yl)carbamate (I-5c) LCMS (C$_{17}$H$_{25}$N$_2$O$_2$) (ES, m/z) 289 [M+H]$^+$. $^1$H NMR (499 MHz, DMSO-d$_6$) δ 7.07 (d, J=8.5 Hz, 2H), 6.83-6.74 (M, 1H), 6.48 (d, J=8.6 Hz, 2H), 5.79 (s, 1H), 5.04 (s, 2H), 3.50-3.42 (m, 1H), 2.45-2.25 (m, 3H), 2.07-1.94 (m, 1H), 1.92-1.81 (m, 1H), 1.53-1.45 (m, 1H), 1.39 (s, 9H).

Step 2: A flask containing tert-butyl (4'-amino-2,3,4,5-tetrahydro-[1,1'-biphenyl]-4-yl)carbamate (1-4c) (580 mg, 2.0 mmol) and palladium on carbon (107 mg, 0.101 mmol) was degassed with argon for 5 minutes. Ethanol (20 ml) and hydrochloric acid (37% in water, 0.50 mL, 6.0 mmol) were added under a stream of argon. The headspace above the reaction mixture was evacuated by vacuum and backfilled with hydrogen gas. The reaction mixture was stirred under a hydrogen atmosphere for 6 hours at room temperature. The reaction mixture was filtered through Celite™ and washed with methanol. The filtrate was concentrated under reduced pressure to afford the crude product. The crude product was suspended in ethyl acetate (250 mL) and diluted with saturated aqueous sodium bicarbonate solution (50 mL). The mixture was stirred until all solids had dissolved. The organic layer was separated and washed with brine (25 mL). The organic layer was separated, dried over magnesium sulfate, filtered, and concentrated under reduced pressure to afford the crude product residue. The crude product residue was purified by silica gel chromatography (eluting ethyl acetate in hexanes) to afford the product as a mixture of cis/trans isomers. The isolated product was further purified by reverse phase HPLC (eluting acetonitrile in water with 0.1% TFA modifier) to afford tert-butyl (4-(4-aminophenyl) cyclohexyl)carbamate as a mixture of cis/trans isomers. tert-Butyl (4-(4-aminophenyl)cyclohexyl)carbamate 2,2,2-trifluoroacetate (1-5) was separated into pure stereoisomers (Chiralpak® AS-H, 21×250 mm, eluting methanol+0.25% dimethyl ethyl amine in $CO_2$) to afford two peaks eluting at 2.58 minutes and 4.00 minutes.

Peak 1: tert-butyl ((cis)-4-(4-aminophenyl)cyclohexyl)carbamate: LCMS ($CH_{17}H_{26}N_2O_2$+Na) (ES, m/z) 313 [M+Na]$^+$. $^1$H NMR (499 MHz, DMSO-$d_6$) δ 6.96-6.90 (m, 3H), 6.47 (d, J=7.8 Hz, 2H), 4.77 (s, 2H), 3.66 (s, 1H), 2.31-2.25 (m, 1H), 1.75-1.62 (m, 4H), 1.58-1.42 (m, 4H), 1.40 (s, 9H).

Peak 2: tert-butyl ((trans)-4-(4-aminophenyl)cyclohexyl) carbamate: LCMS ($C_{17}H_{27}N_2O_2$—$C_4H_8$) (ES, m/z) 235 [M+H-tBu]$^+$. $^1$H NMR (499 MHz, DMSO-$d_6$) δ 6.85 (d, J=8.3 Hz, 2H), 6.73 (d, J=7.9 Hz, 1H), 6.46 (d, J=8.2 Hz, 2H), 4.79 (s, 2H), 3.27-3.19 (m, 1H), 2.26-2.18 (m, 1H), 1.82 (d, J=11.0 Hz, 2H), 1.70 (d, J=12.0 Hz, 2H), 1.42-1.31 (m, 2H), 1.38 (s, 9H), 1.29-1.19 (M, 2H)

Example 7

(3R,4R or 3S,4S)-2-(4-(tert-butyl)-3-chlorophenyl)-3-(2,3-dihydrobenzo[b][1,4]dithiin-6-yl)-1-oxo-1,2,3,4-tetrahydroisoquinoline-4-carboxylic acid (1-76)

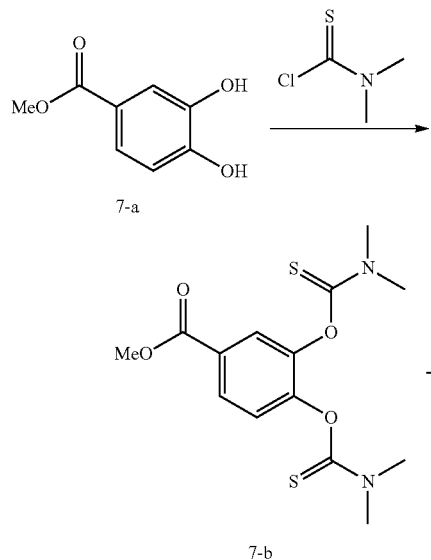

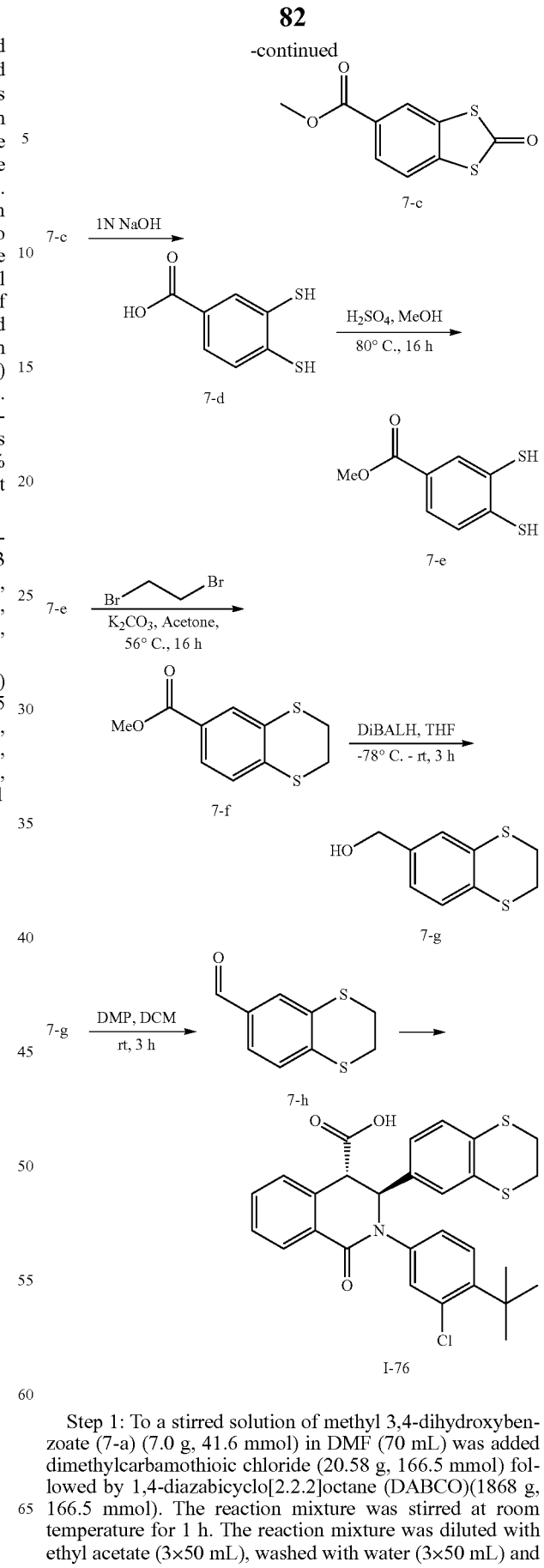

Step 1: To a stirred solution of methyl 3,4-dihydroxybenzoate (7-a) (7.0 g, 41.6 mmol) in DMF (70 mL) was added dimethylcarbamothioic chloride (20.58 g, 166.5 mmol) followed by 1,4-diazabicyclo[2.2.2]octane (DABCO)(1868 g, 166.5 mmol). The reaction mixture was stirred at room temperature for 1 h. The reaction mixture was diluted with ethyl acetate (3×50 mL), washed with water (3×50 mL) and brine solution. The mixture was dried over sodium sulfate, filtered and concentrated under reduced pressure. To the crude compound was added ethanol (100 mL) and kept at room temperature for 16 h. The resulting solid was filtered and dried to afford methyl 3,4-bis((dimethylcarbamothioyl)oxy)benzoate (7-b). MS ESI calcd for $C_{14}H_{19}N_2O_4S_2$ [M+H]$^+$ 343 found 343. $^1$H NMR (400 MHz, CDCl$_3$) δ57.99 (dd, J=8.4 Hz, 2.0 Hz, 1H) 7.85 (d, J=2.0 Hz, 1H), 7.23 (d, J=8.4 Hz, 1H), 3.90 (s, 3H), 3.43 (d, J=1.7 Hz, 6H), 3.30 (d, J=2.6 Hz, 6H)

Step 2: To the compound methyl 3,4-bis ((dimethylcarbamothioyl)oxy)benzoate (7-b) (4.5 g, 13.1 mmol) was added diphenyl ether (145 mL). The reaction mixture was stirred at 290° C. for 1.5 h with vigorous stirring. The reaction mixture was cooled to room temperature, and then purified by column chromatography on silica by using 6% ethylacetate/hexanes as eluent to afford methyl 2-oxobenzo[d][1,3]dithiole-5-carboxylate (7-c). MS ESI calcd for $C_9H_7O_3S_2$ [M+H]$^+$ 226 found 226.

Step 3: To the compound methyl 2-oxobenzo[d][1,3]dithiole-5-carboxylate (7-c) (1.2 g, 5.30 mmol) was added IM NaOH aqueous solution (50 mL) The reaction mixture was stirred at 75° C. for 4 h. The reaction mixture was cooled to 0° C., acidified by using 1N HCl (100 mL). The resulting solid was filtered and dried to afford 3,4-dimercaptobenzoic acid (7-d). MS ESI calcd for $C_7H_7O_2S_2$ [M+H]$^+$ 186 found 186.

Step 4: To a stirred solution of 3,4-dimercaptobenzoic acid (7-d) (780 mg, 4.2 mmol) in methanol (15 mL) was added 2 drops of sulfuric acid. The solution was allowed to stir at 75° C. for 16 h. The reaction mixture then was concentrated. The resulting residue was basified by using saturated NaHCO$_3$ solution, extracted with ethyl acetate (30 mL), washed with water (10 mL) and brine solution. The organic layer was dried over sodium sulfate, filtered and concentrated under reduced pressure to afford methyl 3,4-dimercaptobenzoate (7-e). MS ESI calcd for $C_8H_9O_2S_2$ [M+H]$^+$ 201 found 201.

Step 5: To a stirred solution of methyl 3,4-dimercaptobenzoate (7-e) (750 mg, 3.75 mmol) in acetone (20 mL) was added potassium carbonate (1.55 g, 11.25 mmol) followed by 1,2-dibromoethane (1.76 g, 9.37 mmol). The reaction mixture was stirred at 60° C. for 2 h. The reaction mixture was cooled to room temperature, filtered through Celite™, the filtrate was concentrated. The crude compound was purified by column chromatography on silica by using 10% ethylacetate/hexanes as eluent to afford methyl 2,3-dihydrobenzo[b][1,4]dithiine-6-carboxylate (7-f). MS ESI calcd for $C_{10}H_{11}O_2S_2$ [M+H]$^+$ 227 found 227. $^1$H NMR (400 MHz, CDCl$_3$) 7.81 (s, 11H), 7.61 (dd, J=8.0 Hz, 1.6 Hz, 1H), 7.17 (d, J=8.2 Hz, 1H), 3.88 (s, 3H), 3.37-3.23 (m, 4H).

Step 6: To a stirred solution of methyl 2,3-dihydrobenzo[b][1,4]dithiine-6-carboxylate (7-f) (350 mg, 1.54 mmol) in anhydrous dichloromethane (15 mL) at −78° C., DiBAL-H (3.5 mL, 2.32 mmol) was added. The reaction mixture was stirred at −78° C. for 1.5 h, then slowly warmed to room temperature and stirred for an additional 1 h. The reaction mixture was quenched with ammonium chloride solution, extracted with dichloromethane (30 mL), washed with water and brine solution. The organic layer was dried over sodium sulfate, filtered and concentrated under reduced pressure. The crude compound was purified by column chromatography on silica by using 20% ethylacetate/hexanes as eluent to afford (2,3-dihydrobenzo[b][1,4]dithiin-6-yl)methanol (7-g). MS ESI calcd for $C_9H_{11}OS_2$ [M+H]$^+$ 199 found 199.

$^1$H NMR (400 MHz, CDCl$_3$) δ7.17 (s, 1H), 7.14 (d, J=8.0 Hz, 1H), 6.99 (d, J=8.0 Hz, 1H), 4.58 (d, J=5.6 Hz, 2H), 3.26 (s, 4H), 1.60 (s, 1H).

Step 7: To a stirred solution of (2,3-dihydrobenzo[b][1,4]dithiin-6-yl)methanol (7-g) (240 mg, 1.21 mmol) in dichloromethane (10 mL) was added dessmartin periodinane (DMP) (770 mg, 1.81 mmol). The reaction mixture was stirred at room temperature for 3 h. Then the reaction mixture was diluted with DCM (30 mL), washed with aqueous Na$_2$S$_2$O$_4$ solution, aqueous NaHCO$_3$ solution, water and brine. The organic layer was dried over sodium sulfate, filtered and concentrated under reduced pressure. The crude compound was purified by column chromatography on silica by using 6% ethylacetate/hexanes as eluent to afford 2,3-dihydrobenzo[b][1,4]dithiine-6-carbaldehyde (7-h). MS ESI calcd for $C_9H_9OS_2$[M+H]$^+$ 197 found 197. $^1$H NMR (400 MHz CDCl$_3$) δ9.84 (s, 1H), 7.61 (d, J=1.6 Hz, 1H), 7.46 (dd, J=8.0 Hz, 1.6 Hz, 1H), 7.27 (s, 1H), 3.39-3.25 (m, 4H).

Step 8: To the compound 2-(carboxymethyl)benzoic acid (60 mg, 0.33 mmol), 4-(tert-butyl)-3-chloroaniline (61 mg, 0.33 mmol), 2,3-dihydrobenzo[b][1,4]dithiine-6-carbaldehyde (7-h) (65 mg, 0.33 mmol) was added toluene (3.0 mL), kept in a dean-stark apparatus, stirred at 140° C. for 24 h. To the reaction mixture was added ethyl acetate (15 mL). The mixture then was washed with water and brine solution. The organic layer was dried over sodium sulfate, filtered and concentrated under reduced pressure. The crude compound was purified by reverse phase column chromatography by using 70% acetonitrile/water as eluent to afford 2-(4-(tert-butyl)-3-chlorophenyl)-3-(2,3-dihydrobenzo[b][1,4]dithiin-6-yl)-1-oxo-1,2,3,4-tetrahydroisoquinoline-4-carboxylic acid. $^1$H NMR (400 MHz, DMSO-d$_6$) δ13.14 (s, 1H), 7.98 (dd, J=7.8 Hz, 1.6 Hz, 1H), 7.54-7.41 (m, 4H), 7.32 (d, J=7.4 Hz, 1H), 7.21 (dd, J=8.6 Hz, 2.2 Hz, 1H), 7.00 (d, J=8.0 Hz, 2H), 6.79 (dd, J=8.6 Hz, 2.2 Hz, 1H), 5.63 (s, 1H), 3.21 (s, 4H), 1.43 (s, 9H).

Step 9: Isomers were separated by SFC, IA column eluting with 15% MeOH and CO$_2$ to give isomer I 1-76 (fast eluting) $^1$H NMR (400 MHz, CDCl$_3$) δ 8.11 (d, J=8.2 Hz, 1H), 7.41-7.32 (m, 4H), 7.15-7.10 (m, 2H), 6.99-6.92 (m, 2H), 6.70 (dd, J=8.0, 1.6 Hz, 1H), 5.48 (s, 1H), 3.88 (s, 1H), 3.19 (s, 4H), 1.41 (s, 9H). MS ESI calcd for $C_{28}H_{26}ClNO_3S_2$ [M+H]$^+$ 524 found 524.

Example 8

(3R,4R or 3S,4S)-2-(4-(tert-butyl)-3-chlorophenyl)-3-(2,3-dihydrobenzo[b][1,4]oxathiin-6-yl)-1-oxo-1,2,3,4-tetrahydroisoquinoline-4-carboxylic acid (1-77)

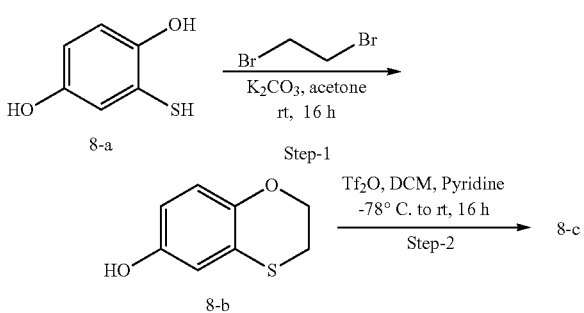

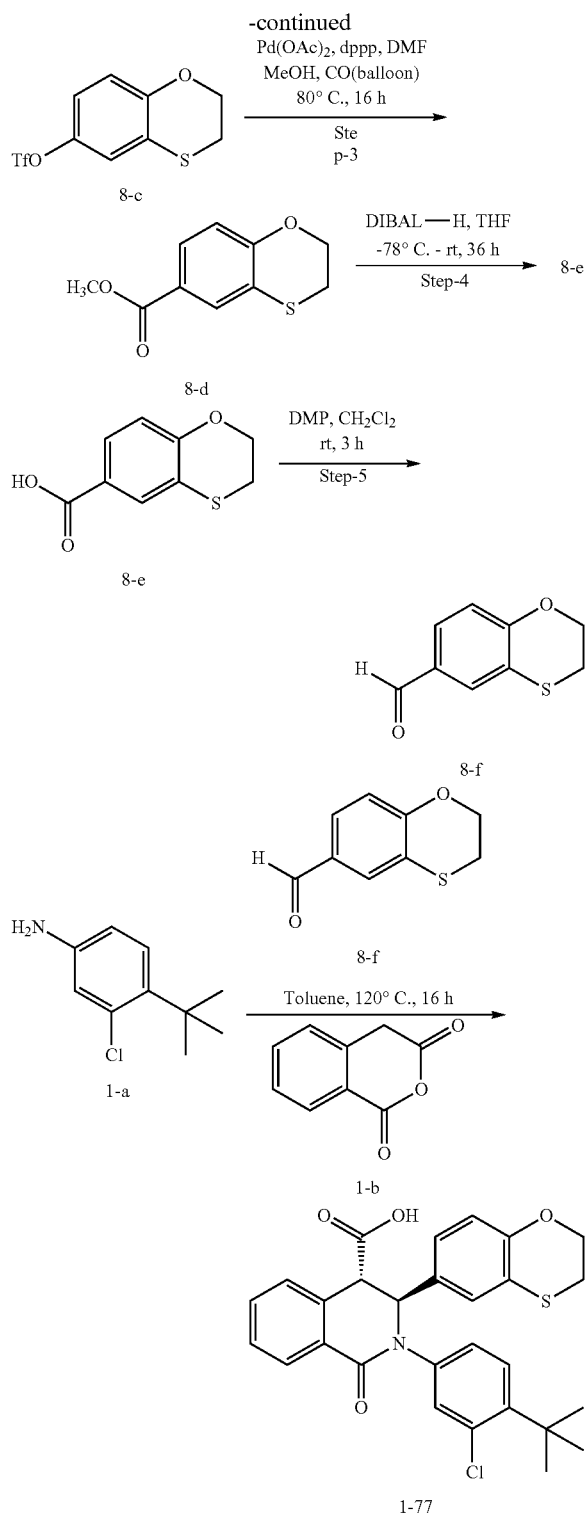

Step 1: To a stirred solution of 1,2-dibromoethane (1.51 mL, 17.58 mmol in acetone (90 ml), potassium carbonate (4.86 g, 35.2 mmol) was added at RT. To this reaction mixture, 2-mercaptobenzene-1,4-diol (8-a) (2.50 g, 1.58 mmol) in acetone (30 ml) was added slowly over period of 20 minutes at RT. The reaction mixture was stirred at RT for 16 hours and then filtered through Celite™ bed and the solvent was concentrated under reduced pressure. The residue was diluted with EtOAc (150 mL) and water (50 mL), and the layers were separated. The organic fraction was washed with brine (100 mL), dried ($Na_2SO_4$), and filtered. The filtrate then was concentrated under reduced pressure. The residue was purified by column chromatography on silica (0 to 60 EtOAc/Hexanes) to afford 2,3-dihydrobenzo[b][1,4]oxathiin-6-ol (8-b). $^1H$ NMR (400 MHz, $CDCl_3$) δ 669 (d, J=8.8 Hz, 1H), 6.53 (d, J=3.0 Hz, 1H), 6.49-6.45 (m, 1H), 4.70 (S, 1H), 4.36-4.32 (m, 2H), 3.13-3.08 (m, 2H)

Step 2: To a stirred solution of 2,3-dihydrobenzo[b][1,4]oxathiin-6-ol (8-b) (50 mg, 0.297 mmol) in DCM (1 ml), pyridine (0.048 ml, 0.594 mmol) and trifluoromethane sulfonic anhydride ($Tf_2O$) (0.065 ml, 0.386 mmol) were added at −78° C. The reaction mixture was stirred at RT for 16 hours under nitrogen atmosphere. The reaction mixture then was diluted with DCM (10 mL) and water (10 mL), and the layers separated. The organic layer washed with aq solution of 1N HCl (10 mL) and aq sat $NaHCO_3$ solution (10 mL) and brine solution. The organic layer was dried over $Na_2SO_4$, filtered and concentrated under reduced pressure to afford 2,3-dihydrobenzo[b][1,4]oxathiin-6-yl trifluoromethanesulfonate (8-c). $^1H$ NMR (400 MHz, $CDCl_3$) δ 6.96 (d, J=2.8 Hz, 1H), 6.89-6.81 (m, 2H), 4.45-4.38 (m, 2H), 3.16-3.10 (m, 2H).

Step 3: To a stirred solution of 2,3-dihydrobenzo[b][1,4]oxathiin-6-yl trifluoromethane sulfonate (8-) (100 mg, 0.333 mmol) in DMF (1.2 ml) and MeOH (0.6 ml), $Et_3N$ (0.186 ml, 1332 mmol), $Pd(OAc)_2$ (14.95 ng, 0.067 mmol) and 1,3-bis(diphenylphosphino)propane (dppp) (27.5 mg, 0.067 mmol) were added at RT under nitrogen atmosphere. The reaction mixture was purged with carbon monoxide (balloon) for 30 minutes and then the vessel was sealed and the reaction was stirred for 16 hours at 80° C. under carbon monoxide atmosphere. The mixture was cooled, filtered through a Celite™ bed, washed with EtOAc (20 mL) and water (15 mL), and the layers separated. The organic layer washed with brine solution. The organic layer was dried over $Na_2SO_4$, filtered and concentrated under reduced pressure. The residue was purified by column chromatography on silica (0 to 60% EtOAc/Hexanes) to afford methyl 2,3-dihydrobenzo[b][1,4]oxathiine-6-carboxylate (8-d). $^1H$ NMR (400 MHz, $CDCl_3$) δ 7.77 (d, J=2.1 Hz, 1H), 7.67-7.63 (m, 1H), 6.83 (d, J=8.5 Hz, 1H), 4.49-4.44 (m, 2H) 3.86 (S, 3H), 3.16-3.08 (M, 2H).

Step 4: To a stirred solution of methyl 2,3-dihydrobenzo[b][1,4]oxathiine-6-carboxylate (8-d) (500 mg, 2.378 mmol) in THF (20 mL), DIBAL-H (IM in THF, 7.13 ml, 7.13 mmol) was added at −78° C. under nitrogen atmosphere. The reaction mixture was stirred for 36 hours RT under nitrogen atmosphere. The reaction mixture was quenched with sat. $NH_4Cl$ (30 mL) and the mixture was extracted with EtOAc (2×30 mL). The combined organic fractions were washed with brine (30 mL), dried ($Na_2SO_4$), and filtered. The filtrate was concentrated under reduced pressure. The residue was purified by column chromatography on silica (0 to 60% EtOAc/H exanes) to afford (2,3-dihydrobenzo[b][1,4]oxathiin-6-yl)methanol (8-e). $^1H$ NMR (400 MHz, $CDCl_3$) δ 7.03-7.01 (m, 1H), 6.96-6.91 (m, 1H), 6.78 (d, J=8.3 Hz, 1H), 4.50-4 (s, 2H), 4.40-434 (m, 2H), 3.13-3.07 (m, 2H) 2.06 (brs, 1H).

Step 5: To a stirred solution of (2,3-dihydrobenzo[b][1,4]oxathiin-6-yl)methanol (8-e) (410 mg, 2.250 mmol) in DCM (12 ml), Dess-Martin periodinane (DMP) (1.431 g, 3.37 mmol) was added under $N_2$ nitrogen atmosphere at 0° C. The reaction mixture was stirred for 3 hours at RT. The reaction mixture was diluted with DCM (20 mL) and water (20 mL), and then the layers were separated. The organic layer washed with aq. solution of sodium thiosulfate (20 mL) and aq. sat aq NaHCO$_3$ solution (20 mL) and brine. The organic layer was dried over Na$_2$SO$_4$, filtered and concentrated under reduced pressure. The residue was purified by column chromatography on silica (0 to 60% EtOAc/Hexanes) to afford 2,3-dihydrobenzo[b][1,4]oxathiine-6-carbaldehyde (8-f). NMR (400 MHz, CDCl$_3$) 9.80 (s, 1H) 7.59 (d, J=2.0 Hz, 1H), 7.53-7.49 (m, 1H), 6.92 (d, J=8.2 Hz, 1H), 4.52-4.47 (m, 2H), 3.17-3.11 (m, 2H).

Step 6: To a stirred solution of 4-(tert-butyl)-3-chloroaniline (1-a) (100 mg, 0.544 mmol) in toluene (5 ml), homophthalic anhydride (1-b) (88 mg, 0.544 mmol) and 2,3-dihydrobenzo[b][1,4]oxathiine-6-carbaldehyde (8-f) (98 mg, 0.544 mmol) were added under N$_2$ nitrogen atmosphere at RT. The reaction mixture was refluxed for 16 hours at 120° C. using a dean-stark apparatus. The reaction mixture was concentrated under reduced pressure. The residue was purified by column chromatography on silica (0 to 60% EtOAc/Hexanes) to afford (3R,4R)-2-(4-(tert-butyl)-3-chlorophenyl)-3-(2,3-dihydrobenzo[b][1,4]oxathiin-6-yl)-1-oxo-1,2,3,4-tetrahydroisoquinoline-4-carboxylic acid (1-77 racemic). MS ESI calcd for C$_{28}$H$_{26}$ClNO$_4$S [M+H]$^+$ 508, found 508, 510.

Step 7: (3R,4R)-2-(4-(tert-butyl)-3-chlorophenyl)-3-(2,3-dihydrobenzo[b][1,4]oxathiin-6-yl)-1-oxo-1,2,3,4-tetrahydroisoquinoline-4-carboxylic acid 130 mg, 0.256 mmol) (Racemic mixture) was separated by chiral SFC (IA column, 25% MeOH in 0.1% TFA/CO$_2$) to afford (3R,4R)-2-(4-(tert-buty)-3-chlorophenyl)-3-(2,3-dihydrobenzo[b][1,4]oxathiin-6-yl)-1-oxo-1,2,3,4-tetrahydroisoquinoline-4-carboxylic acid. (Enantiomer A, first eluting) 1-77: MS ESI calcd for C$_{28}$H$_{26}$ClNO$_4$S [M+H]$^+$ 508, found 508, 510. $^1$H NMR (400 MHz, CDCl$_3$) δ 8.10-8.05 (m, 1H) 7.54-7.42 (m, 3H), 738 (d, J=2.2 Hz, 1H), 7.32-7.28 (m, 1H), 7.18-7.14 (m, 1H), 6.79-6.77 (m, 1H), 6.74-6.69 (m, 1H), 6.65-661 (m, 1H), 5.51 (s, 1H), 4.32-4.24 (m, 2H), 4.10 (s, 1H), 4.08-4.01 (m, 2H), 1.46 (s, 9H).

Example 9

(3R,4R or 3S,4S)-2-(4-(tert-butyl)-3-chlorophenyl)-3-(2,3-dihydrobenzo[b][1,4]oxathiin-7-yl)-1-oxo-1,2,3,4-tetrahydroisoquinoline-4-carboxylic acid (1-78)

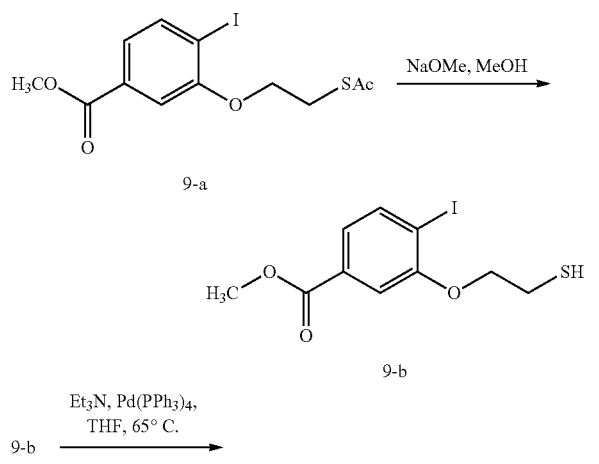

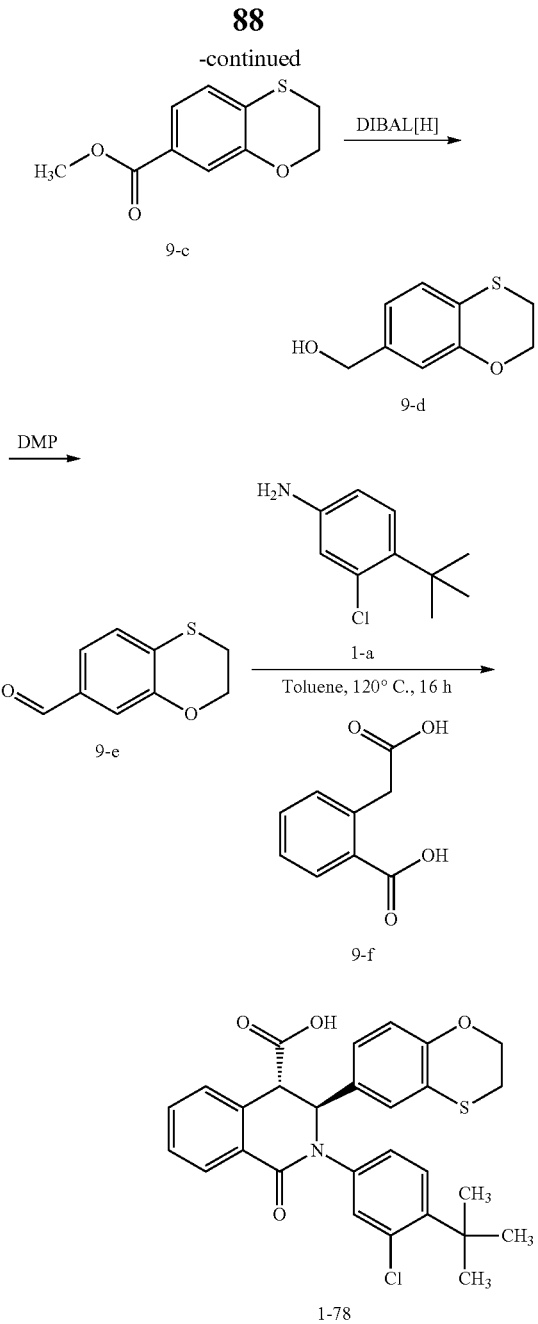

Step 1: To solution of methyl 3-(2-(acetylthio)ethoxy)-4-iodobenzoate (9-a) (1 g, 2.63 mmol) [prepared from methyl 3-hydroxy-4-iodobenzoate as reported in Organic Letters, 15(3), 550-553; 2013] in MeOH (2 ml) was added sodium methoxide (NaOMe) (213 mg, 3.95 mmol). The reaction was stirred for 1 hour at room temperature and then quenched with 1 N aqueous HCl (5.0 mL). The reaction mixture was extracted with EtOAc (3×20 ml) and the organic layer was washed with brine (5.0 mL). The organic layer was dried over anhydrous Na$_2$SO$_4$, filtered, and concentrated to dryness. The crude product was purified by column chromatography on silica gel (4 g, 0 to 10% EtOAc/Hexane) to afford methyl 4-iodo-3-(2mercaptoethoxy)benzoate (9-b). (400 MHz, CDCl$_3$) δ 7.85 (d, J=9.5 Hz, 1H), 7.43-7.37 (m, 2H), 4.26 (d, J=6.0 Hz, 2H), 3.91 (s, 3H), 2.93 (d, J=6.0 Hz, 2H).

Step 2: To a solution of methyl 4-iodo-3-(2-mercaptoethoxy)benzoate (9-b) (450 mg, 1.331 mmol) in THF (1.5 ml) was added trimethylamine (Et$_3$N) (0.371 ml, 2.66 mmol) and Pd(Ph$_3$P)$_4$ (tetrakis(triphenylphosphine)palladium(0)) (77 mg, 0.067 mmol). The reaction mixture was stirred for 6 hours at 65° C., and then quenched with 1N aqueous HCl (5.0 mL) and extracted with EtOAc (3×20 ml). The organic layer was washed with brine (5.0 mL) and dried over anhydrous Na$_2$SO$_4$, filtered, and concentrated to dryness. The crude product was purified by column chromatography on silica gel (24 g, 0 to 50% EtOAc/Hexane) to afford methyl 2,3-dihydrobenzo[b][1,4]oxathiine-6-carboxylate (9-c). (400 MHz, CDCl$_3$) δ 7.48 (m, 2H), 7.02 (d, J=8.0 Hz, 1H), 4.80 (d, J=4.8 Hz, 2H), 3.87 (s, 3H), 3.16 (d, J=4.8 Hz, 2H).

Step 3: To the solution of methyl 2,3-dihydrobenzo[b][1,4]oxathiine-7-carboxylate (9-c) (220 mg, 1.046 mmol) was added DIBAL-H (2.61 mL, 2.62 mmol) at −78° C. The resulting reaction mixture was stirred at −−78° C. for 3 hours. The reaction mixture was quenched with MeOH (2 ml) and extracted with EtOAc (3×30 mL). The organic layer was dried over anhydrous Na$_2$SO$_4$, filtered, and concentrated to dryness. The crude product was purified by column chromatography on silica gel (24 g, 0 to 50% EtOAc/Hexane) to afford (2,3-dihydrobenzo[b][1,4]oxathiin-7-yl)methanol (9-d). (400 MHz, CDCl$_3$) δ 7.01 (m, 2H), 6.85 (d, J=8.0 Hz, 1H), 4.58 (bs, 2H), 4.57 (d, J=12 Hz, 2H), 3.14 (d, J=12.0 Hz, 2H).

Step 4: To the solution of (2,3-dihydrobenzo[b][1,4]oxathiin-7-yl)methanol (9-d) (130 mg, 0.713 mmol) in DCM (2 ml) was added dessmartin periodinane (DMP) (454 mg, 1.070 mmol) at 0° C. The resulting reaction mixture was stirred at 0° C. for 3 hours. The reaction mixture was quenched with 1N aq Na$_2$SO$_3$ (5 ml) and extracted with DCM (3×30 mL). The combined organic layer was dried over Na$_2$SO$_4$, filtered, concentrated under reduced pressure. The residue was purified by column chromatography on silica gel (4 g, 0 to 10% EtOAc/Hexane) to afford 2,3-dihydrobenzo[b][1,4]oxathiine-7-carbaldehyde (9-e). (400 MHz, CDCl$_3$) δ 9.87 (s, 1H), 7.37-7.29 (m, 2H), 7.18 (d, J=8.0 Hz, 1H), 4.44 (d, J=9.2 Hz, 2H), 3.18 (d, J=9.2 Hz, 2H).

Step 5: To a mixture of 2,3-dihydrobenzo[b][1,4]oxathiine-7-carbaldehyde (9-e) (95 mg, 0.527 mmol) in toluene (4 ml) was added 2-(carboxymethyl)benzoic acid (9-f) (95 ng, 0.527 mmol) and 4-(tert-butyl)-3-chloroaniline (1-a) (97 mg, 0.527 mmol). The resulting reaction mixture was stirred for 5 hours at 130° C. The reaction mixture was concentrated under reduced pressure and purified by column chromatography on silica gel (4 g, 0 to 10% MeOH/CH$_2$Cl$_2$) to afford (3R,4R or 3S,4S)-2-(4-(tert-butyl)-3-chlorophenyl)-3-(2,3-dihydrobenzo[b][1,4]oxathiin-7 yl)-1-oxo-1,2,3,4-tetrahydroisoquinoline-4 carboxylic acid. The racemate mixture was separated by SFC, IA column eluting with 15% MeOH and CO$_2$ to afford 1-78 as second eluting isomer. $^1$H NMR (400 MHz, CDCl$_3$) δ 8.19 (d, J=2.8 Hz, 1H), 7.50-7.29 (m, 4H), 7.20-7.15 (m, 2H), 688 (d, J=8.8 Hz, 1H), 6.61-6.59 (m, 2H), 5.47 (s, 1H), 4.32 (d, J=3.2 Hz, 2H), 3.97 (s, 1H), 3.04 (d, J=4.0 Hz, 2H), 1.4 (s, 9H). MS ESI calcd for C$_{28}$H$_{26}$ClNO$_4$S [M+H]$^+$ 508 found 508.

Example 10

(3R,4R) and (3S,4S)-2-(4-(tert-butyl)-3-chlorophenyl)-3-(2,3-dihydrobenzo[b][1,4]dioxin-6-yl)-N-hydroxy-1-oxo-1,2,3,4-tetrahydroisoquinoline-4-carboxamide (1-79)

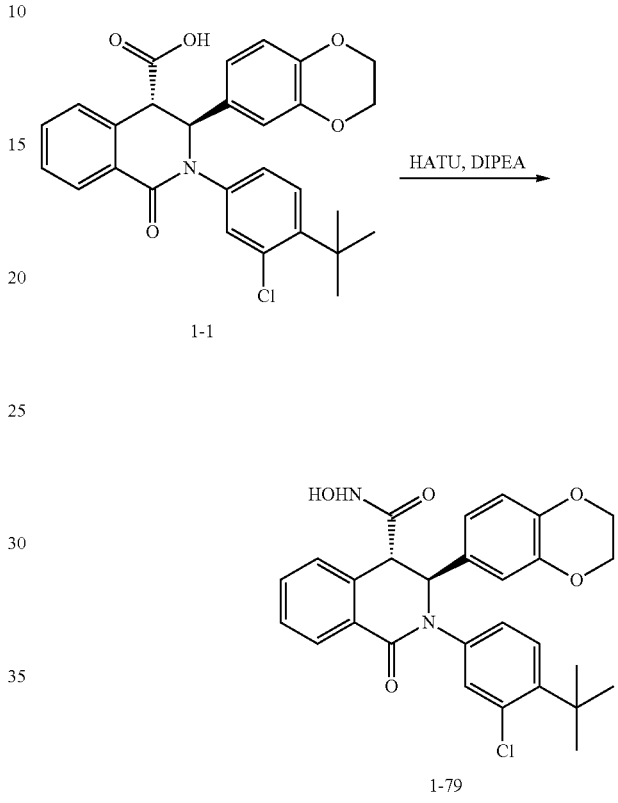

Step 1: To a solution of (3R,4R) and (3S,4S)-2-(4-(tert-butyl)-3-chlorophenyl)-3-(2,3-dihydrobenzo[b][1,4]dioxin-6-yl)-1-oxo-1,2,3,4-tetrahydroisoquinoline-4-carboxylic acid (1-1) (100 mg, 0.203 mmol) in DMF (1.0 mL) were added O-(tetrahydro-2h-pyran-2-yl)hydroxylamine (119 mg, 1.016 mmol), N,N-diisopropylethylamine (263 mg, 2.033 mmol) and HATU (100 mg, 0.264 mmol) at room temperature. The reaction mixture was continued stirring for 3 hours before 3N aqueous HCl was added and the pH was adjusted to 2. The reaction mixture was stirred for another hour. The reaction mixture was diluted with water (10 mL), extracted using EtOAc (20 ml). The layers were separated and solvent was evaporated. The crude product was purified by column chromatography on C-18 column using 0 to 100% acetonitrile/water to afford (3R,4R) and (3S,4S)-2-(4-(tert-butyl)-3-chlorophenyl)-3-(2,3-dihydrobenzo[b][1,4]dioxin-6-yl)-N-hydroxy-1-oxa-1,2,3,4-tetrahydroisoquinoline-4-carboxamide (1-79). (400 MHz, CDCl$_3$) δ 8.27 (d, J=8.5 Hz, 1H), 7.54-7.48 (m, 2H), 7.36-7.30 (m, 2H), 7.14-7.12 (m, 2H), 6.70-6.57 (m, 3H), 5.73 (s, 1H), 4.16 (s, 4H), 3.93 (s, 1H), 1.43 (s, 9H). MS ESI calcd for C$_{28}$H$_{27}$ClN$_2$O$_5$ [M+H]$^+$ 507 found 507.

Example 11

(3S,4S) and (3R,4R)-2-(4-(tert-butyl)-3-chlorophenyl)-3-(chroman-6-yl)-1-oxo-1,2,3,4-tetrahydroisoquinoline-4-carboxylic acid (1-80)

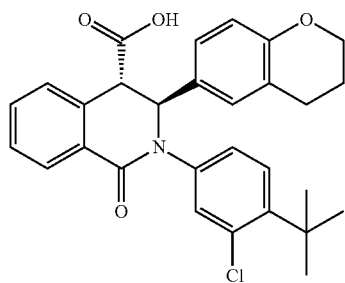

1-80

(3R,4R and 3S,4S)-2-(4-(tert-butyl)-3-chlorophenyl)-3-(chroman-6-yl)-1-oxo-1,2,3,4-tetrahydroisoquinoline-4-carboxylic acid, (1-80) were prepared by following an analogous procedure to that reported for Example 1 using commercially available chromane-6-carbaldehyde. MS ESI calcd for $C_{29}H_{29}ClNO_4$ [M+H]$^+$ 490, found 490. $^1$H NMR (400 MHz, CDCl$_3$) δ 8.23-8.18 (m, 1H), 7.49-739 (m, 2H), 7.37 (d, J=2.0 Hz, 1H), 7.35 (d, J=8.8 Hz, 1H), 7.20-7.18 (m, 1H), 7.15 (dd, J=8.4, 2.4 Hz, 1H), 6.81 (dd, J=8.4, 2.4 Hz, 1H), 6.79-6.73 (m, 1H), 6.62 (d, J=8.4 Hz, 1H), 5.49 (s, 1H), 4.10 (t, J=4.8 Hz, 2H), 3.97 (s, 1H), 2.69-2.50 (m, 2H), 198-185 (m, 2H), 1.43 (s, 9H).

Example 12

(3S,4S) and (3R,4R)-2-(4-(tert-butyl)-3-chlorophenyl)-3-(3,4-dihydro-2H-benzo[b][1,4]oxazin-6-yl)-1-oxo-1,2,3,4-tetrahydroisoquinoline-4-carboxylic acid (1-81)

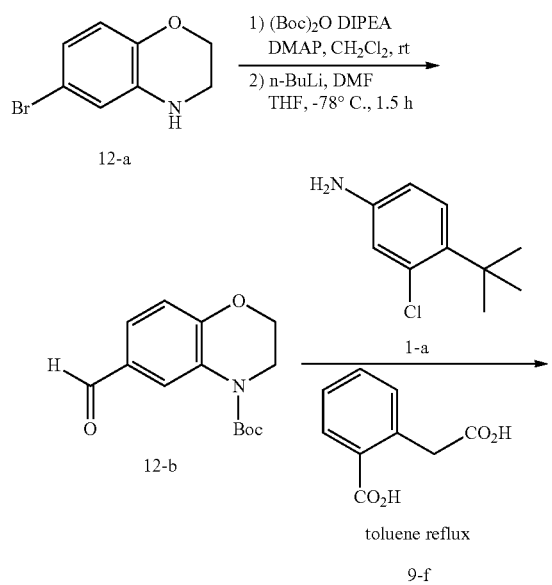

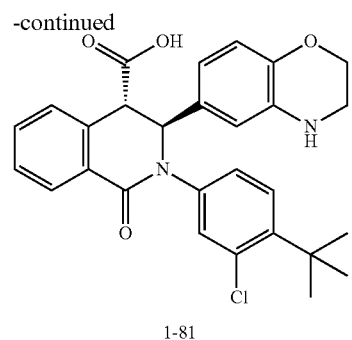

1-81

Step 1: To a solution of 6-bromo-3,4-dihydro-2H-benzo[b][1,4]oxazine (12-a) (1.00 g, 4.67 mmol) in CH$_2$CH$_2$ (30 mL) was added di-tert-butyl dicarbonate ((Boc)$_2$O) (1.63 mL, 7.01 mmol), DIPEA (1.63 ml, 9.34 mmol) and DMAP (57 mg, 0.47 mmol) at rt. The resulting mixture was stirred at rt for 2 days under a nitrogen atmosphere. To the reaction mixture was added water (20 mL) and the mixture was stirred for 5 min. The organic layer was separated and the aqueous layer was extracted with CH$_2$Cl$_2$ (×2). The combined organic extracts were dried over anhydrous sodium sulfate, filtered and concentrated under reduced pressure. The residue was purified by flash chromatography on a silica gel column using 0-100% EtOAc/hexanes to afford tert-butyl 6-bromo-2R-benzo[b][1,4]oxazine-4(3H)-carboxylate. $^1$H NMR (400 MHz, CDCl$_3$) δ 8.01 (br s, 1H), 7.06 (dd, J=8.8 Hz, J=2.2 Hz, 1H), 6.74 (d, J=8.8 Hz, 1H), 4.24-4.18 (m, 2H), 3.86-3.81 (m, 2H), 1.55 (s, 9H).

Step 2: To a solution of ter-butyl 6-bromo-2H-benzo[b][1,4]oxazine-4(3)-carboxylate (400 ng, 1.27 mmol) in THF (13 mL) was added n-butyllithium (0.83 ml, 1.7 mmol) dropwise at −78° C. After stirring at −78° C. for 30 min, DMF (0.98 ml, 12.7 mmol) was then added to the reaction mixture and stirred at −78° C. for 1 h. The mixture was quenched with water (10 mL) diluted with EtOAc (15 mL). The organic layer was separated and the aqueous layer was extracted with EtOAc (×2). The combined organic extracts were dried anhydrous sodium sulfate, filtered and concentrated under reduced pressure. The residue was purified by flash chromatography on a RediSep® 12 g silica gel column (Teledyne ISCO, Lincoln, Nebr. USA) using 0-100% EtOAC/hexanes to afford tert-butyl 6-formyl-2H-benzo[b][1,4]oxazine-4(3H)-carboxylate (12-b). $^1$H NMR (400 MHz, CDCl$_3$) δ 9.86 (s, 1H), 8.37 (br s, 1H), 7.54 (dd, J=8.4 Hz, J=2.0 Hz, 1H), 6.98 (d, J=8.4 Hz, 1H), 4.32 (t, J=4.4 Hz, 2H), 3.90 (t, J=4.4 Hz, 2H), 1.57 (s, 9H).

Step 3: To a solution of tert-butyl-2H-benzo[b][1,4]oxazine-4(3H)-carboxylate (12-b) (105 mg, 0.400 mmol) in toluene (10 mL) was added 4-(tert-butyl)-3-chloroaniline (1-a) (70 mg, 0.38 mmol) and homophthalic acid (9-) (72 mg, 0.40 mmol) at rt. The resulting mixture was heated under reflux for 4 days. The reaction mixture was concentrated under reduced pressure and the residue was purified by flash chromatography on a silica gel column using 0-30% MeOH/CH$_2$Cl$_2$ followed by reverse phase chromatography on a C18 column using (0-100% ACN/water) and then semi-prep HPLC (ACN/water with 0.05% TFA modifier) to afford (3S,4S) and (3R,4R)-2-(4-(tert-butyl)-3-chlorophenyl)-3-(3,4-dihydro-2H-benzo[b][1,4]oxazin-6-yl)-1-oxo-1,2,3,4-tetrahydroisoquinoline-4-carboxylic acid (1-81). MS ESI calcd for $C_{28}H_{28}ClN_2O_4$ [M+H]$^+$ 491, found 491. $^1$H NMR (400 MHz, CD$_3$OD) δ 8.07 (dd, J$_1$=7.6 Hz, J$_2$=1.6 Hz, 1H), 7.55-7.49 (m, 1H), 7.49-7.44 (m, 2H), 7.40 (d, J=2.41

Hz, 1H), 7.33-7.28 (m, 1H), 7.20 (dd, J=8.8 Hz, J$_{2=2.4}$ Hz, 1H), 6.58 (d, J=8.4 Hz, 1H), 6.48-6.39 (m, 2H), 5.49-5.44 (m, 1H), 4.16-4.07 (m, 3H), 3.29-3.26 (m, 2H), 1.47 (s, 9H).

Example 13

(3S,4S and 3R,4R)-2-(4-(tert-butyl)-3-chlorophenyl)-3-(4-isopropyl-3,4-dihydro-2H-benzo[b][1,4]oxazin-6-yl)-1-oxo-1,2,3,4-tetrahydroisoquinoline-4-carboxylic acid (1-82)

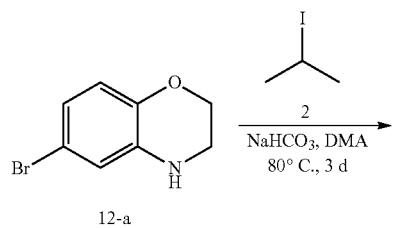

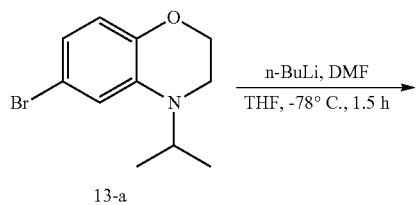

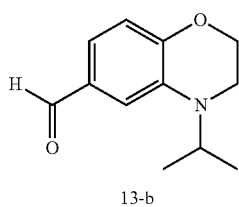

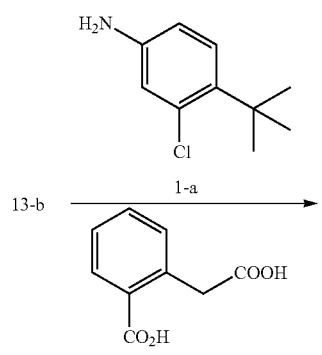

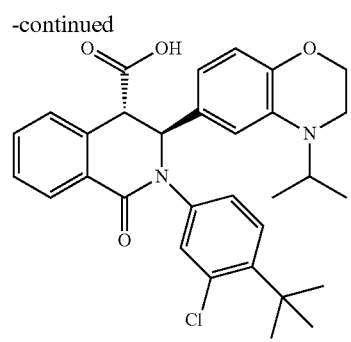

1-82

Step 1: To a solution of 6-bromo-3,4-dihydro-2R-benzo[b][1,4]oxazine (12-a) (500 mg, 2.34 mmol) in DMA (5 mL) was added sodium bicarbonate (589 mg, 7.01 mmol) and 2-iodopropane (1.17 mL, 11.7 mmol) at rt. The resulting mixture was heated at 80° C. for 3 d. The mixture was diluted with water and washed with ice water (5 mL×2). The organic layer was dried over anhydrous sodium sulfate, filtered and concentrated under reduced pressure. The residue was purified by flash chromatography on a RediSep 24 g silica gel column using 0-100% EtOAc/hexanes to afford 6-bromo-4-isopropyl-3,4-dihydro-2-benzo[b][1,4]oxazine (13-a). MS ESI calcd for $C_{11}H_{15}BrNO$ [M+H]$^+$ 256, found 256.

Step 2: To a solution of 6-bromo-4-isopropyl-3,4-dihydro-2H-benzo[b][1,4]oxazine (13-a) (340 mg, 1.33 mmol) in THF (12 mL) was added n-butyllithium (0.86 mL, 1.73 mmol) dropwise at −78° C. After stirring at −78° C. for 30 min, DMF (1.03 mL, 133 mmol) was then added dropwise to the mixture and stirred at −78° C. for 1 h. The mixture was diluted with EtOAc and quenched with sat. aq. NH$_4$Cl (ammonium chloride) solution. The organic layer was separated and the aqueous layer was extracted with EtOAc (×2). The combined organic extracts were dried over anhydrous sodium sulfate, filtered and concentrated under reduced pressure. The residue was purified by flash chromatography on a silica gel column using 0-100% EtOAc/hexanes to afford 4-isopropyl-3,4-dihydro-2-benzo[ ][1,4]oxazine-6-carbaldehyde (13-b). MS ESI calcd for $C_{12}H_{16}NO_2$ [M+H]$^+$ 206, found 206.

Step 3: To a solution of 4-isopropyl-3,4-dihydro-2H-benzo[b][1,4]oxazine-6-carbaldehyde (13-b) (150 mg, 0.73 mmol) in toluene (10 mL) was added 4-(tert-butyl)-3-chloroaniline (1-a) (128 mg, 0.70 mmol) and di-acid (9-f) (132 mg, 0.730 mmol) at rt. The resulting mixture was heated under reflux for 3 d. The solvent was concentrated under reduced pressure and the resulting residue was purified by flash chromatography on a silica gel column using 0-30% MeOH/CH$_2$Cl$_2$ followed by reverse phase chromatography on a C18 column (0-100% ACN/water) and then semi-prep HPLC (ACN/water with 0.05% TFA modifier) to afford (3S,4S) and (3R,4R)-2-(4-(tert-butyl)-3-chlorophenyl)-3-(4-isopropyl-3,4-dihydro-2H-benzo[b][1,4]oxazin-6-yl)-1-oxo-1,2,3,4-tetrahydroisoquinoline-4-carboxylic acid (1-82). MS ESI calcd for $C_{31}H_{34}ClN_2O_4$ [M+H]$^+$ 533, found 533. $^1$H NMR (400 MHz, CD30D) 8.08 (dd, J=7.6 Hz, J=1.6 Hz, H), 7.57-7.51 (m, 1H), 7.50-7.44 (m, 2H), 7.37 (d, J=2.4 Hz, 1H), 7.35-731 (m, 1H), 7.18 (dd, J=8.8 Hz, J=2.4 Hz, 1H), 6.56 (d, J=8.0 Hz, 1H), 6.47 (s, 1H), 6.38-6.30 (m, 1H), 5.48 (s, 1H), 4.15-4.06 (m, 3H), 3.82-3.69 (m, 1H), 3.22-3.05 (m, 2H), 1.47 (s, 9H), (m, 2H), 1.41 (s, 9H), 1.10 (d, J=6.8 Hz, 3H), 0.88 (d, J=6.4 Hz, 3H).

Example 14
(3S,4S and 3R,4R)-2-(4-(tert-butyl)-3-chlorophenyl)-3-(3-cyclopropyl-2,3-dihydrobenzo[b][1,4]dioxin-6-yl)-7-fluoro-1-oxo-1,2,3,4-tetrahydroisoquinoline-4-carboxylic acid (1-83)
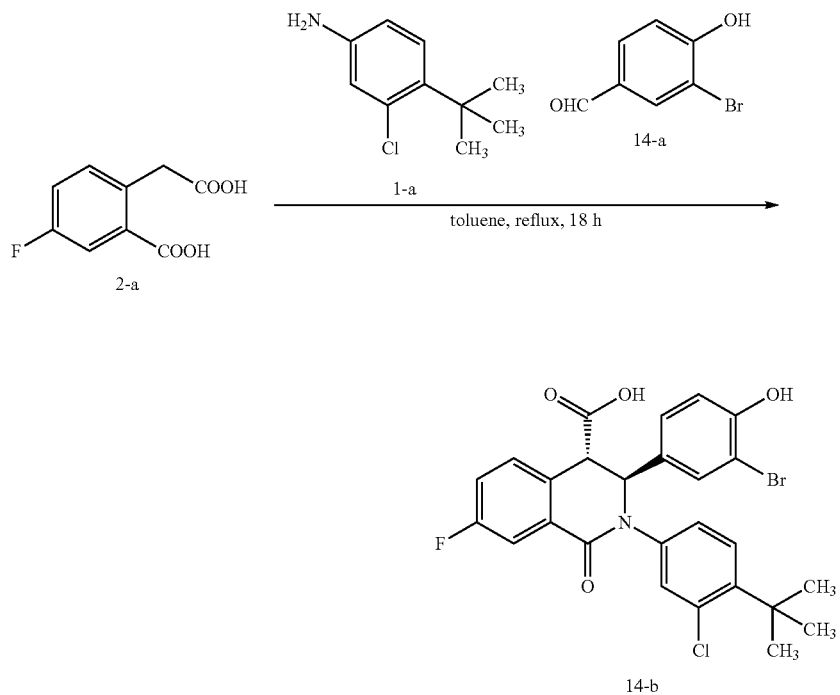
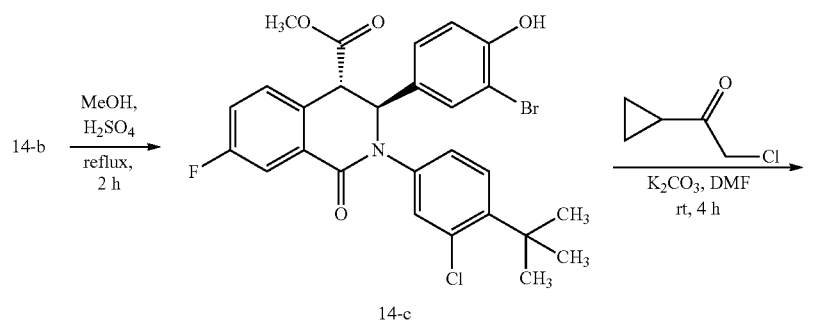
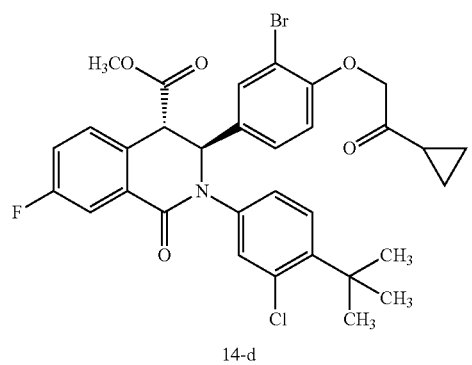

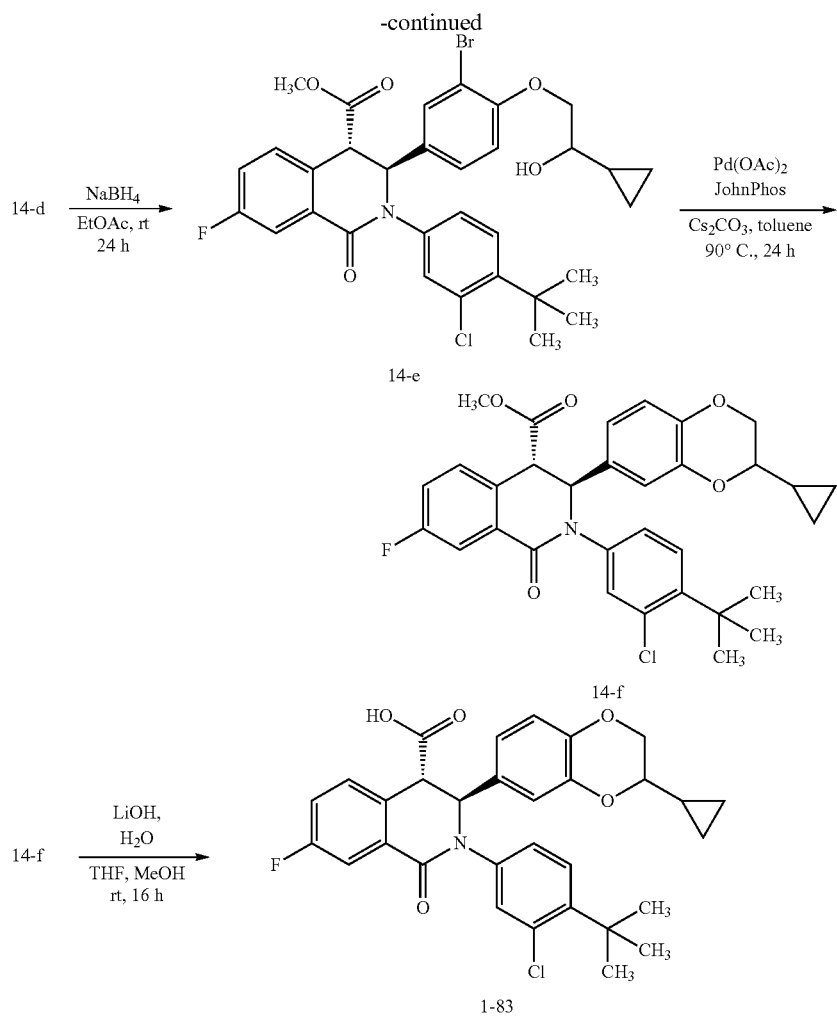

Step 1: (3S,4S and 3R,4R)-3-(3-bromo-4-hydroxyphenyl)-2-(4-(tert-buty)-3-chlorophenyl)-7-fluoro-1-oxo-1,2,3,4-tetrahydroisoquinoline-4-carboxylic acid (14-b) was synthesized following an analogous procedure to Example 2 using 3-bromo-4-hydroxybenzaldehyde MS APCI calcd for $C_{26}H_{23}BrClFNO_4$ [M+H]$^+$ 546/548, found 546/548.

Step 2: (3S,4S and 3R,4R)-3-(3-bromo-4-hydroxyphenyl)-2-(4-(tert-butyl)-3-chlorophenyl)-7-fluoro-1-oxo-1,2,3,4-tetrahydroisoquinoline-4-carboxylic acid (14-b) (1.96 g, 3.58 mmol) and $H_2SO_4$ (sulfuric acid) (0.038 ml, 0.72 mmol) in MeOH (50 mL) was heated under reflux for 3 h under a nitrogen atmosphere. The reaction mixture was cooled to rt and methanol was removed under reduced pressure. The resulting residue was diluted with water (30 mL) and sat, aq. sodium bicarbonate until pH 9. The mixture was then extracted with EtOAc (×3). The combined organic extracts were washed with brine, dried over anhydrous sodium sulfate, filtered and concentrated under reduced pressure to methyl (3S,4S) and (3R,4R)-3-(3-bromo-4-hydroxyphenyl)-2-(4-(tert-butyl)-3-chlorophenyl)-7-fluoro-1-oxo-1,2,3,4-tetrahydroisoquinoline-4-carboxylate (14-c). MS APCI calcd for $C_{27}H_{23}BrClFNO_4$ [M−H]$^-$ 558/560, found 558/560.

Step 3: To a solution of methyl (3S,4S and 3R,4R)-3-(3-bromo-4-hydroxyphenyl)-2-(4-(tert-butyl)-3-chlorophenyl)-7-fluoro-1-oxo-1,2,3,4-tetrahydroisoquinoline-4-carboxylate (14-c) (600 mg, 1.07 mmol) in DMF (10 mL) at 0° C. were added $K_2CO_3$ (potassium carbonate) (222 mg, 1.61 mmol) followed by 2-chloro-1-cyclopropylethanone (190 mg, 1.61 mmol). The resulting mixture was stirred at rt under nitrogen atmosphere for 4 hours. The reaction mixture was diluted with water (50 mL) and extracted with EtOAc (×3). The combined organic extracts were washed with brine, dried over anhydrous sodium sulfate, filtered and concentrated under reduced pressure. The resulting residue was purified by combiflash chromatography on a silica gel column (0 to 40% EtOAc/hexanes) to afford methyl (3S,4S and 3R,4R)-3-(3-bromo-4-(2-cyclopropyl-2-oxoethoxy)phenyl)-2-(4-(tert-butyl)-3-chlorophenyl)-7-fluoro-1-oxo-1,2,3,4-tetrahydroisoquinoline-4-carboxylate (14-d). MS APCI calcd for $C_{32}H_{29}BrClFNO_5$ [M−H]$^-$ 640/642, found 640/642.

Step 4: To a clear solution of methyl (3S,4S and 3R,4R)-3-(3-bromo-4-(2-cyclopropyl-2-oxoethoxy)phenyl)-2-(4-(tert-butyl)-3-chlorophenyl)-7-fluoro-1-oxo-1,2,3,4-tetrahydroisoquinoline-4-carboxylate (14-d) (250 mg, 0.389 mmol) in ethyl acetate (75 mL) at rt was added NaH$_4$ (14.7 mg, 0.389 mmol) and the resulting mixture was stirred at rt for 24 hours (open to air). Water (5 mL) was added to the reaction mixture and the two layers were separated. The organic layer was washed with brine, dried over anhydrous $Na_2SO_4$, filtered and concentrated to dryness to afford methyl (3S,4S) and (3R,4R)-3-(3-bromo-4-(2-cyclopropyl-2-hydroxyethoxy)phenyl)-2-(4-(tert-butyl)-3-chlorophenyl)-7-fluoro-1-oxo-1,2,3,4-tetrahydroisoquinoline-4-carboxylate (14-e). MS APCI calcd for $C_{32}H_{29}BrClFNO_5$ [M−H]⁻ 642/644, found 642/644.

Step 5: An over-dried reaction vial was charged with methyl (3S,4S and 3R,4R)-3-(3-bromo-4-(2-cyclopropyl-2-hydroxyethoxy)phenyl)-2-(4-(tert-butyl)-3-chlorophenyl)-7-fluoro-1-oxo-1,2,3,4-tetrahydroisoquinoline-4-carboxylate (14-e) (230 mg, 0.357 mmol), 2-(di-tert-butylphosphino)biphenyl (JohnPhos) (13 mg, 0.043 mmol), $Cs_2CO_3$ (349 mg, 1.07 mmol), and palladium (II) acetate $(Pd(OAc)_2)$ (8.0 ng, 0.036 mmol). The reaction mixture was placed under nitrogen by three vacuum/nitrogen cycles. The resulting brown mixture was heated at 90° C. for 24 hours under a nitrogen atmosphere. The reaction mixture was concentrated to dryness and the resulting residue was purified by combiflash chromatography on a silica gel column using 0 to 50% EtOAc/hexanes to afford methyl a mixture of diastereomers of (3S,4S and 3R,4R)-2-(4-(tert-butyl)-3-chlorophenyl)-3-(3-cyclopropyl-2,3-dihydrobenzo[b][1,4]dioxin-6-yl)-7-fluoro-1-oxo-1,2,3,4-tetrahydroisoquinoline-4-carboxylate (14-f). MS APCI calcd for $C_{32}H_{30}ClFNO_5$ [M−H]⁻ 562, found 562.

Step 6: To a solution of diastereomers, methyl (3S,4S and 3R,4R)-2-(4-(tert-butyl)-3-chlorophenyl)-3-(3-cyclopropyl-2,3-dihydrobenzo[b][1,4]dioxin-6-yl)-7-fluoro-1-oxo-1,2,3,4-tetrahydroisoquinoline-4-carboxylate (14-f) (65 mg, 0.12 mmol), in MeOH (1 mL) were added LiOH (lithium hydroxide) (8.28 mg, 0.346 mmol) and water (0.5 mL). The resulting colorless mixture was stirred at rt (open to air) for 16 hours. The reaction mixture was concentrated to dryness and suspended in 1 M HCl aq sol (3 mL). It was extracted with EtOAc (×2). The combined organic extracts were washed with brine, dried over anhydrous sodium sulfate, filtered and concentrated to dryness. The resulting residue was purified by reverse phase chromatography on a C18 column using 10 to 100% acetonitrile/water to afford a mixture of diastereomers (3S,4S and 3R,4R)-2-(4-(tert-butyl)-3-chlorophenyl)-3-(3-cyclopropyl-2,3-dihydrobenzo[b][1,4]dioxin-6-yl)-7-fluoro-1-oxo-1,2,3,4-tetrahydroisoquinoline-4-carboxylic acid (1-83 diastereomeric mixture). MS APCI calcd for $C_{31}H_{30}ClFNO_5$ [M+H]⁺ 550, found 550.

Step 7: The mixture of diastereomers was purified by chiral SFC (Chiralpak® AD-H column, 25% IPA/75% $CO_2$) to afford (diastereomer A, first eluting): ¹H NMR (400 MHz, $CD_3OD$) δ 7.74 (dd, J=9.0, 2.4 Hz, 1H), 7.46 (d, J=9.0 Hz, 1H), 7.42 (d, J=2.4 Hz, 1H), 7.30-7.20 (m, 3H), 6.70 (d, J=8.8 Hz, 1H), 6.63-6.58 (m, 2H), 5.60 (s, 1H), 4.26 (dd, J=11.2, 2.4 Hz, 1H), 3.96 (br s, 1H), 3.90 (dd, J=11.2, 8.0 z, 1H), 3.43-3.31 (m, 1H), 1.46 (s, 9H), 1.09-0.90 (m, 1H), 0.66-0.55 (m, 2H), 0.52-0.43 (m, 1H), 0.41-0.32 (m, 1H) (diastereomer B, second eluting): MS APCI calcd for $C_{31}H_{30}ClFNO_5$ [M+H]⁺ 550, found 550. ¹H NMR (400 MHz, $CD_3OD$) δ 7.56 (dd, J=9.0, 2.6 Hz, 1H), 7.47 (d, J=9.0 Hz, 1H), 7.40 (d, J=2.6 Hz, 1H), 7.36-7.19 (m, 3H), 6.71 (d, J=7.2 Hz, 1H), 6.63-6.58 (m, 2H), 5.57 (s, 1H), 4.28-4.25 (m, 1H), 4.07 (s, 1H), 3.93-3.87 (m, 1H), 3.47-3.31 (m, 1H), 1.33 (s, 9H), 1.01-0.89 (m, 1H), 0.65-0.53 (m, 2H), 0.52-0.44 (m, 1H), 0.42-0.37 (m, 1H).

The racemic mixture of diastereomer A (first eluting isomer) (rac-trans)-2-(4-(tert-butyl)-3-chlorophenyl)-3-(3-cyclopropyl-2,3-dihydrobenzo[b][1,4]dioxin-6-yl)-7-fluoro-1-oxo-1,2,3,4-tetrahydroisoquinoline-4-carboxylic acid was further purified by chiral SFC (Chiralpak® AD-H column, 15% EtOH/85% $CO_2CO_2$, 254 nm, 15 min) to afford (3S,4S) or (3R,4R)-2-(4-(tert-butyl)-3-chlorophenyl)-3-(3-cyclopropyl-2,3-dihydrobenzo[b][1,4]dioxin-6-yl)-7-fluoro-1-oxo-1,2,3,4-tetrahydroisoquinoline-4-carboxylic acid Enantiomer B, slower eluting enantiomer, $t_R$=6.54 min), 1-83: MS APCI calcd for $C_{31}H_{30}ClFNO_5$ [M+H]⁺ 550, found 550. ¹H NMR (400 MHz, $CD_3OD$) δ 7.74 (dd, J=9.0, 2.4 Hz, 1H), 7.46 (d, J=9.0 Hz, 1H), 7.42 (d, J=2.4 Hz, 1H), 7.30-7.20 (m, 3H), 6.70 (d, J=8.8 Hz, 1H), 6.63-6.58 (m, 2H), 5.60 (s, 1H), 4.26 (dd, J=11.2, 2.4 Hz, 1H), 3.96 (br s, 1H), 3.90 (dd, J=11.2, 8.0 Hz, 1H), 3.43-3.31 (m, 1H), 1.46 (s, 9H), 1.09-0.90 (m, 1H), 0.66-0.55 (m, 2H), 0.52-0.43 (m, 1H), 0.41-0.32 (m, 1H).

Example 15

(3S,4S or 3R,4R)-2-(4-(tert-butyl)-3-chlorophenyl)-3-(2,3-dihydrobenzo[b][1,4]oxathiin-6-yl)-7-fluoro-1-oxo-1,2,3,4-tetrahydroisoquinoline-4-carboxylic acid (1-84)

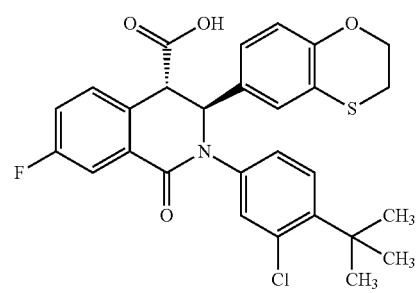

1-84

Racemate compound (1-84) was prepared by following an analogous procedure to that reported in Example 2 using 2,3-dihydrobenzo[b][1,4]oxathiine-6-carbaldehyde. The racemic mixture of compound was purified by chiral SFC (IA column, 25%/75% methanol/$CO_2$, 254 nm, 10 min) to afford (trans)-2-(4-(tert-butyl)-3-chlorophenyl)-3-(2,3-dihydrobenzo[b][1,4]oxathiin-6-yl)-7-fluoro-1-oxo-1,2,3,4-tetrahydroisoquinoline-4-carboxylic acid (Enantiomer A, first eluting, $t_R$=4.72 min) 1-84. MS APCI calcd for $C_{28}H_{26}ClFNO_4$ [M+H]⁺ 526, found 526. ¹H NMR (300 MHz, $CDCl_3$) δ 7.88 (dd, J=8.7, 2.7 Hz, 1H), 7.41-7.35 (m, 2H), 7.24-7.10 (m, 3H), 6.82-6.78 (m, 1H), 6.71-6.67 (m, 2H), 5.49 (s, 1H), 4.39 (dd, J=4.5, 3.0 Hz, 2H), 3.96 (s, 1H), 3.08-3.05 (dd, J=4.5, 3.0 Hz, 2H), 1.44 (s, 9H).

Example 16

2-((3S,4S or 3R,4R)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinolin-4-yl)acetic acid (1-85)

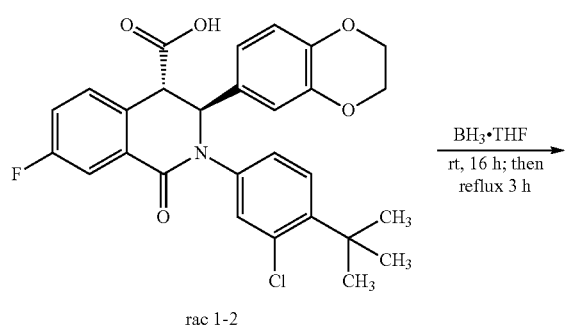

rac 1-2

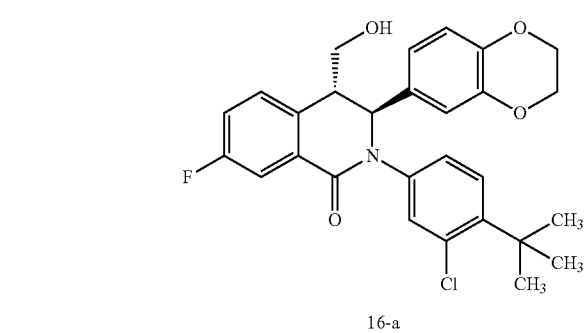

16-a

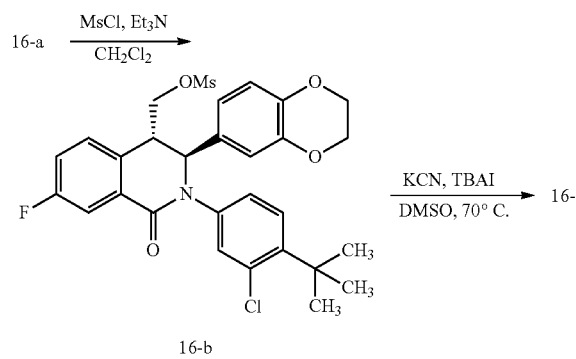

16-b

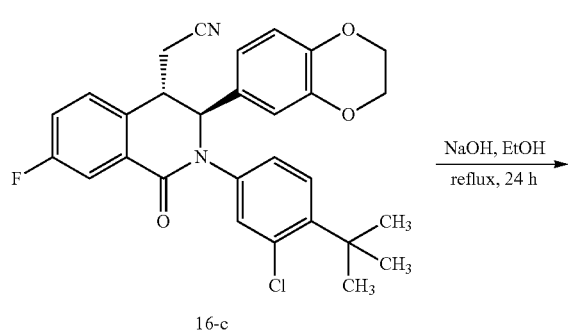

16-c

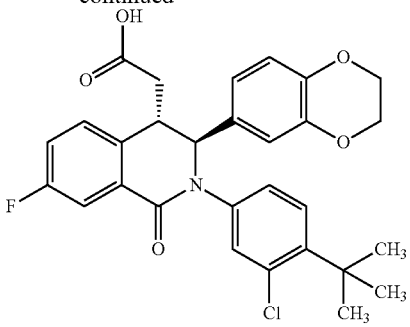

1-85

Step 1: To a solution of racemic (3S,4S) and (3R,4R)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinoline-4-carboxylic acid (1-2) (480 mg, 0.941 mmol) in anhydrous THF (5 mL) was added BH$_3$.THF (1 M in THF, 4.71 mL, 4.71 mmol) dropwise at rt. The resulting mixture was heated under reflux for 2 h under nitrogen atmosphere. The reaction mixture was cooled to rt and quenched with MeOH (0.5 mL). The reaction mixture was diluted with water (20 mL) and extracted with EtOAc (×3). The combined organic extracts were washed with brine, dried over anhydrous sodium sulfate, filtered, and concentrated under reduced pressure. The resulting residue was purified by reverse phase chromatography on a C18 column (10 to 100 CH$_3$CN/H$_2$O) to afford ((3S,4S) and (3R,4R)-2-(4-(tert-butyl)-3-chlorophenyl)-3-(2,3-dihydrobenzo[b][1,4]dioxin-6-yl)-7-fluoro-4-(hydroxymethyl)-3,4-dihydroisoquinolin-1(2H)-one (16-a). MS APCI calcd for C$_{28}$H$_{28}$ClFNO$_4$ [M+H]$^+$ 496, found 496.

Step 3: To a solution of ((3S,4S and 3R,4R)-2-(4-(tert-butyl)-3-chlorophenyl)-3-(2,3-dihydrobenzo[b][1,4]dioxin-6-yl)-7-fluoro-4-(hydroxymethyl)-3,4-dihydroisoquinolin-1(2H)-one (16-a) (210 mg, 0.424 mmol) in dichloromethane (10 mL) at 0° C. were added trimethylamine (Et$_3$N) (0.12 mL, 0.85 mmol) and methanesulfonyl chloride (MsCl) (0.050 mL, 0.64 mmol). The resulting mixture was stirred at rt for 3 h under nitrogen atmosphere. The reaction mixture was diluted with water (10 mL) and the two layers were separated. The organic layer was washed with brine, dried over anhydrous sodium sulfate, filtered, and concentrated under reduced pressure to afford ((3S,4S and 3R,4R)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinolin-4-yl)methyl methanesulfonate (16-b). MS APCI calcd for C$_{29}$H$_{30}$ClFNO$_6$S [M+H]$^+$ 574, found 574.

Step 4: To a solution ((3S,4S and 3R,4R)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinolin-4-yl)methyl methanesulfonate (16-b) (260 mg, 0.464 mmol) in DMSO (3 mL) was added potassium cyanide (KCN) (181 mg, 2.79 mmol) and tetrabutylammonium iodide (TBAI) (343 mg, 0.929 mmol). The resulting mixture was heated at 75° C. for 4 h. The reaction was cooled to rt and diluted with water (50 mL). The mixture was extracted with EtOAc (×3). The combined organic extracts were washed with water (×4), brine, dried over anhydrous sodium sulfate, filtered and concentrated under reduced pressure. The resulting residue was purified by combiflash chromatography on a silica gel column (0 to 60% f EtOAc/hexanes) to afford 2-((3S,4S and 3R,4R)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinolin-4-yl)acetonitrile (16-c). MS APCI calcd for $C_{29}H_{27}ClFN_2O_3$ [M+H]$^+$ 505, found 505.

Step 5: To a solution of 2-((3S,4S and 3R,4R)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinolin-4-yl)acetonitrile (16-c) (135 mg, 0.267 mmol) in MeOH (10 mL) was added NaOH (5 M in water, 0.5 mL, 2.5 mmol). The resulting mixture was heated under reflux for 48 h. The reaction mixture was cooled to rt and diluted with water (50 mL). The mixture was acidified with aq. 2 N HCl to pH=3 and extracted with EtOAc (×3). The combined organic extracts were washed with brine, dried over anhydrous sodium sulfate, filtered and concentrated under reduced pressure. The resulting residue was purified by reverse phase chromatography (10 to 100% acetonitrile/water) to afford 2-((3S,4S) and (3R,4R)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinolin-4-yl)acetic acid (1-85 racemic mixture). MS APCI calcd for $C_{29}H_{28}ClFNO_5$ [M+H]$^+$ 524, found 524. $^1$H NMR (400 MHz, CD$_3$OD) δ 7.76 (dd, J=8.6 Hz, 2.4 Hz, 1H), 7.48 (d, J=8.6 Hz, 1H), 7.33 (d, J=2.4 Hz, 1H), 7.22-7.25 (m, 2H), 7.16 (dd, J=8.6 Hz, 2.4 Hz, 1H), 6.70-6.82 (m, 1H), 6.59-6.61 (m, 2H), 5.12 (s, 1H), 4.16 (s, 4H), 3.61-3.65 (m, 1H), 2.99 (dd, J=16.4, 9.2 Hz, 1H), 2.73 (dd, J=16.4, 6.0 Hz, 1H), 1.47 (s, 9H).

The racemic mixture was resolved by CHIRAL-SFC (Column CCOF4, (250 mm*21 mm), with 30% MeOH (+0.25% DMEA) in CO$_2$) affording two peaks with retention times of 3.9 min and 5.8 minutes. Peak 1 afforded 2-((3S,4S or 3R,4R)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinolin-4-yl)acetic acid (1-85).

Peak 1 (1-85): LCMS ($C_{29}H_{28}ClFNO_5$) (ES, m/z) 524 [M+H]$^+$. $^1$H NMR (499 MHz, DMSO-d$_6$) δ 7.69 (d, J=7.7 Hz, 1H), 7.46 (d, J=8.6 Hz, 1H), 7.39 (s, 1H), 7.35-7.27 (m, 2H), 7.16 (d, J=8.1 Hz, 1H) 675 (d, J=8.2 Hz, 1H), 6.61-6.55 (M, 2H), 4.16 (s, 4H), 3.58-3.54 (m, 1H), 2.97 (dd, J=15.9, 8.1 Hz, 1H), 2.59 (dd, J=16.0, 6.1 Hz, 1H), 2.47-2.40 (m, 1H), 1.41 (s, 9H).

Example 17

(3R,4R and 3S,4S)-3-(2,3-dihydrobenzo[b][1,4]dioxin-6-yl)-2-((S and R)-6-(hydroxymethyl)-5,6,7,8-tetrahydronaphthalen-2-yl)-1-oxo-1,2,3,4-tetrahydroisoquinoline-4-carboxylic acid (1-86)

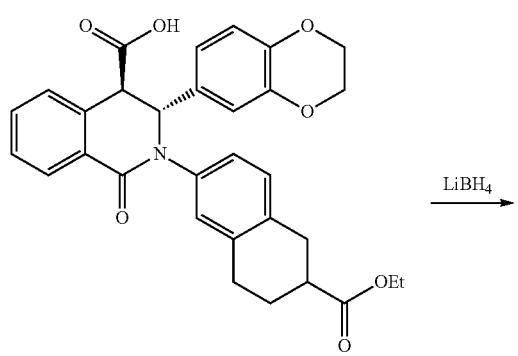

17-1

LiBH$_4$ →

-continued

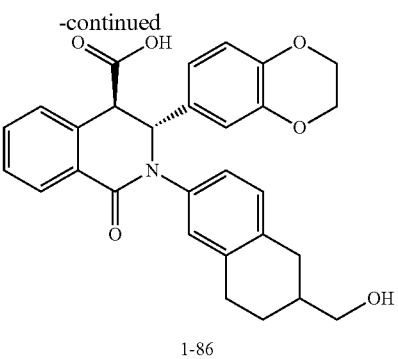

1-86

Step 1: (3R,4R and 3S,4S)-3-(2,3-dihydrobenzo[b][1,4]dioxin-6-yl)-2-((S and R)-6-(ethoxycarbonyl)-5,6,7,8-tetrahydronaphthalen-2-yl)-1-oxo-1,2,3,4-tetrahydroisoquinoline-4-carboxylic acid (17-1) was synthesized following an analogous procedure to that reported as in Example 1-1 using ethyl 6-amino-1,2,3,4-tetrahydronaphthalene-2-carboxylate. MS ESI calcd for $C_{31}H_{29}NO_7$ [M+H]$^+$ 528, found 528.

Step 2: To a solution of (3R,4R and 3S,4S)-3-(2,3-dihydrobenzo[b][1,4]dioxin-6-yl)-2-((S and R)-6-(ethoxycarbonyl)-5,6,7,8-tetrahydronaphthalen-2-yl)-1-oxo-1,2,3,4-tetrahydroisoquinoline-4-carboxylic acid (17-1) (12 mg, 0.023 mmol) in THF (1 mL) was added LiBH$_4$ (2.0 mg, 0.091 mmol). The reaction mixture was brought to 60° C. for 1 hour. The reaction mixture was cooled to room temperature then diluted with MeOH (1 mL). After stirring for 10 minutes reaction mixture was concentrated tinder reduced pressure and directly purified by silica gel chromatography (0-100%, 3:1 (EtOAc:EtOH)/hexanes) to afford (3R,4R and 3S,4S)-3-(2,3-dihydrobenzo[b][1,4]dioxin-6-yl)-2-((S and R)-6-(hydroxymethyl)-5,6,7,8-tetrahydronaphthalen-2-yl)-1-oxo-1,2,3,4-tetrahydroisoquinoline-4-carboxylic acid (1-86). MS ESI calcd for $C_{29}H_{27}NO_6$ [M+H]$^+$ 486, found 486. $^1$H NMR (600 MHz, DMSO-d$_6$) δ 7.91 (d, J=7.5 Hz, 1H), 7.47-7.41 (m, 1H), 7.40-7.34 (m, 1H), 7.28-720 (1H), 7.05-6.94 (m, 3H), 6.66 (d, J=8.4 Hz, 1H), 6.61-6.53 (m, 2H), 5.51 (s, 1m), 4.56-4.46 (m, 1H), 4.10 (s, 4H), 3.37-3.31 (m, 3H), 2.77-2.61 (m, 3H), 2.37-2.26 (m, 1H), 1.90-1.81 (m, 1H), 1.79-1.69 (m, 1H).

Biological Data
Biological Evaluation

The individual compounds described in the Examples above are defined as STING inhibitors by demonstrating binding to the STING protein with an IC$_{50}$ of less than 20 μM in the STING Biochemical [$^3$H]cGAMP Competition Assay (using either HAQ or wild type (WT) STING) and demonstrating inhibition of interferon production less than 30 μM in the cGAMP stimulated INF-β (interferon-β) THP1 cell assay. The methods below describe each of these assays.

[$^3$H]-cGAMP (Cyclic Guanosine Monophosphate (GMP)-Adenosine Monophosphate (AMP) Synthesis 2.3 mL of buffer solution containing 80 mM tris Cl, 200 mM MgCl$_2$ and 20 mM NaCl followed by 0.32 mL of a 10 mM aqueous solution of guanosine triphosphate (GTP) was added to a plastic 50 mL Amicon® centrifuge tube. A solution of [3H]ATP (adenosine triphosphate) (21 Ci/mmol, 45 mCi) in 0.5 mL H$_2$O was then added followed by 1 mL of a 1 mg/mL solution of DNA and 53 uL of a 47 mM solution of enzyme. Additional 20 was added to bring the total volume to 10 mL.

The reaction was stirred for 2 h at 37° C. and then added directly to an Amicon® Ultra-15 10K centrifuge tube (Millipore Sigma, Burlington, Mass., USA) and spun for 1 h at 4,000 g. The collected solution was then purified on a semi-prep Mono Q® column (Supelco, Bellefonte, Pa., USA) using the following mobile phases:

A: 0.05M TrisCl pH 8.5 adjusted with IM NaOH
B: 0.05M TrisCl, 0.5M NaCl pH 8.5 adjusted with IM NaOH Gradient: 100% A for 5 min followed by a linear gradient to 50:50 (A:B) over 25 min, 3 ml/min, 254 nm.

The collected product fractions were pooled and adjusted to a total volume of 30 mL with buffer A. A total yield of 15.5 mCi of [3H]cGAMP was isolated at a radiochemical purity of 98.0% at a specific activity of 21.5 Ci/mmol.

cGAS (Cyclic GMP-AMP Synthase) Enzyme

A recombinant DNA vector was chemically synthesized to express the truncated human cGAS enzyme (residues 161-522). To aid in expression and purification, the amino terminus contains a hexahistidine tag, SUMO (small ubiquitin-like modifier) tag and TEV (tobacco etch virus) cleavage site. The recombinant enzyme was overexpressed in Rosetta™ 2(DE3) Singles™ Competent Cells (Novagen). Affinity purification was carried out using HIS-Select HF Nickel Affinity Gel (Sigma-Aldrich®, St. Louis, Mo., USA) followed by size exclusion chromatography using a Hi-Load® 26/60 Superdex® 200 prep grade column (GE Healthcare, Chicago, Ill., USA). Fractions were pooled, concentrated, flash frozen in liquid nitrogen and stored at −80° C. until needed for research applications.

$^3$H-cGAMP Filtration Binding Assay (HAQ STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* (*T. ni*; Expression Systems, cat #94-002F, Expression Systems, Davis, Calif., USA) cell membranes overexpressing full-length HAQ STING prepared in-house and tritiated cGAMP ligand also purified in-house.

The basic HAQ STING filtration assay protocol is as follows:

The compounds were serially titrated by the Hamilton STARplus CORE™ in a 96-well plate (Greiner Bio One, Monroe, N.C., USA, catalog #651201) using a 1:3 ten-point dose response format. After compound preparation, a 2.2 g/ml working concentration of STING membrane (SEQ. ID. No. 1) was prepared by diluting concentrated membrane into assay buffer (1×PBS (Phosphate-Buffered Saline); Invitrogen™, Thermo Fisher Scientific, Waltham, Mass., USA, catalog #SH30028.02) and douncing 7× using a manual tissue homogenizer (Wheaton®, Millville, N.J., USA, catalog #357546), 148 μL of prepared membrane was then manually added to each well of a 96-well deep-well PP plate (Thermo Fisher Scientific, catalog #12-566-121). Following membrane addition, 2 μL of either titrated test compound, DMSO (dimethyl sulfoxide) control (Sigma-Aldrich®, catalog #276855), or cold cGAMP control (prepared in-house) was added to the appropriate wells using a Biomek® FX (Beckman Coulter Life Sciences, Indianapolis, Ind., USA). Compound and membrane then preincubated for 60 min at RT to allow compound binding to equilibrate. Following equilibration, 8 nM of [$^3$H] c-GAM/P ligand was prepared by diluting into assay buffer, and 50 μL of this working stock was then manually added to each well of the assay plate. Plates were then incubated at RT for 60 min, and the contents of each assay plate were then filtered through a 96-well GF/B filter plate (PerkinElmer, Akron, Ohio, USA, catalog #6005250) using a TomTec MachIII Cell Harvester equipped with 20 mM HEPES buffer (Fisher Scientific, catalog #BP299500). The filter plates were then dried at 55° C. for 30 min using a pressurized VWR oven (VWR, Radnor, Pa., USA) before 302 μL of Ultima Gold™ F scintillate (PerkinElmer) was added to each well. Tritium levels for each reaction well were then measured using a TopCount™ plate reader (PerkinEmer).

After normalization to controls, the percent activity for each compound concentration was calculated by measuring the amount of remaining radioactivity. The plot of percent activity versus the log of compound concentration was fit with a 4-parameter dose response equation to calculate $EC_{50}$ values.

The final reaction conditions were:

| Component | Volume (uL) | Final Concentration |
| --- | --- | --- |
| STING membrane | 148 | 1.5 ug/ml |
| $^3$H-cGAMP | 50 | 2.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001 μM with 1.0% residual DMSO.

Full-Length STING (HAQ) Virus Generation

STING virus was generated using an insect cell baculovirus system. *Spodoptera frugiperda* Sf21 cells (Kempbio, Inc., Gaithersburg, Md., USA) were diluted to 5e5 cells/ml in Sf-900™ II SFM media (LifeTechnologies (Thermo Fisher Scientific), Waltham, Mass., USA, catalog #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of HAQ STING [STING (1-379)R71H,G230A,H232R,R293Q-GG-AviTag-GS-HRV3C-HIS8/pBAC1]DNA (custom synthesis, Genewiz, Inc., South Plainfield, N.J., USA) with mL Sf-900™ II SFM media containing 10 μL Cellfectin® II Reagent (Invitrogen (Thermo Fisher Scientific), catalog #10362100) and 100 ng viral backbone BestBac™ 2.0, v-cath/chiA Deleted Linearized Baculovins DNA (Expression Systems, catalog #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, mL Sf-900™ II SFM media (no antibiotics) was added to each well of the 6-well plate. After media addition, the cells were allowed to incubate with DNA at 27° C. for 5-7 days to generate the P0 viral stock. To generate P1 viral stocks, 0.5 mL of P0 viral supernatant was added to 50 mL uninfected Sf21 cells (seeded the day prior to infection at a density of 5×10$^5$ cells/mL to allow for one overnight doubling) in Sf-900™ II SFM media containing 5 μg/mL gentamicin (Invitrogen (Thermo Fisher Scientific), catalog #15710072). The infected cells were then incubated at 27° C. for 3d while shaking at 110 rpm (ATR Biotech Multitron Infors HT incubator Shaker, catalog #AJ=118, ATR, Inc, Laurel, Md., USA). On day 3, P1 cultures were counted using a Vi-Cell XR (Beckman Coulter Life Sciences, catalog #383556) to confirm infection had occurred (cell size ≥3 μm larger than uninfected cells and viability approximately 85-95%). Cultures were harvested in 50 mL conical tubes and centrifuged at 2000×g for 10 min at 4° C. The P1 viral supernatants were poured off into clean 50 mL centrifuge tubes, and the remaining P1 cell pellets were used to generate Baculovirus Infected Insect Cells (BIICs) according to in-house validated SOP (standard operating procedure). Cryopreservation media containing Sf-900™ II SFM media with 10% heat inactivated fetal bovince serum FBS, 10% DMSO (Sigma #D2650), and 5 μg/ml gentamicin was prepared in-house and sterilized through 0.22 μM filter immediately prior to use. P1 cell pellets were resuspended to a density of 2e7 cells/ml and aliquoted into cryovials (1 mL per vial). Cryovials were placed in Mr. Frosty cell freezers O/N (Nalge Nunc International (Thermo Fisher Scientific)) at −80° C. and transferred to liquid nitrogen for long term storage the following day. To generate P2 viral stock, 0.5 mL of the P1 viral supernatant was added to 50 mL uninfected Sf21 cells (seeded the day prior to infection at a density of 5×10$^5$ cells/mL to allow for one overnight doubling) in Sf-900™ II SFM media containing 5 μg/mL gentamicin. These cells were incubated at 27° C. for 3d while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mL×100 pfu/cell; pfu=plague forming units).

Full-Length STING (HAQ) Expression

To generate STING membranes, P1/P2 BIICs were amplified overnight by adding thawed BIICs to Sf21 cells seeded at a density of 1.0×10$^6$ cells/mL The volume of BIIC used to infect the culture was calculated using an assumed BIIC titer of 2e9 pfu/ml to achieve an MOI (multiplicity of infection) of 10 in the overnight amplification. After culturing overnight, the cells were counted on a Vi-Cell XR to confirm infection had occurred (cell size ≥3 μm larger than uninfected cells and viability approximately 80-90%). The volume of infected Sf21 cells from the overnight amplification used to infect the large-scale expression of *Trichoplusia ni* (*T. ni*; Expression Systems, cat #94-002F, www.expression-systems.com) seeded at a density of 0.0×10$^6$ in cell media (ESF921 SFM containing 5 μg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. *T. ni* cells were counted on a Vi-Cell XR to confirm infection had occurred (cell size ≥3 μm larger than uninfected cells and viability approximately 80-90%) prior to harvest.

Full-Length STING (HAQ) Membrane Generation

Buffer stock reagents:
1) 1 M HEPES (hydroxyethyl piperazineethanesulfonic acid) pH 7.5 (Teknova, Hollister, Calif., USA, Catalog #H1035)
2) 5 M NaCl, (Sigma-Aldrich®, St. Louis, Mo., USA, Cat #S5150-IL)
3) KCl, (Sigma-Aldrich®, St. Louis, Mo., USA, Cat #319309-500 ML)
4) Complete EDTA-free protease inhibitor tablets (Roche Diagnostics, Indianapolis, Ind., USA, Cat #11873580001)
5) Benzonase, Pierce™ Universal Nuclease for Cell Lysis, Thermo Scientific (Thermo Fisher Scientific), Cat. #88702)

Lysis buffer [25 mM HEPES pH 7.5, 10 mM MgCl$_2$, 20 mM KCl, (Benzonase 1:5000, Complete Protease Inhibitor tab/50 mL)] was added to the pellet of cells expressing full-length STING (HAQ) prepared above at 5 mL Lysis buffer/g of cell pellet. The pellet was resuspended and dounced twenty times using a Wheaton Dounce Homogenizer (Wheaton®, Millville, N.J., USA) to disrupt the cell membrane. Homogenized lysate was then passed through the EmulsiFlex-C5 microfluidizer (Avestin, Inc., Ottowa, Calif.) at a pressure close to 5000 PSI. The resuspended pellet was centrifuged at 36,000 rpm (00,000×g) in a 45 Ti rotor in the ultra-high speed centrifuge for 45 min, 4° C. The supernatant was removed. The pellet then was resuspended in wash buffer [(25 mM HEPES pH7.5, 1 mM MgCl$_2$, 20 mM KCl, IM NaCl (Complete Protease Inhibitor tab/50 mL)] at a volume of 50 mL pellet/centrifuge tube. The pellet/wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1 tablet/50 mL). The protein concentration was measured by Bradford assay (Bio-Rad Protein Assay, Cat #500-0006, Bio-Rad, Hercules, Calif., USA), and protein enrichment was determined by SDS-PAGE (sodium dodecyl sulfate polyacrylamide gel electrophoresis) and confirmed by Western blot. The resuspended membranes were stored at −80° C.

```
Full-Length HAG STING [STING(1-379)R71H, G230A,
H232R, R293Q-GG-AviTag-GS-HRV3C-HIS]Amino AGd
Sequence:
                                              (SEQ. ID. No. 1)
MPHSSLHPSIPCPRGHGAQKAALVLLSACLVTLNATGLGEPPEHTLRYLVLHLASLQLGLL

LNGVCSLAEELHHIFISRYRGSYWRTVRACLGGPLRRGALLLLSIYFYYSLPNAVGPPETW

MLALLGLSQALNILLGLKGLAPAEISAVCEKGNFNVAHGLAWSYYIGYLRLILPELQARIR

TYNQHYNNLLRGAVSQRLYlLLPLDCGVPDNLSMADPNIRFLDKLPQQTADRAGIKDRVYS

NSIYELLENGQRAGTCVLEYATPLQTLFAMSQYSQAGFSREDRLEQAKLITQTLEDILADA

PESQNNCRLIAYQEPADDSSFSLSQEVLRHLRQEEKEEVTVGSLKTSAVPSTSTMSQEPEL

LISGMEKPLPLRTDFSGGGLNDIFEAQKIEWHEGSLEVLFQGPHHHHHHHH
```

-continued

Full-length HAQ [STING(1-379)R71H, G230A, H232R,
R293Q-GG-AviTag-GS-HRV3C-HIS8/pBAC1] PlasMid
DNA Sequence:
(SEQ. ID. No. 2)
GGAACGGCTCCGCCCACTATTAATGAAATTAAAAATTCCAATTTTAAAAAACGCAGCAAGA

GAAACATTTGTATGAAAGAATGCGTAGAAGGAAAGAAAAATGTCGTCGACATGCTGAACAA

CAAGATTAATATGCCTCCGTGTATAAAAAAAATATTGAACGATTTGAAAGAAAACAATGTA

CCGCGCGGCGGTATGTACAGGAAGAGGTTTATACTAAACTGTTACATTGCAAACGTGGTTT

CGTGTGCCAAGTGTGAAAACCGATGTTTAATCAAGGCTCTGACGCATTTCAACAACCACGA

CTCCAAGTGTGTGGGTTGAAGTCATGCATCTTTTAATCAAATCCCAAGATGTGTATAAACC

ACCAAACTGCCAAAAAATGAAAACTGTCGACAAGCTCTGTCCGTTTGCTGGCAACTGCAAG

GGTCTCAATCCTATTTGTAATTATTGAATAATAAAACAATTATAAATGCTAAATTTGTTTT

TTATTAACGATACAAACCAAACGCAACAAGAACATTTGTAGTATTATCTATAATTGAAAAC

GCGTAGTTATAATCGCTGAGGTAATATTTAAAATCATTTTCAAATGATTCACAGTTAATTT

GCGACAATATAATTTTATTTTCACATAAACTAGACGCCTTGTCGTCTTCTTCTTCGTATTC

CTTCTCTTTTTCATTTTTCTCTTCATAAAAATTAACATAGTTATTATCGTATCCATATATG

TATCTATCGTATAGAGTAAATTTTTTGTTGTCATAAATATATATGTCTTTTTTAATGGGGT

GTATAGTACCGCTGCGCATAGTTTTTCTGTAATTTACAACAGTGCTATTTTCTGGTAGTTC

TTCGGAGTGTGTTGCTTTAATTATTAAATTTATATAATCAATGAATTTGGGATCGTCGGTT

TTGTACAATATGTTGCCGGCATAGTACGCAGCTTCTTCTAGTTCAATTACACCATTTTTA

GCAGCACCGGATTAACATAACTTTCCAAAATGTTGTACGAACCGTTAAACAAAAACAGTTC

ACCTCCCTTTTCTATACTATTGTCTGCGAGCAGTTGTTTGTTGTTAAAAATAACAGCCATT

GTAATGAGACGCACAAACTAATATcACAAACTGGAAATGCTATCAATATATAGTTGCTGA

TCAGATCTGATCATGGAGATAATTAAAATGATAACCATCTCGCAAATAAATAAGTATTTA

CTGTTTTCGTAACAGTTTTGTAATAAAAAAACCTATAAATATAGGATCCATGCCCCACTCC

AGCCTGCATCCATCATCCCGTGTCCCAGGGGTCACGGGGCCCAGAAGGCAGCCTTGGTTCT

GCTGAGTGCCTGCCTGGTGACCCTTTGGGGGCTAGGAGAGCCACCAGAGCACACTCTCCGG

TACCTGGTGCTCCACCTAGCCTCCCTGCAGCTGGGACTGCTTGTTAAACGGGGTCTGCAGC

CTGGCTGAGGAGCTGCACCACATCCACTCCAGGTACCGGGGCAGCTAGGGAGGAGGTGCGG

GCCTGCCTGGGCTGCCCCCTCCGCCGTGGGGCCCTGTTGCTGCTGTCCATCTATTTCTACT

ACTCCCTCCCAAATGCGGTCGGCCCGCCCTTCACTTGGATGCTTGCCCTCCTGGGCCTCTC

GCAGGCACTGAACATCCTCCTGGGCCTCAAGGGCCTGGCCCCAGCTGAGATCTCTGCAGTG

TGTGAAAAAGGGAATTFCAACGTGGCCCATGGGCTGGCATGGTCATATTACATCGGATATC

TGCGGCTGATCCTGCCAGAGCTCCAGGCCCGGATTCGAACTTACAATCAGCATTACAACAA

CCTGCTACGGGGTGCAGTGAGCCAGCGGCTGTATATTCTCCTCCCATTGGACTGTGGGGTG

CCTGATAACCTGAGTATGGCTGACCCCAACATTCGCTTCCTGGATAAACTGCCCCAGCAGA

CCGCTGACCGTGCTGGCATCAAGGATCGGGTTTACAGCAACAGCATCTATGAGCTTCTGGA

GAACGGGCAGCGGGCGGGCACCTGTGTCCTGGAGTACGCCACCCCCTTGCAGACTTTGTTT

GCCATGTCACAATACAGTCAAGCTGGCTTTAGCCGGGAGGATAGGCTTGAGCAGGCCAAAC

TCTTCTGCCAGACACTTGAGGACATCCTGGCAGATGCCCCTGAGTCTCAGAACAACTGCCG

CCTCATTGCCTACCAGGAACCTGCAGATTGACAGCAGCTTCTCGCTGTCCCAGGAGGTTCT

CCGGCACCTGCGGCAGGAGGAAAAGGAAGAGGTTACTGTGGGCAGCTTGAAGACCTCAGCG

```
GTGCCCAGTACCTCCACGATGTCCCAAGAGCCTGAGCTCCTCATCAGTGGAATGGAAAAGC
CCCTCCGTCTCCGCACGGATTTCTCTGGCGGTGGCCTGAACGACATCTTCGAAGCCCAGAA
AATCGAATGGCATGAAGGCAGCCTGGAAGTGCTGTTCCAGGGCCCACACCACCATCATCAC
CATCACCATTAATGAGCGGCCGCACTCGAGCACCACCACCACCACCACTAACCTAGGTAGC
TGAGCGCATGCAAGCTGATCCGGGTTATTAGTACATTTATTAAGCGCTAGATTCTGTGCGT
TGTTGATTTACAGACAATTGTTGTACGTATTTTAATAATTCATTAAATTTATAATCTTTAG
GGTGGTATGTTAGAGCGAAATCAAATGATTTTCAGCGTCTTTATATCTGAATTTAAATAT
TAAATCCTCAATAGATTTGTAAAATAGGTTTCGATTAGTTTCAAACAAGGGTTGTTTTTCC
GAACCGATGGCTGGACTATCTAATGGATTTTCGCTCAACGCCACAAAACTTGCCAAATCTT
GTAGCAGCAATCTAGCTTTGTCGATATTCGTTTGTGTTTTGTTTTGTAATAAAGGTTCGAC
GTCGTTCAAAATATTATGCGCTTTTGTATTTCTTTCATCACTGTCGTTAGTGTACAATTGA
CTCGACGTAAACACGTTAAATAGAGCTTGGACATATTTAACATCGGGCGTGTTAGCTTTAT
TAGGCCGATTATCGTCGTCGTCCCAACCCTCGTCGTTAGAAGTTGCTTCCGAAGACGATTT
TGCCATAGCCACACGACGCCTATTAATTGTUTCGGCTAACACGTCCGCGATCAAATTTGTA
GTTGAGCTTTTTGGAATTATTTCTGATTGCGGGCGTTTTTGGGCGGGTTTCAATCTAACTT
GTGCCCGAVTTTAATTCAGACAACACGTTAGAAAGCGATGGTGCAGGCGGTGGTAACATTT
CAGACGGCAAATCTACTAATGGCGGCGGTGGTGGAGCTGATGATAAATCTACCATCGGTGG
AGGCGCAGGCGGGGCTGGCGGCGGAGGCGGAGGCGGAGGTGGTGGCGGTGATGCAGACGGC
GGTTTAGGCTCAAATGTCTCTTTAGGCAACACAGTCGGCACCTCAACTATTGTACTGGTTT
CGGGCGCCGTTTTTGGTTTGACCGGTCTGAGACGAGTGCGATTTTTTCGTTTCTAATAGC
TTCCAACAATTGTTGTCTGTCGTCTAAAGGTGCAGCGGGTTGAGGTTCCGTCGGCATTGGT
GGAGCGGGCGGCAATTCAGACATCGATGGTGGTGGTGGTGGAGGCGCTGGAATGTTAG
GCACGGGAGAAGGTGGTGGCGGCGGTGCCGCCGGTATAATFTGTTCTGGTTTAGTTTGTTC
GCGCACGATTGTGGGCACCGGCGCAGGCGCCGCTGGCTGCACAACGGAAGGTCGTCTGCTT
CGAGGCAGCGCTTGGGGTGGTGGCAATTCAATATTATAATTGGAATACAAATCGTAAAAAT
CTGCTATAAGCATTGTAATTTCGCTATCGTTTACCGTGCCGATATTTAACAACCGCTCAAT
GTAAGCAATTGTATTGTAAAGAGATTGTCTCAAGCTCGGATCGATCCCGCACGCCGATAAC
AAGCCTTTTCATTTTTACTACAGCATTGTAGTGGCGAGACACTTCGCTGTCGTCGAGGTTT
AAACGCTTCCTCGCTCACTGACTCGCTGCGCTCGGTCGTTCGGCTGCGGCGAGCGGTATCA
GCTCACTCAAAGGCGGTAATACGGTTATCCACAGAATCAGGGGATAACGCAGGAAAGAACA
TGTGAGCAAAAGGCCAGCAAAAGGCCAGGAACCGTAAAAAGGCCGCGTTGCTGGCGTTTTT
CCATAGGCTCCGCCCCCGGACGAGCATCACAAAAATCGACGCTCAAGTCAGAGGTGGCGAA
ACCCGACAGGACTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCTGG
GCTGTGTGCACGAACCCCCCGfTCAGCCCGACCGCTGCGCCTTATCCGGTAAGATCGTCTT
GAGTCCAACCCGGTAAGACACGACTTATCGCCACTGGCAGCAGCCACTGGTAACAGGATTA
GCAGAGCGAGGTATGTAGGCGGTGCTACAGAGTTCTTGAAGTGGTGGCCTAACTACGGCTA
CACTAGAAGGACAGTATTTGGTATCTGCGCTCTGCTGAAGCCAGTTACCTTCGGAAAAAGA
GTTGGTAGGGTGATCCGGCAAACAAACCACCGCTGGTAGCGGTGGTTTTTTGTTTGCAAG
CAGCAGATTACGCGCAGAAAAAAAGGATCTCAAGAAGATCGTTGATCTTTTCTACGGGGTC
```

-continued

```
TGACGCTCAGTGGAACGAAAACTCACGTTAAGGGATTTTGGTCATGAGATTATCAAAAAGG

ATGTCACCTAGATCCTTTTAAATTAAAAATGAAGTTTTAAATCAATCTAAAGTATATATGA

GTAAACTTGGTCTGACAGTTACCAATGCTTAATCAGTGAGGCACCTATCTCAGCGATCTGT

CTATTTCGTTCATCCATAGTTGCCTGAGCCCCGTCGTGTAGATAACTACGATACGGGAGGG

CTTACCATCTGGCCCCAGTGCTGCAATGATACCGCGAGACCCACGCTCACCGGCTCCAGAT

TTATCAGCAATAAACCAGCCAGCCGGAAGGGCCGAGCGCAGAAGTGGTCCTGCAACTTTAT

CCGCCTCCATCCAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCTCGTCGTTTGGT

ATGGCTTCCATTCAGCTCCGGTTCCCAACGATCAAGGCGAGTTACATGATCCCCCATGTTG

TGCAAAAAAGCGGTTAGCTCCTTCGGTCCTCCGATCGTTGTCAGAAGTAAGTTGGCCGCAG

TGTTATCACTCATGGTTATGGCAGCACTGCATAATTCTCTTACTGTCATGCCATCCGTAAG

ATGCTTTTCTGTGACTGGTGAGTACTCAACCAAGTCATTCTGAGAATAGTGTATGCGGCGA

CCGAGTTGCTCTTGCCCGGCGTCAATACGGGATAATACCGCGCCACATAGCAGAACTTTAA

AAGTGCTCATGCATTGGAAAACGTTCTTCGGGGCGAAAACTCTCAAGGATCTTACCGCTGT

TGAGATCCAGTTCGATGTAACCCACTCGTGCACCCAACTGATCTTCAGCATCTTTTACTTT

CACCAGCGTTTCTGGGTGAGCAAAAACAGGAAGGCAAAATGCCGCAAAAAAGGGAATAAGG

GCGACACGGAAATGTTGAATACTCATACTCTTCCTTTTTCAATATTATTGAAGCATTTATC

AGGGTTATTGTCTCATGAGCGGATACATATTTGAATGTATTTAGAAAAATAAACAAATAGG

GGTTCCGCGCACATTTCCCCGAAAAMGMACCTGACGCGCCCTGTAGCGGCGCATTAAGCGC

GGCGGGTGTGGTGGTTACGCGCAGCGTGACCGCTACACTTGCCAGCGCCCTAGCGCCCGCT

CCTTTCGCTTTCTTCCCTTCCTTTCTCGCCACGTTCGCCGGCTTTCCCCGTCAAGCTCTAA

ATCGGGGGCTCCCTTTAGGGTTCCGMTTAGTGCTTTACGGCACCTCGACCCCAAAAAACTT

GATTAGGGTGATGGTTCACGTAGTGGGCCATCGCCCTGATAGACGGTTTTTCGCCCTTTGA

CGTTGGAGTCCACGTTCTTTAATAGTGGACTCTTGTTCCAAAGGGAACAACACTCAACCCT

ATCTCGGTCTATTCTTTTGATTTATAAGGGATTTTGCCGATTTCGGCCTATTGGTTAAAAA

ATGAGCTGATTTAACAAAAATTTAACGCGAATTTTAACAAAATATTAACGTTTACAATTTC

CCATTCGCCATTCAGGCTGCGCAACTGTTGGGAAGGGCGATCGGTGCGGGCCTCTTCGCTA

TTACGCCA
```

Certain compounds of the disclosure were evaluated in HAQ STING in vitro binding assay as described above. The following table tabulates the biological data disclosed for the instant invention. The biological data was collected using the methodology described above. For each compound, STING IC$_{50}$ values are listed

TABLE 5

$^3$H-cGAMP filtration binding assay for HAQ STING

| Compound Number | HAQ STING IC$_{50}$ (nM) |
|---|---|
| 1-1 | 53 |
| 1-2 | 33 |
| 1-3 | 1159 |
| 1-4 | 732 |
| 1-5 | 11350 |
| 1-6 | 7551 |
| 1-7 | 12250 |
| 1-8 | 2971 |
| 1-9 | 1520 |
| 1-10 | 4225 |
| 1-11 | 10670 |
| 1-12 | 4443 |
| 1-13 | 15690 |
| 1-14 | 10870 |
| 1-15 | 16820 |
| 1-16 | 10210 |
| 1-17 | 3927 |
| 1-18 | 11310 |
| 1-19 | 2284 |
| 1-20 | 1631 |
| 1-21 | 3560 |
| 1-22 | 2243 |
| 1-23 | 858 |
| 1-24 | 9912 |

TABLE 5-continued $^3$H-cGAMP filtration binding assay for HAQ STING

| Compound Number | HAQ STING IC$_{50}$ (nM) |
| --- | --- |
| 1-25 | 11380 |
| 1-26 | 6643 |
| 1-27 | 2964 |
| 1-28 | 803 |
| 1-29 | 339 |
| 1-30 | 11460 |
| 1-31 | 1216 |
| 1-32 | 952 |
| 1-33 | 4874 |
| 1-34 | 10420 |
| 1-35 | 5288 |
| 1-36 | 669 |
| 1-37 | 339 |
| 1-38 | 3268 |
| 1-39 | 3752 |
| 1-40 | 483 |
| 1-41 | 1574 |
| 1-42 | 1240 |
| 1-43 | 828 |
| 1-44 | 5882 |
| 1-45 | 10880 |
| 1-46 | 1797 |
| 1-47 | 1135 |
| 1-48 | 213 |
| 1-49 | 18030 |
| 1-50 | 1288 |
| 1-51 | 4220 |
| 1-52 | 186 |
| 1-53 | 602 |
| 1-54 | 266 |
| 1-55 | 135 |
| 1-56 | 5696 |
| 1-57 | 9893 |
| 1-58 | 538 |
| 1-59 | 4135 |
| 1-60 | 7502 |
| 1-61 | 106 |
| 1-62 | 95 |
| 1-63 | 16670 |
| 1-64 | 225 |
| 1-65 | 1563 |
| 1-66 | 3439 |
| 1-67 | 122 |
| 1-68 | 1469 |
| 1-69 | 7611 |
| 1-70 | 1928 |
| 1-71 | 4638 |
| 1-72 | 737 |
| 1-73 | 6210 |
| 1-74 | 209 |
| 1-75 | 3208 |
| 1-76 | 357 |
| 1-77 | 41 |
| 1-78 | 670 |
| 1-79 | 482 |
| 1-80 | 602 |
| 1-81 | 441 |
| 1-82 | 329 |
| 1-83 | 10 |
| 1-84 | 55 |
| 1-85 | 68 |
| 1-86 | 1216 | cGAMP Stimulated THP1 Cytokine Inhibition-Assay

The ability of compounds to inhibit STING activation is quantified by their ability to inhibit cGAMP mediated cytokine production.

THP1 cells (catalog #TIB-202; American Type Culture collection (ATCC), Manassas, Va. USA) are grown in RPMI640 (catalog #11875-085; Thermo Fisher Scientific) with 10% fetal bovine serum (catalog #F2442, Sigma-Aldrich®, St. Louis, Mo., USA), 1×pen/strep (penicillin streptomycin, catalog #15140-148, Thermo Fisher Scientific) and 1 mM/sodium pyruvate (catalog #11360-070, Thermo Fisher Scientific) at a density between 0.3 and 1.0×10$^6$ cells/mL. Cells are diluted into RPMI1640+0.5% fetal bovine serum, and preincubated with antagonist compounds (30 μM to 1.75 μM from 10 mM DMSO stock solution) for six hours before stimulating with 2'3' cGAMP (InvivoGen, San Diego, Calif. USA)/Lipofectamine 2000 (catalog #11668-027, Thermo Fisher Scientific) overnight. IFNb is measured by ELISA (enzyme-linked immunosorbent assay for Interferon Beta; PBL InterferonSource, Piscataway, N.J., USA), and compared to cell viability with CellTiter-Glo® (Promega Life Sciences, Madison, Wis., USA).

Certain compounds of the disclosure were evaluated in in vitro cellular assay as described above. The following table tabulates the biological data disclosed for the instant invention. The biological data was collected using the methodology described above. For each compound, STING IC$_{50}$ values are listed

| Compound Number | THP1 Cell IC$_{50}$ (nM) |
| --- | --- |
| 1-1 | 11500 |
| 1-2 | 10000 |
| I-85 | 11400 |

What is claimed is:

1. A compound of formula I or a pharmaceutically acceptable salt thereof:

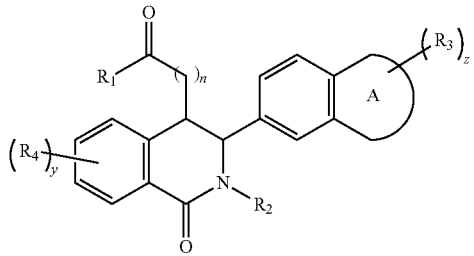

wherein: A is a 5- to 7-membered unsaturated non-aromatic ring having 1 or 2 heteroatoms independently selected from oxygen, nitrogen and sulfur;
$R_1$ is selected from —OH amino, —NHOH, —N($C_{1-6}$ alky)$_2$, and —N($C_{1-6}$ alkyl);
n is 0, 1, 2, or 3;
z is 0, 1, 2, or 3;
y is 0, 1, 2, or 3;
each $R_3$ is independently selected from $C_{1-10}$ alkyl, $C_{1-10}$ haloalkyl, $C_{3-7}$cycloalkyl$C_{0-6}$alkyl, and $C_{3-7}$ heterocycloalkyl$C_{0-6}$alkyl,
$R_2$ is phenyl or pyridyl, wherein $R_2$ is substituted by 0, 1, 2, or 3 $R_5$ substituents and wherein two $R_5$ may join together with the ring atoms to which they are attached to form a 3- to 6-membered ring;
each $R_4$ is independently selected from halogen, —($C_{1-6}$alkyl)OH, hydroxy, $C_{1-10}$ haloalkyl, $C_{2-10}$ alkenyl, $C_{1-6}$ alkyl, and aryl($C_{0-10}$ alkyl)oxy($C_{0-10}$ alkyl);
each $R_5$ is independently selected from:
halogen,
$C_{1-10}$ alkyl(oxy)$_{0-1}$$C_{0-10}$ alkyl,
$C_{1-10}$ heteroalkyl(oxy)$_{0-1}$$C_{0-10}$ alkyl,
$C_{2-10}$ alkenyl(oxy)$_{0-1}$$C_{0-10}$ alkyl,
aryl $C_{0-10}$ alkyl(oxy)$_{0-1}$$C_{0-10}$ alkyl,
$C_{3-12}$ cycloalkyl $C_{0-10}$ alkyl(oxy)$_{0-1}$$C_{0-10}$ alkyl,
heteroaryl $C_{0-10}$ alkyl(oxy)$_{0-1}$$C_{0-10}$ alkyl,
($C_{3-12}$)heterocycloalkyl $C_{0-10}$ alkyl(oxy)$_{0-1}$$C_{0-10}$ alkyl,
amino,
$C_{1-10}$ alkylamino$C_{0-10}$ alkyl,
($C_{1-10}$)heteroalkyl(oxy)$_{0-1}$(carbonyl)$_{0-1}$amino$C_{0-10}$ alkyl,
$C_{3-12}$ cycloalkyl $C_{0-10}$ alkyl(oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
($C_{3-12}$)heterocycloalkyl $C_{0-10}$ alkyl(oxy)$_{0-1}$(carbonyl)$_{0-1}$amino$C_{0-10}$ alkyl,
$C_{0-10}$ alkylamino (carbonyl)$_{0-1}$$C_{0-10}$ alkyl,
($C_{1-10}$)heteroalkylamino (carbonyl)$_{0-1}$$C_{0-10}$ alkyl,
$C_{3-12}$ cycloalkylamino (carbonyl)$_{0-1}$$C_{0-10}$ alkyl,
aryl $C_{0-10}$ alkylamino (carbonyl)$C_{0-10}$ alkyl,
heteroaryl $C_{0-10}$ alkylamino(carbonyl)$_{0-1}$$C_{0-10}$ alkyl,
($C_{3-12}$)heterocycloalkylamino(carbonyl)$_{0-1}$$C_{0-10}$ alkyl,
$C_{1-10}$ alkylsulfonyl$C_{0-10}$ alkyl,
$C_{1-10}$ heteroalkylsulfonyl$C_{1-10}$ alkyl,
($C_{3-12}$)cycloalkyl$C_{0-10}$alkylsulfonyl$C_{0-10}$ alkyl,
($C_{3-12}$)cycloheteroalkyl$C_{0-10}$alkylsulfonyl$C_{0-10}$ alkyl,
heteroaryl$C_{0-10}$ alkylsulfonyl$C_{0-10}$ alkyl,
aryl$C_{0-10}$ alkylsulfonyl$C_{0-10}$ alkyl,
$C_{1-10}$ alkylsulfonylamino$C_{0-10}$ alkyl,
($C_{1-10}$ alkyl)$_{1-2}$ amino,
—SO$_2$NH$_2$,
SO$_2$NH($C_{1-10}$ alkyl),
—SO$_2$N($C_{1-10}$ alkyl)$_2$,
—SO$_2$CF$_3$,
—SO$_2$CF$_2$H,
—SH,
—S($C_{1-10}$ alkyl),
—NH=CH$_2$,
hydroxy,
—($C_{1-10}$ alkyl)OH,
—$C_{0-10}$ alkylalkoxy,
cyano,
—($C_{1-6}$alkyl)cyano, and
$C_{1-6}$haloalkyl(oxy)$_{0-1}$; wherein each $R_5$ is substituted with 0, 1, 2 or 3 $R_6$ substituents each independently selected by halogen, cyano, oxo, $C_{1-10}$ alkylcarbonyl$C_{0-10}$ alkyl, $C_{1-10}$ alkyl, $C_{1-10}$ alkylcarbonylamino$C_{0-10}$ alkyl, and —($C_{1-10}$ alkyl)OH.

2. The compound according to claim 1, wherein $R_1$ is selected from —OH, amino, —NHOH, —N($C_{1-3}$alkyl)$_2$, and —N($C_{1-3}$alkyl) or a pharmaceutically acceptable salt thereof.

3. The compound according to claim 2, wherein $R_1$ is selected from —OH, amino, —NHOH, dimethylamino, and methylamino or a pharmaceutically acceptable salt thereof.

4. The compound according to claim 1, wherein each $R_3$ is independently selected from $C_{1-6}$ alkyl, $C_{1-6}$haloalkyl, $C_{3-7}$ cycloalkyl$C_{0-6}$alkyl, and $C_{3-7}$heterocycloalkyl$C_{0-6}$alkyl or a pharmaceutically acceptable salt thereof.

5. The compound according to claim 4, wherein each $R_3$ is independently selected from methyl, isopropyl, and cyclopropyl or a pharmaceutically acceptable salt thereof.

6. The compound according to claim 1, wherein each $R_4$ is independently selected from halogen, hydroxy, $C_{2-10}$ alkenyl, and aryl($C_{0-10}$alkyl)oxy($C_{0-10}$ alkyl) or a pharmaceutically acceptable salt thereof.

7. The compound according to claim 6, wherein each $R_4$ is independently selected from halogen, hydroxy, ethenyl, and phenylmethoxy or a pharmaceutically acceptable salt thereof.

8. The compound according to claim 1, wherein each $R_5$ is independently selected from: halogen, $C_{1-6}$ alkyl(oxy)$_{0-1}$$C_{0-10}$ alkyl, $C_{2-10}$ alkenyl, aryl $C_{0-10}$ alkyl(oxy)$_{0-1}$$C_{0-10}$ alkyl, $C_{3-12}$ cycloalkyl $C_{0-10}$ alkyl, heteroaryl $C_{0-10}$ alkyl, ($C_{3-12}$)heterocycloalkyl $C_{0-10}$ alkyl, $C_{1-10}$ alkylamino$C_{0-10}$ alkyl, aryl $C_{0-10}$ alkylamino (carbonyl)$C_{0-10}$ alkyl, $C_{1-10}$ alkylsulfonyl$C_{0-10}$ alkyl, $C_{1-10}$ alkylsulfonylamino$C_{0-10}$ alkyl, ($C_{1-10}$ alkyl)$_{1-2}$ amino, —SO$_2$NH($C_{1-10}$ alkyl), —SO2N($C_{1-10}$ alkyl)$_2$, —SH, —NH=CH$_2$, —($C_{1-10}$ alkyl)OH, —$C_{0-10}$ alkylalkoxy, cyano, —($C_{1-6}$alkyl)cyano, and $C_{1-6}$haloalkyl(oxy)$_{0-1}$; wherein each $R_5$ is substituted with 0, 1, 2, or 3 $R_6$ substituents or a pharmaceutically acceptable salt thereof.

9. The compound according to claim 8, wherein each $R_5$ is independently selected from: F, Cl, tert-butyl, isopropyl, methyl, ethyl, morpholinyl, methylsufonyl, dimethysulfamoyl, 1-cyano-1-methylethyl, cyclopropyl, piperazinyl, pyrazolyl, methoxy, —SH, —N=CH$_2$, methylamino, cyano, hydroxyethyl, 2,2,2-trifluoroethyloxy, phenylaminocarbonyl, cyclohexyl, propyl, ((methylsulfonyl)amino)methyl, morpholinylmethyl, phenylmethyloxy, Br, prop-2-enyl, hydroxymethyl, phenyl, and piperidinyl, wherein each $R_5$ is substituted with 0, 1, 2 or 3 $R_6$ substituents or a pharmaceutically acceptable salt thereof.

10. The compound according to claim 9, wherein each $R_6$ is independently selected from halogen, cyano, oxo, $C_{1-6}$ alkylcarbonyl, $C_{1-6}$ alkyl, $C_{1-6}$ alkylcarbonylamino, and $(C_{1-10}$ alkyl)OH or a pharmaceutically acceptable salt thereof.

11. The compound according to claim 10, wherein each $R_6$ is independently selected from halogen, methylcarbonyl, hydroxyethyl, oxo, cyano, hydroxymethyl, methylcarbonyl amino, and methyl or a pharmaceutically acceptable salt thereof.

12. The compound according to claim 1, wherein $R^5$ is selected from hydrogen, methyl, methylcarbonyl, ethyl, isopropyl, morpholinoethyl, 2-hydroxy-2-methylpropyl, 2-hydroxyethyl, 1-phenylethyl, benzyl, tetrahydro-2H-pyranylmethyl, 1-cyclopropylethyl, and tetrahydro-2H-pyranyl or a pharmaceutically acceptable salt thereof.

13. The compound according to claim 11, wherein $R^6$ is hydrogen or oxo or a pharmaceutically acceptable salt thereof.

14. The compound according to claim 1, wherein

[structure with ring A]

is selected from:

[six bicyclic structures shown: benzodioxine, benzodioxepine, chromane, dihydrobenzoxazine, benzodithiine, benzoxathiine variants]

or a pharmaceutically acceptable salt thereof.

15. The compound or a pharmaceutically acceptable salt, thereof, wherein the compound is selected from:

- (3S,4S)-2-(4-(tert-butyl)-3-chlorophenyl)-3-(2,3-dihydrobenzo[b][1,4]dioxin-6-yl)-1-oxo-1,2,3,4-tetrahydroisoquinoline-4-carboxylic acid;
- (3R,4R)-2-(4-(tert-butyl)-3-chlorophenyl)-3-(2,3-dihydrobenzo[b][1,4]dioxin-6-yl)-1-oxo-1,2,3,4-tetrahydroisoquinoline-4-carboxylic acid;
- (3S,4S)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinoline-4-carboxylic acid;
- (3R,4R)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinoline-4-carboxylic acid;
- (3R,4R)-3-(2,3-dihydro-1,4-benzodioxin-6-yl)-2-[4-(1-methylethyl)phenyl]-1-oxo-1,2,3,4-tetrahydroisoquinoline-4-carboxylic acid;
- (3S,4S)-3-(2,3-dihydro-1,4-benzodioxin-6-yl)-2-[4-(1-methylethyl)phenyl]-1-oxo-1,2,3,4-tetrahydroisoquinoline-4-carboxylic acid;
- (3R,4R)-3-(2,3-dihydro-1,4-benzodioxin-6-yl)-2-(2,3-dihydro-11H-inden-5-yl)-1-oxo-1,2,3,4-tetrahydroisoquinoline-4-carboxylic acid;
- (3S,4S)-3-(2,3-dihydro-1,4-benzodioxin-6-yl)-2-(2,3-dihydro-1H-inden-5-yl)-1-oxo-1,2,3,4-tetrahydroisoquinoline-4-carboxylic acid;
- (3R,4R)-3-(2,3-dihydro-1,4-benzodioxin-6-yl)-2-(4-morpholin-4-ylphenyl)-1-oxo-1,2,3,4-tetrahydroisoquinoline-4-carboxylic acid;
- (3S,4S)-3-(2,3-dihydro-1,4-benzodioxin-6-yl)-2-(4-morpholin-4-ylphenyl)-1-oxo-1,2,3,4-tetrahydroisoquinoline-4-carboxylic acid;
- (3R,4R)-3-(2,3-dihydro-1,4-benzodioxin-6-yl)-2-[4-(methylsulfonyl)phenyl]-1-oxo-1,2,3,4-tetrahydroisoquinoline-4-carboxylic acid;
- (3S,4S)-3-(2,3-dihydro-1,4-benzodioxin-6-yl)-2-[4-(methylsulfonyl)phenyl]-1-oxo-1,2,3,4-tetrahydroisoquinoline-4-carboxylic acid;
- (3R,4R)-3-(2,3-dihydro-1,4-benzodioxin-6-yl)-2-[4-(dimethylsulfamoyl)phenyl]-1-oxo-1,2,3,4-tetrahydroisoquinoline-4-carboxylic acid;
- (3S,4S)-3-(2,3-dihydro-1,4-benzodioxin-6-yl)-2-[4-(dimethylsulfamoyl)phenyl]-1-oxo-1,2,3,4-tetrahydroisoquinoline-4-carboxylic acid;
- (3R,4R)(-2-[4-(1-cyano-1-methylethyl)phenyl]-3-(2,3-dihydro-1,4-benzodioxin-6-yl)-1-oxo-1,2,3,4-tetrahydroisoquinoline-4-carboxylic acid;
- (3S,4S) (-2-[4-(1-cyano-1-methylethyl)phenyl]-3-(2,3-dihydro-1,4-benzodioxin-6-yl)-1-oxo-1,2,3,4-tetrahydroisoquinoline-4-carboxylic acid;
- (3R,4R)-2-(2-chloropyridin-4-yl)-3-(2,3-dihydro-1,4-benzodioxin-6-yl)-1-oxo-1,2,3,4-tetrahydroisoquinoline-4-carboxylic acid;
- (3S,4S)-2-(2-chloropyridin-4-yl)-3-(2,3-dihydro-1,4-benzodioxin-6-yl)-1-oxo-1,2,3,4-tetrahydroisoquinoline-4-carboxylic acid;
- (3R,4R)-2-(4-cyclopropylphenyl)-3-(2,3-dihydro-1,4-benzodioxin-6-yl)-1-oxo-1,2,3,4-tetrahydroisoquinoline-4-carboxylic acid;
- (3S,4S)-2-(4-cyclopropylphenyl)-3-(2,3-dihydro-1,4-benzodioxin-6-yl)-1-oxo-1,2,3,4-tetrahydroisoquinoline-4-carboxylic acid;
- (3S,4S)-2-[4-(4-acetylpiperazin-1-yl)phenyl]-3-(2,3-dihydro-,4-benzodioxin-6-yl)-1-oxo-1,2,3,4-tetrahydroisoquinoline-4-carboxylic acid;
- (3R,4R))-2-[4-(4-acetylpiperazin-1-yl)phenyl]-3-(2,3-dihydro-1,4-benzodioxin-6-yl)-1-oxo-1,2,3,4-tetrahydroisoquinoline-4-carboxylic acid;
- (3S,4S)-2-[4-(4-acetylpiperazin-1-yl)phenyl]-3-(2,3-dihydro-1,4-benzodioxin-6-yl)-1-oxo-1,2,3,4-tetrahydroisoquinoline-4-carboxylic acid;
- (3R,4R)-2-[4-(4-acetylpiperazin-1-yl)phenyl]-3-(2,3-dihydro-1,4-benzodioxin-6-yl)-1-oxo-1,2,3,4-tetrahydroisoquinoline-4-carboxylic acid;
- (3S,4S)-3-(2,3-dihydro-1,4-benzodioxin-6-yl)-2-{4-[1-(2-hydroxyethyl)-1H-pyrazol-4-yl]phenyl}-1-oxo-1,2,3,4-tetrahydroisoquinoline-4-carboxylic acid;
- (3R,4R)-3-(2,3-dihydro-1,4-benzodioxin-6-yl)-2-{4-[1-(2-hydroxyethyl)-1H-pyrazol-4-yl]phenyl}-1-oxo-1,2,3,4-tetrahydroisoquinoline-4-carboxylic acid;
- (3S,4S)-2-[4-(difluoromethoxy)phenyl]-3-(2,3-dihydro-1,4-benzodioxin-6-yl)-1-oxo-1,2,3,4-tetrahydroisoquinoline-4-carboxylic acid;

(3R,4R)-2-[4-(difluoromethoxy)phenyl]-3-(2,3-dihydro-1,4-benzodioxin-6-yl)-1-oxo-1,2,3,4-tetrahydroisoquinoline-4-carboxylic acid;

(3S,4S)-2-(1,3-benzothiazol-5-yl)-3-(2,3-dihydro-1,4-benzodioxin-6-yl)-1-oxo-1,2,3,4-tetrahydroisoquinoline-4-carboxylic acid;

(3R,4R)-2-(1,3-benzothiazol-5-yl)-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-(3,3-diethyl-2-oxo-2,3-dihydro-1H-indol-6-yl)-1-oxo-1,2,3,4-tetrahydroisoquinoline-4-carboxylic acid;

(3R,4R)-3-(2,3-dihydro-1,4-benzodioxin-6-yl)-2-(3,3-dimethyl-2-oxo-2,3-dihydro-1H-indol-6-yl)-1-oxo-1,2,3,4-tetrahydroisoquinoline-4-carboxylic acid;

(3S,4S)-3-(2,3-dihydro-1,4-benzodioxin-6-yl)-1-oxo-2-[4-(1H-pyrazol-5-yl)phenyl]-1,2,3,4-tetrahydroisoquinoline-4-carboxylic acid;

(3R,4R)-3-(2,3-dihydro-1,4-benzodioxin-6-yl)-1-oxo-2-[4-(1H-pyrazol-5-yl)phenyl]-1,2,3,4-tetrahydroisoquinoline-4-carboxylic acid;

(3S,4S)-2-(4-chloro-3-fluorophenyl)-3-(2,3-dihydro-1,4-benzodioxin-6-yl)-1-oxo-1,2,3,4-tetrahydroisoquinoline-4-carboxylic acid;

(3R,4R)-2-(4-chloro-3-fluorophenyl)-3-(2,3-dihydro-1,4-benzodioxin-6-yl)-1-oxo-1,2,3,4-tetrahydroisoquinoline-4-carboxylic acid;

(3S,4S)-2-(4-chloro-3-cyclopropylphenyl)-3-(2,3-dihydro-1,4-benzodioxin-6-yl)-1-oxo-1,2,3,4-tetrahydroisoquinoline-4-carboxylic acid;

(3R,4R)-2-(4-chloro-3-cyclopropylphenyl)-3-(2,3-dihydro-1,4-benzodioxin-6-yl)-1-oxo-1,2,3,4-tetrahydroisoquinoline-4-carboxylic acid;

(3S,4S)-2-(3-cyano-4-morpholin-4-ylphenyl)-3-(2,3-dihydro-1,4-benzodioxin-6-yl)-1-oxo-1,2,3,4-tetrahydroisoquinoline-4-carboxylic acid;

(3R,4R)-2-(3-cyano-4-morpholin-4-ylphenyl)-3-(2,3-dihydro-1,4-benzodioxin-6-yl)-1-oxo-1,2,3,4-tetrahydroisoquinoline-4-carboxylic acid;

(3S,4S)-2-[3-chloro-4-(difluoromethoxy)phenyl]-3-(2,3-dihydro-1,4-benzodioxin-6-yl)-1-oxo-1,2,3,4-tetrahydroisoquinoline-4-carboxylic acid;

(3R,4R)-2-[3-chloro-4-(difluoromethoxy)phenyl]-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-[4-(2-hydroxy-1,1-dimethylethyl)phenyl]-1-oxo-1,2,3,4-tetrahydroisoquinoline-4-carboxylic acid;

(3R,4R)-3-(2,3-dihydro-1,4-benzodioxin-6-yl)-2-[4-(2-hydroxy-1,1-dimethylethyl)phenyl]-1-oxo-1,2,3,4-tetrahydroisoquinoline-4-carboxylic acid;

(3S,4S)-2-(3-chlorophenyl)-3-(2,3-dihydro-1,4-benzodioxin-6-yl)-1-oxo-1,2,3,4-tetrahydroisoquinoline-4-carboxylic acid;

(3R,4R)-2-(3-chlorophenyl)-3-(2,3-dihydro-1,4-benzodioxin-6-yl)-1-oxo-1,2,3,4-tetrahydroisoquinoline-4-carboxylic acid;

(3S,4S)-2-(3-chloro-4-morpholin-4-ylphenyl)-3-(2,3-dihydro-1,4-benzodioxin-6-yl)-1-oxo-1,2,3,4-tetrahydroisoquinoline-4-carboxylic acid;

(3R,4R)-2-(3-chloro-4-morpholin-4-ylphenyl)-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-(2-methylpyridin-4-yl)-1-oxo-1,2,3,4-tetrahydroisoquinoline-4-carboxylic acid;

(3R,4R)-3-(2,3-dihydro-1,4-benzodioxin-6-yl)-2-(2-methylpyridin-4-yl)-1-oxo-1,2,3,4-tetrahydroisoquinoline-4-carboxylic acid;

(3S,4S)-3-(2,3-dihydro-1,4-benzodioxin-6-yl)-1-oxo-2-[4-(2,2,2-trifluoroethoxy)phenyl]-1,2,3,4-tetrahydroisoquinoline-4-carboxylic acid;

(3R,4R)-3-(2,3-dihydro-1,4-benzodioxin-6-yl)-1-oxo-2-[4-(2,2,2-trifluoroethoxy)phenyl]-1,2,3,4-tetrahydroisoquinoline-4-carboxylic acid;

(3S,4S)-2-{4-[(4-chlorophenyl)carbamoyl]phenyl}-3-(2,3-dihydro-1,4-benzodioxin-6-yl)-1-oxo-1,2,3,4-tetrahydroisoquinoline-4-carboxylic acid;

(3R,4R)-2-{4-[(4-chlorophenyl)carbamoyl]phenyl}-3-(2,3-dihydro-1,4-benzodioxin-6-yl)-1-oxo-1,2,3,4-tetrahydroisoquinoline-4-carboxylic acid;

(3S,4S)-2-(4-cyclohexylphenyl)-3-(2,3-dihydro-1,4-benzodioxin-6-yl)-1-oxo-1,2,3,4-tetrahydroisoquinoline-4-carboxylic acid;

(3R,4R)-2-(4-cyclohexylphenyl)-3-(2,3-dihydro-1,4-benzodioxin-6-yl)-1-oxo-1,2,3,4-tetrahydroisoquinoline-4-carboxylic acid;

(3S,4S)-2-[4-(1-cyanocyclohexyl)phenyl]-3-(2,3-dihydro-1,4-benzodioxin-6-yl)-1-oxo-1,2,3,4-tetrahydroisoquinoline-4-carboxylic acid;

(3S,4R)-2-[4-(1-cyanocyclohexyl)phenyl]-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-1-oxo-2-(5,6,7,8-tetrahydronaphthalen-2-yl)-1,2,3,4-tetrahydroisoquinoline-4-carboxylic acid;

(3S,4R)-3-(2,3-dihydro-1,4-benzodioxin-6-yl)-1-oxo-2-(5,6,7,8-tetrahydronaphthalen-2-yl)-1,2,3,4-tetrahydroisoquinoline-4-carboxylic acid;

(3S,4S)-3-(2,3-dihydro-1,4-benzodioxin-6-yl)-2-(2-fluoropyridin-4-yl)-1-oxo-1,2,3,4-tetrahydroisoquinoline-4-carboxylic acid;

(3R,4R)-3-(2,3-dihydro-1,4-benzodioxin-6-yl)-2-(2-fluoropyridin-4-yl)-1-oxo-1,2,3,4-tetrahydroisoquinoline-4-carboxylic acid;

(3S,4S)-3-(2,3-dihydro-1,4-benzodioxin-6-yl)-2-[6-(hydroxymethyl)-5,6,7,8-tetrahydronaphthalen-2-yl]-1-oxo-1,2,3,4-tetrahydroisoquinoline-4-carboxylic acid;

(3R,4R)-3-(2,3-dihydro-1,4-benzodioxin-6-yl)-2-[6-(hydroxymethyl)-5,6,7,8-tetrahydronaphthalen-2-yl]-1-oxo-1,2,3,4-tetrahydroisoquinoline-4-carboxylic acid;

(3S,4S)-2-(2-chloro-6-methylpyridin-4-yl)-3-(2,3-dihydro-1,4-benzodioxin-6-yl)-1-oxo-1,2,3,4-tetrahydroisoquinoline-4-carboxylic acid;

(3R,4R)-2-(2-chloro-6-methylpyridin-4-yl)-3-(2,3-dihydro-1,4-benzodioxin-6-yl)-1-oxo-1,2,3,4-tetrahydroisoquinoline-4-carboxylic acid;

(3S,4S)-2-(4-chloro-3-methylphenyl)-3-(2,3-dihydro-1,4-benzodioxin-6-yl)-1-oxo-1,2,3,4-tetrahydroisoquinoline-4-carboxylic acid;

(3R,4R)-2-(4-chloro-3-methylphenyl)-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-(4-{[(methylsulfonyl)amino]methyl}phenyl)-1-oxo-1,2,3,4-tetrahydroisoquinoline-4-carboxylic acid;

(3R,4R)-3-(2,3-dihydro-1,4-benzodioxin-6-yl)-2-(4-{[(methylsulfonyl)amino]methyl}phenyl)-1-oxo-1,2,3,4-tetrahydroisoquinoline-4-carboxylic acid;

(3S,4S)-3-(2,3-dihydro-1,4-benzodioxin-6-yl)-2-(2,6-dimethylpyridin-4-yl)-1-oxo-1,2,3,4-tetrahydroisoquinoline-4-carboxylic acid;

(3R,4R)-3-(2,3-dihydro-,4-benzodioxin-6-yl)-2-(2,6-dimethylpyridin-4-yl)-1-oxo-1,2,3,4-tetrahydroisoquinoline-4-carboxylic acid;

(3S,4S)-2-[4-(1-cyanocyclohexyl)phenyl]-3-(2,3-dihydro-1,4-benzodioxin-6-yl)-1-oxo-1,2,3,4-tetrahydroisoquinoline-4-carboxylic acid;

(3R,4R)-2-[4-(1-cyanocyclohexyl)phenyl]-3-(2,3-dihydro-1,4-benzodioxin-6-yl)-1-oxo-1,2,3,4-tetrahydroisoquinoline-4-carboxylic acid;

(3R,4R)-3-(2,3-dihydro-1,4-benzodioxin-6-yl)-1-oxo-2-(5,6,7,8-tetrahydronaphthalen-2-yl)-1,2,3,4-tetrahydroisoquinoline-4-carboxylic acid;

(3S,4S)-3-(2,3-dihydro-1,4-benzodioxin-6-yl)-1-oxo-2-(5,6,7,8-tetrahydronaphthalen-2-yl)-1,2,3,4-tetrahydroisoquinoline-4-carboxylic acid;

(3S,4S)-2-[3-chloro-4-(morpholin-4-ylmethyl)phenyl]-3-(2,3-dihydro-1,4-benzodioxin-6-yl)-1-oxo-1,2,3,4-tetrahydroisoquinoline-4-carboxylic acid;

(3R,4R)-2-[3-chloro-4-(morpholin-4-ylmethyl)phenyl]-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-(3,4-dimethylphenyl)-1-oxo-1,2,3,4-tetrahydroisoquinoline-4-carboxylic acid;

(3R,4R)-3-(2,3-dihydro-1,4-benzodioxin-6-yl)-2-(3,4-dimethylphenyl)-1-oxo-1,2,3,4-tetrahydroisoquinoline-4-carboxylic acid;

(3S,4S)-2-(3,4-dichlorophenyl)-3-(2,3-dihydro-1,4-benzodioxin-6-yl)-1-oxo-1,2,3,4-tetrahydroisoquinoline-4-carboxylic acid;

(3R,4R)-2-(3,4-dichlorophenyl)-3-(2,3-dihydro-1,4-benzodioxin-6-yl)-1-oxo-1,2,3,4-tetrahydroisoquinoline-4-carboxylic acid;

(3S,4S)-2-[4-(benzyloxy)-3-chlorophenyl]-3-(2,3-dihydro-1,4-benzodioxin-6-yl)-1-oxo-1,2,3,4-tetrahydroisoquinoline-4-carboxylic acid;

(3R,4R)-2-[4-(benzyloxy)-3-chlorophenyl]-3-(2,3-dihydro-1,4-benzodioxin-6-yl)-1-oxo-1,2,3,4-tetrahydroisoquinoline-4-carboxylic acid;

(3S,4S)-2-(3-bromophenyl)-3-(2,3-dihydro-1,4-benzodioxin-6-yl)-1-oxo-1,2,3,4-tetrahydroisoquinoline-4-carboxylic acid;

(3R,4R)-2-(3-bromophenyl)-3-(2,3-dihydro-1,4-benzodioxin-6-yl)-1-oxo-1,2,3,4-tetrahydroisoquinoline-4-carboxylic acid;

(3S,4S)-2-(4-cyclopropyl-3-fluorophenyl)-3-(2,3-dihydro-1,4-benzodioxin-6-yl)-1-oxo-1,2,3,4-tetrahydroisoquinoline-4-carboxylic acid;

(3R,4R)-2-(4-cyclopropyl-3-fluorophenyl)-3-(2,3-dihydro-1,4-benzodioxin-6-yl)-1-oxo-1,2,3,4-tetrahydroisoquinoline-4-carboxylic acid;

(3S,4S)-2-[4-(1-cyanocyclohexyl)phenyl]-3-(3,4-dihydro-2H-1-,5-benzodioxepin-7-yl)-1-oxo-1,2,3,4-tetrahydroisoquinoline-4-carboxylic acid;

(3R,4R)-2-[4-(1-cyanocyclohexyl)phenyl]-3-(3,4-dihydro-2H-1,5-benzodioxepin-7-yl)-1-oxo-1,2,3,4-tetrahydroisoquinoline-4-carboxylic acid;

(3R,4R)-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

(3S,4S)-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

(3S,4S)-6-bromo-3-(2,3-dihydro-1,4-benzodioxin-6-yl)-2-(2,3-dihydro-1H-inden-5-yl)-1-oxo-1,2,3,4-tetrahydroisoquinoline-4-carboxylic acid;

(3R,4R)-6-bromo-3-(2,3-dihydro-1,4-benzodioxin-6-yl)-2-(2,3-dihydro-1H-inden-5-yl)-1-oxo-1,2,3,4-tetrahydroisoquinoline-4-carboxylic acid;

(3S,4S)-3-(2,3-dihydro-1,4-benzodioxin-6-yl)-2-naphthalen-2-yl-1-oxo-1,2,3,4-tetrahydroisoquinoline-4-carboxylic acid;

(3R,4R)-3-(2,3-dihydro-1,4-benzodioxin-6-yl)-2-naphthalen-2-yl-1-oxo-1,2,3,4-tetrahydroisoquinoline-4-carboxylic acid;

(3S,4S)-3-(2,3-dihydro-1,4-benzodioxin-6-yl)-1-oxo-2-(3,4,5-trichlorophenyl)-1,2,3,4-tetrahydroisoquinoline-4-carboxylic acid;

(3R,4R)-3-(2,3-dihydro-1,4-benzodioxin-6-yl)-1-oxo-2-(3,4,5-trichlorophenyl)-1,2,3,4-tetrahydroisoquinoline-4-carboxylic acid;

(3S,4S)-2-[3-chloro-4-(1-cyano-1-methylethyl)phenyl]-3-(2,3-dihydro-,4-benzodioxin-6-yl)-1-oxo-1,2,3,4-tetrahydroisoquinoline-4-carboxylic acid;

(3R,4R)-2-[3-chloro-4-(1-cyano-1-methylethyl)phenyl]-3-(2,3-dihydro-1,4-benzodioxin-6-yl)-1-oxo-1,2,3,4-tetrahydroisoquinoline-4-carboxylic acid;

(3S,4S)-6-bromo-2-(3-chloro-4-methylphenyl)-3-(2,3-dihydro-1,4-benzodioxin-6-yl)-1-oxo-1,2,3,4-tetrahydroisoquinoline-4-carboxylic acid;

(3R,4R)-6-bromo-2-(3-chloro-4-methylphenyl)-3-(2,3-dihydro-1,4-benzodioxin-6-yl)-1-oxo-1,2,3,4-tetrahydroisoquinoline-4-carboxylic acid;

(3S,4S)-7-bromo-2-(3-chloro-4-methylphenyl)-3-(2,3-dihydro-1,4-benzodioxin-6-yl)-1-oxo-1,2,3,4-tetrahydroisoquinoline-4-carboxylic acid;

(3R,4R)-7-bromo-2-(3-chloro-4-methylphenyl)-3-(2,3-dihydro-1,4-benzodioxin-6-yl)-1-oxo-1,2,3,4-tetrahydroisoquinoline-4-carboxylic acid;

(3S,4S)-3-(2,3-dihydro-1,4-benzodioxin-6-yl)-2-(3,4-dihydro-1H-isochromen-7-yl)-1-oxo-1,2,3,4-tetrahydroisoquinoline-4-carboxylic acid;

(3R,4R)-3-(2,3-dihydro-1,4-benzodioxin-6-yl)-2-(3,4-dihydro-1H-isochromen-7-yl)-1-oxo-1,2,3,4-tetrahydroisoquinoline-4-carboxylic acid;

(3R,4R)-2-(3-chloro-4-cyclohexylphenyl)-3-(2,3-dihydro-1,4-benzodioxin-6-yl)-1-oxo-1,2,3,4-tetrahydroisoquinoline-4-carboxylic acid;

(3S,4S)-2-(3-chloro-4-cyclohexylphenyl)-3-(2,3-dihydro-1,4-benzodioxin-6-yl)-1-oxo-1,2,3,4-tetrahydroisoquinoline-4-carboxylic acid;

(3R,4R)-2-(4-tert-butyl-3-chlorophenyl)-3-(3,4-dihydro-2H-chromen-6-yl)-1-oxo-1,2,3,4-tetrahydroisoquinoline-4-carboxylic acid;

(3S,4S)-2-(4-tert-butyl-3-chlorophenyl)-3-(3,4-dihydro-2H-chromen-6-yl)-1-oxo-1,2,3,4-tetrahydroisoquinoline-4-carboxylic acid;

(3S,4S)-7-bromo-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

(3R,4R)-7-bromo-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

(3S,4S)-2-(4-tert-butyl-3-chlorophenyl)-7-chloro-3-(2,3-dihydro-1,4-benzodioxin-6-yl)-1-oxo-1,2,3,4-tetrahydroisoquinoline-4-carboxylic acid;

(3R,4R)-2-(4-tert-butyl-3-chlorophenyl)-7-chloro-3-(2,3-dihydro-1,4-benzodioxin-6-yl)-1-oxo-1,2,3,4-tetrahydroisoquinoline-4-carboxylic acid;

(3S,4S)-7-(benzyloxy)-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

(3R,4R)-7-(benzyloxy)-2-(4-tert-butyl-3-chlorophenyl)-3-(2,3-dihydro-1,4-benzodioxin-6-yl)-1-oxo-1,2,3,4-tetrahydroisoquinoline-4-carboxylic acid;

(3R,4R)-2-(4-tert-butyl-3-chlorophenyl)-3-(2,3-dihydro-1,4-benzodioxin-6-yl)-6-fluoro-1-oxo-1,2,3,4-tetrahydroisoquinoline-4-carboxylic acid;

(3S,4S)-2-(4-tert-butyl-3-chlorophenyl)-3-(2,3-dihydro-1,4-benzodioxin-6-yl)-6-fluoro-1-oxo-1,2,3,4-tetrahydroisoquinoline-4-carboxylic acid;

(3R,4R)-2-(4-tert-butyl-3-chlorophenyl)-3-(2,3-dihydro-1,4-benzodioxin-6-yl)-6-fluoro-1-oxo-1,2,3,4-tetrahydroisoquinoline-4-carboxylic acid;

(3S,4S)-2-(4-tert-butyl-3-chlorophenyl)-3-(2,3-dihydro-1,4-benzodioxin-6-yl)-6-fluoro-1-oxo-1,2,3,4-tetrahydroisoquinoline-4-carboxylic acid;

(3R,4R)-2-(4-tert-butyl-3-chlorophenyl)-7-chloro-3-(2,3-dihydro-1,4-benzodioxin-6-yl)-1-oxo-1,2,3,4-tetrahydroisoquinoline-4-carboxylic acid;

(3S,4S)-2-(4-tert-butyl-3-chlorophenyl)-7-chloro-3-(2,3-dihydro-1,4-benzodioxin-6-yl)-1-oxo-1,2,3,4-tetrahydroisoquinoline-4-carboxylic acid;

(3R,4R)-2-(4-tert-butyl-3-chlorophenyl)-3-(4-methyl-3,4-dihydro-2H-1,4-benzoxazin-6-yl)-1-oxo-1,2,3,4-tetrahydroisoquinoline-4-carboxylic acid;

(3S,4S)-2-(4-tert-butyl-3-chlorophenyl)-3-(4-methyl-3,4-dihydro-2H-1,4-benzoxazin-6-yl)-1-oxo-1,2,3,4-tetrahydroisoquinoline-4-carboxylic acid;

(3R,4R)-2-(4-tert-butyl-3-chlorophenyl)-3-(4-methyl-3,4-dihydro-2H-1,4-benzoxazin-6-yl)-1-oxo-1,2,3,4-tetrahydroisoquinoline-4-carboxylic acid;

(3S,4S)-2-(4-tert-butyl-3-chlorophenyl)-3-(4-methyl-3,4-dihydro-2H-1,4-benzoxazin-6-yl)-1-oxo-1,2,3,4-tetrahydroisoquinoline-4-carboxylic acid;

(3S,4S)-2-(4-tert-butyl-3-chlorophenyl)-3-(2,3-dihydro-1,4-benzodioxin-6-yl)-7-hydroxy-1-oxo-1,2,3,4-tetrahydroisoquinoline-4-carboxylic acid;

(3R,4R)-2-(4-tert-butyl-3-chlorophenyl)-3-(2,3-dihydro-1,4-benzodioxin-6-yl)-7-hydroxy-1-oxo-1,2,3,4-tetrahydroisoquinoline-4-carboxylic acid;

(3S,4S)-2-[3-chloro-4-(1-cyanocyclopropyl)phenyl]-3-(2,3-dihydro-1,4-benzodioxin-6-yl)-1-oxo-1,2,3,4-tetrahydroisoquinoline-4-carboxylic acid;

(3R,4R)-2-[3-chloro-4-(l-cyanocyclopropyl)phenyl]-3-(2,3-dihydro-1,4-benzodioxin-6-yl)-1-oxo-1,2,3,4-tetrahydroisoquinoline-4-carboxylic acid;

(3R,4R)-2-[3-chloro-4-(1-cyanocyclopropyl)phenyl]-3-(2,3-dihydro-1,4-benzodioxin-6-yl)-1-oxo-1,2,3,4-tetrahydroisoquinoline-4-carboxylic acid;

(3S,4S)-2-[3-chloro-4-(1-cyanocyclopropyl)phenyl]-3-(2,3-dihydro-1,4-benzodioxin-6-yl)-1-oxo-1,2,3,4-tetrahydroisoquinoline-4-carboxylic acid;

(3R,4R)-2-(4'-acetamido-[1,1-biphenyl]-4-yl)-3-(2,3-dihydrobenzo[b][1,4]dioxin-6-yl)-1-oxo-1,2,3,4-tetrahydroisoquinoline-4-carboxylic acid;

(3S,4S)-2-(4'-acetamido-[1,1'-biphenyl]-4-yl)-3-(2,3-dihydrobenzo[b][1,4]dioxin-6-yl)-1-oxo-1,2,3,4-tetrahydroisoquinoline-4-carboxylic acid;

(3S,4S)-2-[4-(1-acetylpiperidin-4-yl)phenyl]-3-(2,3-dihydro-1,4-benzodioxin-6-yl)-1-oxo-1,2,3,4-tetrahydroisoquinoline-4-carboxylic acid;

(3R,4R)-2-[4-(1-acetylpiperidin-4-yl)phenyl]-3-(2,3-dihydro-1,4-benzodioxin-6-yl)-1-oxo-1,2,3,4-tetrahydroisoquinoline-4-carboxylic acid;

(3R,4R)-2-(4'-acetamido-2-chloro-[1,1'-biphenyl]-4-yl)-3-(2,3-dihydrobenzo[b][1,4]dioxin-6-yl)-1-oxo-1,2,3,4-tetrahydroisoquinoline-4-carboxylic acid;

(3S,4S)-2-(4'-acetamido-2-chloro-[1,1'-biphenyl]-4-yl)-3-(2,3-dihydrobenzo[b][1,4]dioxin-6-yl)-1-oxo-1,2,3,4-tetrahydroisoquinoline-4-carboxylic acid;

(3S,4S)-2-(4-(tert-butyl)-3-chlorophenyl)-3-(2,3-dihydrobenzo[b][1,4]dioxin-6-yl)-N-methyl-1-oxo-1,2,3,4-tetrahydroisoquinoline-4-carboxamide;

(3R,4R)-2-(4-(tert-butyl)-3-chlorophenyl)-3-(2,3-dihydrobenzo[b][1,4]dioxin-6-yl)-N-methyl-1-oxo-1,2,3,4-tetrahydroisoquinoline-4-carboxamide;

(3S,4S)-2-(4-tert-butyl-3-chlorophenyl)-3-(2,3-dihydro-1,4-benzodioxin-6-yl)-1-oxo-1,2,3,4-tetrahydroisoquinoline-4-carboxamide;

(3R,4R)-2-(4-tert-butyl-3-chlorophenyl)-3-(2,3-dihydro-1,4-benzodioxin-6-yl)-1-oxo-1,2,3,4-tetrahydroisoquinoline-4-carboxamide;

(3S,4S)-2-(4-tert-butyl-3-chlorophenyl)-3-(2,3-dihydro-1,4-benzodioxin-6-yl)-N,N-dimethyl-1-oxo-1,2,3,4-tetrahydroisoquinoline-4-carboxamide;

(3R,4R)-2-(4-tert-butyl-3-chlorophenyl)-3-(2,3-dihydro-1,4-benzodioxin-6-yl)-N,N-dimethyl-1-oxo-1,2,3,4-tetrahydroisoquinoline-4-carboxamide;

(3S,4S)-2-(4-tert-butyl-3-chlorophenyl)-3-(2,3-dihydro-1,4-benzodioxin-6-yl)-7-fluoro-1-oxo-1,2,3,4-tetrahydroisoquinoline-4-carboxamide;

(3R,4R)-2-(4-tert-butyl-3-chlorophenyl)-3-(2,3-dihydro-1,4-benzodioxin-6-yl)-7-fluoro-1-oxo-1,2,3,4-tetrahydroisoquinoline-4-carboxamide;

(3S,4S)-2-(4-(tert-butyl)-3-chlorophenyl)-3-(2,3-dihydrobenzo[b][1,4]dioxin-6-yl)-1-oxo-7-vinyl-1,2,3,4-tetrahydroisoquinoline-4-carboxylic acid;

(3R,4R)-2-(4-(tert-butyl)-3-chlorophenyl)-3-(2,3-dihydrobenzo[b][1,4]dioxin-6-yl)-1-oxo-7-vinyl-1,2,3,4-tetrahydroisoquinoline-4-carboxylic acid;

(3R,4R)-2-(4-(tert-butyl)-3-chlorophenyl)-3-(2,3-dihydrobenzo[b][1,4]dithiin-6-yl)-1-oxo-1,2,3,4-tetrahydroisoquinoline-4-carboxylic acid;

(3S,4S)-2-(4-(ter-butyl)-3-chlorophenyl)-3-(2,3-dihydrobenzo[b][1,4]dithiin-6-yl)-1-oxo-1,2,3,4-tetrahydroisoquinoline-4-carboxylic acid;

(3R,4R)-2-(4-(tert-butyl)-3-chlorophenyl)-3-(2,3-dihydrobenzo[b][1,4]oxathiin-6-yl)-1-oxo-1,2,3,4-tetrahydroisoquinoline-4-carboxylic acid;

(3S,4S)-2-(4-(tert-butyl)-3-chlorophenyl)-3-(2,3-dihydrobenzo[b][1,4]oxathiin-6-yl)-1-oxo-1,2,3,4-tetrahydroisoquinoline-4-carboxylic acid;

(3R,4R)-2-(4-(tert-butyl)-3-chlorophenyl)-3-(2,3-dihydrobenzo[b][1,4]oxathiin-7-yl)-1-oxo-1,2,3,4-tetrahydroisoquinoline-4-carboxylic acid;

(3S,4S)-2-(4-(tert-butyl)-3-chlorophenyl)-3-(2,3-dihydrobenzo[b][1,4]oxathiin-7-yl)-1-oxo-1,2,3,4-tetrahydroisoquinoline-4-carboxylic acid;

(3R,4R)-2-(4-(tert-butyl)-3-chlorophenyl)-3-(2,3-dihydrobenzo[b][1,4]dioxin-6 yl)-N-hydroxy-1-oxo-1,2,3,4-tetrahydroisoquinoline-4-carboxamide;

(3S,4S)-2-(4-(tert-butyl)-3-chlorophenyl)-3-(2,3-dihydrobenzo[b][1,4]dioxin-6-yl)-N-hydroxyl-oxo-1,2,3,4-tetrahydroisoquinoline-4-carboxamide;

(3S,4S)-2-(4-(tert-butyl)-3-chlorophenyl)-3-(chroman-6-yl)-1-oxo-1,2,3,4-tetrahydroisoquinoline-4-carboxylic acid;

(3R,4R)-2-(4-(tert-butyl)-3-chlorophenyl)-3-(chroman-6-yl)-1-oxo-1,2,3,4-tetrahydroisoquinoline-4-carboxylic acid;

(3S,4S)-2-(4-(tert-butyl)-3-chlorophenyl)-3-(3,4-dihydro-2H-benzo[b][1,4]oxazin-6-yl)-1-oxo-1,2,3,4-tetrahydroisoquinoline-4-carboxylic acid;

(3R,4R)-2-(4-(tert-butyl)-3-chlorophenyl)-3-(3,4-dihydro-2H-benzo[b][1,4]oxazin-6-yl)-1-oxo-1,2,3,4-tetrahydroisoquinoline-4-carboxylic acid;

(3S,4S)-2-(4-(tert-butyl)-3-chlorophenyl)-3-(4-isopropyl-3,4-dihydro-2H-benzo[b][1,4]oxazin-6-yl)-1-oxo-1,2,3,4-tetrahydroisoquinoline-4-carboxylic acid;

(3R,4R)-2-(4-(tert-butyl)-3-chlorophenyl)-3-(4-isopropyl-3,4-dihydro-2H-benzo[b][1,4]oxazin-6-yl)-1-oxo-1,2,3,4-tetrahydroisoquinoline-4-carboxylic acid;

(3S,4S)-2-(4-(tert-butyl)-3-chlorophenyl)-3-(3-cyclopropyl-2,3-dihydrobenzo[b][1,4]dioxin-6-yl)-7-fluoro-1-oxo-1,2,3,4-tetrahydroisoquinoline-4-carboxylic acid;

(3R,4R)-2-(4-(tert-butyl)-3-chlorophenyl)-3-(3-cyclopropyl-2,3-dihydrobenzo[b][1,4]dioxin-6-yl)-7-fluoro-1-oxo-1,2,3,4-tetrahydroisoquinoline-4-carboxylic acid;

(3S,4S)-2-(4-(tert-butyl)-3-chlorophenyl)-3-(2,3-dihydrobenzo[b][1,4]oxathiin-6-yl)-7-fluoro-1-oxo-1,2,3,4-tetrahydroisoquinoline-4-carboxylic acid;

(3R,4R)-2-(4-(tert-butyl)-3-chlorophenyl)-3-(2,3-dihydrobenzo[b][1,4]oxathiin-6-yl)-7-fluoro-1-oxo-1,2,3,4-tetrahydroisoquinoline-4-carboxylic acid;

2-((3S,4S)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinolin-4-yl)acetic acid;

2-((3R,4R)-2-(4-(tert-butyl)-3-chlorophenyl)-3-(2,3-dihydrobenzo[b][1,4]dioxin-6-yl)-7-fluoro-1-oxo-1,2,3,4-tetrahydroisoquinolin-4-yl)acetic acid;

(3R,4R)-3-(2,3-dihydrobenzo[b][1,4]dioxin-6-yl)-2-((S)-6-(hydroxymethyl)-5,6,7,8-tetrahydronaphthalen-2-yl)-1-oxo-1,2,3,4-tetrahydroisoquinoline-4-carboxylic acid;

(3R,4R)-3-(2,3-dihydrobenzo[b][1,4]dioxin-6-yl)-2-((R)-6-(hydroxymethyl)-5,6,7,8-tetrahydronaphthalen-2-yl)-1-oxo-1,2,3,4-tetrahydroisoquinoline-4-carboxylic acid;

(3S,4S)-3-(2,3-dihydrobenzo[b][1,4]dioxin-6-yl)-2-((S)-6-(hydroxymethyl)-5,6,7,8-tetrahydronaphthalen-2-yl)-1-oxo-1,2,3,4-tetrahydroisoquinoline-4-carboxylic acid; and (3S,4S)-3-(2,3-dihydrobenzo[b][1,4]dioxin-6-yl)-2-((R)-6-(hydroxymethyl)-5,6,7,8-tetrahydronaphthalen-2-yl)-1-oxo-1,2,3,4-tetrahydroisoquinoline-4-carboxylic acid.

16. The pharmaceutical composition comprising a compound of claim 1 or a pharmaceutically acceptable salt thereof and a pharmaceutically acceptable carrier.

17. The pharmaceutical composition according to claim 16, further comprising one or more other therapeutic agents.

18. A method for the treatment of a STING-mediated disease comprising administering to a patient in need thereof a therapeutically effective amount of a compound of claim 1 or a pharmaceutically acceptable salt thereof.

19. A method of treating a condition in a mammal that can be ameliorated by the selective inhibition of STING which condition is selected from: arthritis, asthma and obstructive airways diseases, autoimmune diseases or disorders, and cancer comprising administering to the mammal in need of such treatment, a therapeutically effective amount of a compound according to claim 1 or a pharmaceutically acceptable salt thereof.

20. The method according to claim 19, wherein said condition is arthritis.

21. The method according to claim 20, wherein said condition is selected from rheumatoid arthritis, juvenile arthritis, and psoriatic arthritis.

22. The method according to claim 19, wherein said condition is asthma or obstructive airways diseases.

23. The method according to claim 22, wherein said condition is selected from: chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease (COPD), and emphysema.

24. The method according to claim 19, wherein said condition is asthma.

25. The method according to claim 19, wherein said condition is cancer.

* * * * *